(12) United States Patent
Kolb et al.

(10) Patent No.: US 9,925,126 B2
(45) Date of Patent: Mar. 27, 2018

(54) AEROGELS, CALCINED AND CRYSTALLINE ARTICLES AND METHODS OF MAKING THE SAME

(71) Applicant: 3M INNOVATIVE PROPERTIES COMPANY, St. Paul, MN (US)

(72) Inventors: Brant U. Kolb, Afton, MN (US); Bryan C. Feisel, Hudson, WI (US); Martin Goetzinger, Pflugdorf (DE); Philip S. Hall, Savage, MN (US); Holger Hauptmann, Sindelsdorf (DE); Mark J. Hendrickson, Minneapolis, MN (US); Kathleen M. Humpal, Stillwater, MN (US); John W. Longabach, St. Louis, MO (US); James P. Mathers, Alpharetta, GA (US); Roberta R. Naujok, Hudson, WI (US); Paul D. Pennington, Farmington, MN (US); Gallus Schechner, Herrsching (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 15/486,579

(22) Filed: Apr. 13, 2017

(65) Prior Publication Data
US 2017/0216153 A1 Aug. 3, 2017

Related U.S. Application Data

(62) Division of application No. 14/347,382, filed as application No. PCT/US2012/049505 on Aug. 3, 2012, now Pat. No. 9,657,152.
(Continued)

(51) Int. Cl.
*A61K 6/02* (2006.01)
*C04B 35/64* (2006.01)
(Continued)

(52) U.S. Cl.
CPC ........... *A61K 6/024* (2013.01); *A61C 5/20* (2017.02); *A61C 5/77* (2017.02); *A61C 7/282* (2013.01); *A61C 8/0001* (2013.01); *A61C 8/0012* (2013.01); *A61C 8/0048* (2013.01); *A61C 13/0006* (2013.01); *A61C 13/0022* (2013.01); *A61C 13/082* (2013.01); *A61K 6/0002* (2013.01); *A61K 6/0008* (2013.01); *A61K 6/025* (2013.01); *A61K 6/0255* (2013.01); *A61K 6/083* (2013.01); *B82Y 30/00* (2013.01); *C01G 25/00* (2013.01); *C01G 25/006* (2013.01); *C01G 25/02* (2013.01); *C04B 35/486* (2013.01); *C04B 35/488* (2013.01); *C04B 35/624* (2013.01); *C04B 35/64* (2013.01); *C08J 9/008* (2013.01); *C08J 9/28* (2013.01); *C01P 2002/50* (2013.01); *C01P 2002/52* (2013.01); *C01P 2002/60* (2013.01); *C01P 2002/84* (2013.01); *C01P 2004/62* (2013.01); *C01P 2004/64* (2013.01); *C01P 2006/10* (2013.01); *C04B 2235/3217* (2013.01); *C04B 2235/3225* (2013.01); *C04B 2235/3227* (2013.01); *C04B 2235/3244* (2013.01); *C04B 2235/549* (2013.01); *C04B 2235/6562* (2013.01); *C04B 2235/6565* (2013.01); *C04B 2235/6567* (2013.01); *C04B 2235/661* (2013.01); *C04B 2235/77* (2013.01); *C04B 2235/781* (2013.01); *C04B 2235/785* (2013.01); *C04B 2235/80* (2013.01); *C04B 2235/96* (2013.01); *C04B 2235/9646* (2013.01);
(Continued)

(58) Field of Classification Search
CPC ............ A61C 13/0006; A61C 13/0022; A61C 13/082; A61C 5/20; A61C 5/77; A61C 7/282; A61C 8/0001; A61C 8/0012; A61C 8/0048; A61K 6/0002; A61K 6/0008; A61K 6/024; A61K 6/025; A61K 6/0255; A61K 6/083; B82Y 30/00; C01G 25/00; C01G 25/006; C01G 25/02; C04B 35/486; C04B 35/488; C04B 35/624; C04B 35/64; C08J 9/008; C08J 9/28
USPC ........................................................ 428/220
See application file for complete search history.

(56) References Cited

U.S. PATENT DOCUMENTS

| 5,238,625 A | 8/1993 | Sakurai |
| 5,453,262 A | 9/1995 | Dawson |

(Continued)

FOREIGN PATENT DOCUMENTS

| CN | 101456569 | 6/2009 |
| EP | 2045222 | 4/2009 |

(Continued)

OTHER PUBLICATIONS

Chervin et al. (Aerogel Synthesis of Yttria-Stabilized Zirconia by a Non-Alkoxide Sol-Gel Route; Chem. Mater. 2005, 17, 3345-3351).*
(Continued)

*Primary Examiner* — Ling Choi
*Assistant Examiner* — Chun-Cheng Wang
(74) *Attorney, Agent, or Firm* — Jean A. Lown

(57) ABSTRACT

Aerogel, calcined articles, and crystalline articles comprising $ZrO_2$. Exemplary uses of the crystalline metal oxide articles include dental articles (e.g., restoratives, replacements, inlays, onlays, veneers, full and partial crowns, bridges, implants, implant abutments, copings, anterior fillings, posterior fillings, and cavity liner, and bridge frameworks) and orthodontic appliances (e.g., brackets, buccal tubes, cleats, and buttons).

17 Claims, 4 Drawing Sheets

Related U.S. Application Data

(60) Provisional application No. 61/545,243, filed on Oct. 10, 2011.

(51) Int. Cl.

| | | |
|---|---|---|
| *C04B 35/488* | (2006.01) | |
| *C01G 25/02* | (2006.01) | |
| *A61K 6/00* | (2006.01) | |
| *A61C 13/08* | (2006.01) | |
| *C08J 9/28* | (2006.01) | |
| *A61C 7/28* | (2006.01) | |
| *A61C 13/00* | (2006.01) | |
| *A61C 8/00* | (2006.01) | |
| *C04B 35/624* | (2006.01) | |
| *A61K 6/083* | (2006.01) | |
| *C01G 25/00* | (2006.01) | |
| *C04B 35/486* | (2006.01) | |
| *B82Y 30/00* | (2011.01) | |
| *C08J 9/00* | (2006.01) | |
| *A61C 5/77* | (2017.01) | |
| *A61C 5/20* | (2017.01) | |

(52) U.S. Cl.
CPC . *C04B 2235/9661* (2013.01); *C08J 2201/038* (2013.01); *C08J 2201/04* (2013.01); *C08J 2201/0502* (2013.01); *C08J 2203/08* (2013.01); *C08J 2205/026* (2013.01); *C08J 2205/042* (2013.01); *C08J 2207/10* (2013.01); *C08J 2333/02* (2013.01); *C08J 2333/10* (2013.01); *C08J 2333/14* (2013.01); *Y02P 20/544* (2015.11)

(56) References Cited

U.S. PATENT DOCUMENTS

| | | |
|---|---|---|
| 5,652,192 A | 7/1997 | Matson |
| 5,789,075 A | 8/1998 | Frank |
| 5,989,698 A | 11/1999 | Mrozinski |
| 6,280,744 B1 | 8/2001 | Schwertfeger |
| 6,365,638 B1 | 4/2002 | Schwertfeger |
| 6,486,291 B2 | 11/2002 | Mrozinski |
| 7,241,437 B2 | 7/2007 | Davidson |
| 7,429,422 B2 | 9/2008 | Davidson |
| 7,674,476 B1 | 3/2010 | Schwertfeger |
| 8,734,931 B2 | 5/2014 | Seth |
| 2006/0148950 A1 | 7/2006 | Davidson |
| 2006/0281825 A1 | 12/2006 | Lee |
| 2009/0047562 A1 | 2/2009 | Hata |
| 2010/0041542 A1 | 2/2010 | Rolf |
| 2015/0203650 A1 | 7/2015 | Kolb |

FOREIGN PATENT DOCUMENTS

| | | |
|---|---|---|
| JP | 2003-192452 | 7/2003 |
| JP | 2008-214168 | 9/2008 |
| WO | WO 2005/091972 | 10/2005 |
| WO | WO 2008/083282 | 7/2008 |
| WO | WO 2009/085926 | 7/2009 |
| WO | WO 2010/045105 | 4/2010 |
| WO | WO 2011/082022 | 7/2011 |
| WO | WO 2011/082031 | 7/2011 |
| WO | WO 2014/209626 | 12/2014 |

OTHER PUBLICATIONS

Adschiri, "Rapid and Continuous Hydrothermal Crystallization of Metal Oxide Particles in Supercritical Water", Journal of the American Ceramic Society, 1992, vol. 75, No. 4, pp. 1019-1022.

Blumenthal, The Chemical Behavior of Zirconium, pp. 311-338 (1958).

Bravo-Leon, "Fracture toughness of nanocrystalline tetragonal zirconia with low yttria content", Journal of Acta Materialia, 2002, vol. 50, pp. 4555-4562.

Brinker, "Sol-Gel Science: The Physics and Chemistry of Sol-Gel Processing", pp. 730 (1990).

Chevalier, "Low-Temperature Degradation of Zirconia and Implications for Biomedical Implants," Annu. Rev. Mater. Res. 2007, vol. 37, pp. 1-32.

Chevalier, "The Tetragonal-Monoclinic Transformation in Zirconia: Lessons Learned and Future Trends," Journal of the American Ceramic Society, Sep. 2009, vol. 92, No. 9, pp. 1901-1920.

Cottom, "Fracture Toughness of Nanocrystalline $ZrO_2$—3mol% $Y_2O_3$ Determined by Vickers Indentation", Scripta Materialia, 1996, vol. 34, No. 5, pp. 809-814.

Dawson, "Hydrothermal Synthesis of Advanced Ceramic Powders", Ceramic Bulletin, 1988, vol. 67, No. 10, pp. 1673-1678.

Francis, "Ternary Systems of Liquid Carbon Dioxide", Journal of Physical Chemistry, Dec. 1954, vol. 58, pp. 1099-1114.

Stocker, "Zirconia Aerogels and Xerogels; Influence of Solvent and Acid on Structural Properties", Journal of Porous Materials, 1995, vol. 2, pp. 171-183.

Van Bommel, "Drying of silica gels with supercritical carbon dioxide", Journal of Materials Science, 1994, vol. 29, pp. 943-948.

Zhang, "Fabrication of Bulk Macroporous Zirconia by Combining Sol-gel with Calcination Process", Sep. 2011, vol. 37, No. 7, pp. 2549-2533.

International Search Report for PCT International Application No. PCT/US2012/049505, dated Nov. 8, 2012, 4 pages.

Annex to the European Search Report on European Patent Application No. EP 17190809, dated Nov. 7, 2017, 7 pages.

* cited by examiner

AEROGELS, CALCINED AND CRYSTALLINE ARTICLES AND METHODS OF MAKING THE SAME

CROSS REFERENCE TO RELATED APPLICATIONS

This application is a divisional application of prior U.S. application Ser. No. 14/347,382, now allowed, filed Jul. 1, 2014, which is a National Stage Entry under PCT/US2012/049505, filed Aug. 3, 2012, which claims priority from U.S. Provisional Application No. 61/545,243, filed Oct. 10, 2011, the disclosures of which are incorporated herein by reference in their entireties.

BACKGROUND

Dental restorations such as crowns and bridges are commonly made by what is known as the porcelain fused to metal process. A metal coping or support structure is covered with layers of glass having different levels of translucency. Opaque layers cover the metal to hide its color followed by more translucent layers to improve the aesthetic appearance. In recent years there has been a trend toward all ceramic dental restorations; crowns, bridges, inlays, etc. In particular, metal copings which provide the structural support for crowns and bridges are being replaced by high strength ceramics. These materials have color and translucency characteristics which better match the natural tooth and produce a more aesthetic appearance.

Zirconia is a preferred material for this application because of its high strength and toughness. Pure zirconia exists in three crystalline forms; monoclinic, tetragonal, and cubic. Monoclinic is stable from room temperature up to about 950-1200° C., tetragonal is the stable form from 1200° C. to about 2370° C., and cubic is stable above 2370° C. Sintering zirconia to high density generally requires temperatures above 1100° C. The monoclinic phase typically transforms to tetragonal during sintering, but then transforms back to monoclinic on cooling. Unfortunately, this transformation is accompanied by a volume expansion which causes the ceramic to crack and usually break apart. Stabilizing agents such as yttria can be added to zirconia to avoid this destructive transformation. Typically, when greater than about 2 mole percent yttria is added, the tetragonal phase can be retained as a metastable phase during cooling. When more than about 8 mole percent yttria is added the cubic phase forms at sintering temperatures and is retained during cooling. Between these levels of yttria a mixture of the tetragonal and cubic phases are formed during sintering and usually retained during cooling. Under rapid cooling conditions the cubic phase may be distorted to form another tetragonal phase known as tetragonal prime.

Zirconia stabilized with 2-3 mole percent of yttria is especially attractive as a structural ceramic because it can exhibit a large degree of transformation toughening. At this level of yttria the material consists largely of metastable tetragonal crystals with the balance being cubic or tetragonal prime. When a crack passes through the material it triggers transformation of the tetragonal crystals near the crack tip to the monoclinic form along with the associated volume expansion. This localized expansion resists the extension of the crack acting as a toughening mechanism.

The amount of toughening is dependent on the grain size, yttria content, and the matrix constraint. As the grain size is reduced the tetragonal form becomes more stable. Optimum toughening is obtained when the grain size is just below the critical grain size where the tetragonal phase is metastable. If the grain size exceeds the critical size the tetragonal phase can convert spontaneously to the monoclinic form throughout the bulk of the material causing widespread cracking. If the grain size is too far below the critical size than the tetragonal crystals are so stable that they will not revert to monoclinic in the stress field of a crack tip. As the amount of yttria stabilizer in the tetragonal form is reduced the tetragonal form becomes thermodynamically less stable and the critical grain size is reduced.

Generally as discussed in *Scripta Materialia*, 34(5) 809-814 (1996), at an overall composition of 3 mole percent yttria excellent toughening is obtained with grain sizes near 500 nm, but the toughness is reduced at grain sizes near 100 nm. While the overall composition is 3 mole percent yttria, the tetragonal phase contains about 2 mole percent yttria, the remainder is in the cubic phase that is also present. As the bulk yttria content changes from 2-9 mole percent over the range where the tetragonal and cubic phases coexist, the yttria constant of the tetragonal phase itself is constant. As a result the critical grain size is also constant over this range. It should be expected then that as the grain size of the two phase materials is reduced to values approaching 100 nm the effect of transformation toughening will also be reduced. Some insight into the absolute minimum grain size which can provide a toughening effect can be found in studies of pure tetragonal materials where the amount of yttria can be reduced to lower levels. Further as generally discussed in *Journal of Acta Materialia*, 50, pages 4555-62, (2002), if the amount of yttria is reduced to 1 mole percent, excellent toughening can be obtained at 90 nm, but falls rapidly below about 75 nm.

As the overall yttria composition increases over the tetragonal plus cubic range there will be decreasing amounts of the tetragonal phase present. Therefore, the toughness and strength of materials would be expected to drop as the amount of tetragonal phase in the material is reduced.

Matrix constraint is the resistance adjacent crystals exert on a tetragonal crystal as it tries to transform (expand) against its surroundings. In a fully dense material the adjacent grains provide a high degree of matrix restraint. A porous material provides room for local expansion and therefore less matrix restraint.

In summary, optimum toughening and strength are expected when the grain size is just below the critical grain size for a given yttria content, the material is fully dense, and contains a high fraction of the tetragonal phase. Improvements in optical translucency achieved by grain size reduction must be balanced against the loss in toughness expected at grain sizes below 100 nm, and especially below 75 nm. Improvements in optical transmission which might be expected with higher cubic content must also be balanced by the loss in toughness expected with fewer tetragonal grains.

The high strength and toughness of zirconia makes milling of intricate shapes from fully dense material very difficult. The milling operation is slow and tool wear is high. To overcome this limitation the zirconia may be milled to shape using a partially densified (calcined) body, referred to as a mill block. The mill block is typically 50% dense. It has sufficient strength for handling and is readily milled with minimal tool wear. The shaped restoration can then be heated (sintered) to form a fully dense article which is strong and somewhat translucent. During the sintering process the material shrinks roughly 20% in linear dimensions as it becomes denser. This shrinkage can be accounted for by using optical scanners and computer design to obtain a three-dimensional image of the restoration. This image file can be expanded to compensate for the sintering shrinkage, then transferred to a computer controlled milling machine to produce the restoration. Sintering at high temperature produces the final densified restoration.

While zirconia has a limited amount of translucency, higher translucency is desired to achieve even better appearance for dental applications. Ceramics are often opaque in appearance due to the scattering of light by pores in the ceramic. In order to achieve even a limited level of translucency, the density of the ceramic is typically greater than 99% of theoretical. Higher clarity can require levels above 99.9% or even 99.99%. Two methods known in the art for achieving very high densities in ceramic materials are hot isostatic pressing and spark plasma sintering. However the equipment required for these methods is relatively expensive and is not well suited for use in most dental restoration laboratories. Also, protective atmospheres and/or graphite dies used in this equipment can lead to discoloration of the zirconia by chemical reduction (loss of oxygen from the zirconia).

Another factor which can limit the translucency of ceramics is the presence of two or more solid phases having a different refractive index. In such cases to improve transparency, it is necessary to reduce the size of these phases well below the wavelength of visible light to avoid excessive scattering. Even in single phase materials scattering can occur if the material exhibits birefringence (i.e., has a different refractive index in different crystal directions). Light is then refracted and reflected (scattered) as it crosses grain boundaries from one crystal to another having a different orientation. In this case the crystallite size needs also to be less than the wavelength of visible light to achieve high levels of translucency. For these reasons highly translucent ceramics are often fabricated from single phase, cubic materials which exhibit no birefringence. In the case of zirconia ceramics, however, strength is compromised as the cubic form of zirconia is not transformation toughened.

Sintering of nanoparticles (10-100 nm) is one way to produce small grains in ceramics. The small size increases the driving force for densification (i.e., the reduction in surface area). Unfortunately nanoparticles tend to form strong agglomerates which do not easily break down during pressing operations. The particles within an agglomerate are generally packed more densely than the surrounding particles leading to a non-uniform pore structure in the final sintered body. Obtaining fully dense, highly translucent articles, without the use of high pressure techniques has proven difficult.

Sol-gel processing of nanometer sized particles is one way of avoiding agglomeration and achieving the high density and small grain size desired for both strength and translucency. The difficulty with this processing approach is that it does not lend itself to the production of relatively large articles. It has been successfully applied to the manufacture of fibers, beads, and abrasive grit, but it is not well suited to the production of bulk articles greater than about 1 mm in size. The problem has been in drying the gel where capillary forces lead to high shrinkage and cracking unless relatively lengthy drying techniques are used. In addition, for nanoparticle sols having organic stabilizing agents to keep the particles well dispersed, it can be difficult to remove these organics during heating without crack formation. The dense packing of nanoparticles in the dry bodies means the open pore channels needed to remove volatiles are relatively small leading to pressure build-up within the body. Also, if the organics separate the individual particles of the dry body, shrinkage will occur as the organics are removed. Since organic is most easily volatilized near the surface, non-uniform shrinkage is likely.

It is known that supercritical extraction of liquid from bulk gels can eliminate cracking during drying because there are no capillary forces present. Further, the lack of capillary forces to pull the particles together tends to lead to more relatively open structures commonly referred to as aerogels. Aerogels can have pore volumes of 90% or more. The more open structure of an aerogel would be expected to aid in uniform volatilization of any organics present. However, the low relative density of an aerogel (typically <10% of theoretical) presents a problem as it is generally known that high packing densities of the particles are desirable for densification during sintering. While silica aerogels have been successfully sintered to full density, it has not been considered possible to sinter crystalline aerogels to full density. Silica sinters by a viscous flow process which is much faster than the solid state diffusion mechanisms responsible for sintering crystalline solids.

SUMMARY

In one aspect, the present disclosure describes an aerogel (in some embodiments, a monolithic aerogel (i.e., having x, y, and z dimensions of at least 1 mm (in some embodiments, at least 1.5 mm, 2 mm, 3 mm, 4 mm, 5 mm, 6 mm, 7 mm, 8 mm, 9 mm, or even at least 10 mm)) comprising organic material and crystalline metal oxide particles, wherein the crystalline metal oxide particles are in a range from 3 to 20 volume percent, based on the total volume of the aerogel, wherein at least 70 (in some embodiments, at least 75, 80, 85, 90, 95, 96, 97, 98, or even at least 99; in a range from 70 to 99, 75 to 99, 80 to 99, or even 85 to 99) mole percent of the crystalline metal oxide is $ZrO_2$. An advantage of embodiments of aerogels described herein is that they can be sintered to a fully dense material despite the fact that they have low relative density and are comprised of crystalline particles.

In another aspect, the present disclosure provides a method of making aerogels described herein, the method comprising:

providing a first zirconia sol comprising crystalline metal oxide particles having an average primary particle size of not greater than 50 nanometers, wherein at least 70 mole percent of the crystalline metal oxide is $ZrO_2$;

optionally concentrating the first zirconia sol to provide a concentrated zirconia sol;

adding a radically reactive surface modifier to the zirconia sol (or understood to be the concentrated zirconia sol, as applicable) to provide a radically polymerizable surface-modified zirconia sol;

adding a radical initiator to the radically polymerizable surface-modified zirconia sol;

heating at at least one temperature for a time sufficient to polymerize the radically surface-modified zirconia sol comprising the radical initiator to form a gel;

optionally removing water from the gel via alcohol exchange to provide an at least partially de-watered gel; and extracting alcohol from the gel (or understood to be the at least partially de-watered gel, as applicable) via super critical extraction to provide the aerogel.

In another aspect, the present disclosure provides a crack-free, calcined metal oxide article (e.g., having x, y, and z dimensions of at least 5 mm) a density in a range from 30 to 95 percent of theoretical density, and an average connected pore size in a range from 10 nm to 100 nm, wherein at least 70 mole percent of the metal oxide is crystalline $ZrO_2$, and wherein the crystalline $ZrO_2$ has an average grain size less than 100 nm.

In another aspect, the present disclosure provides a method of making crack-free, calcined metal oxide articles described herein, the method comprising heating aerogels described herein for a time and at at least one temperature sufficient to provide the crack-free, calcined metal oxide articles.

In another aspect, the present invention provides a crack-free, crystalline metal oxide article having x, y, and z dimensions of at least 3 mm and a density of at least 98.5 (in some embodiments, 99, 99.5, 99.9, or even at least 99.99) percent of theoretical density, wherein at least 70 mole percent of the crystalline metal oxide is $ZrO_2$, wherein from 1 to 15 mole percent (in some embodiments 1 to 9 mole percent) of the crystalline metal oxide is $Y_2O_3$, and wherein the $ZrO_2$ has an average grain size in a range from 75 nanometers to 400 nanometers. In calculating the theoretical density, the volume of unit cell is measured by XRD for each composition or calculated via ionic radii and crystal type.

$$\rho_{theory} = \frac{N_c A}{V_c N_A}$$

Where
$N_c$ = number of atoms in unit cell;
A = Atomic Weight [kg mol$^{-1}$];
$V_c$ = Volume of unit cell [m$^3$]; and
$N_A$ = Avogadro's number [atoms mol$^{-1}$].

In another aspect, the present disclosure provides a method of making a crack-free, crystalline metal oxide article having x, y, and z dimensions of at least 3 mm and a density of at least 98.5 (in some embodiments, 99, 99.5, 99.9, or even at least 99.99) percent of theoretical density, wherein at least 70 mole percent of the metal oxide is crystalline $ZrO_2$, wherein from 1 to 5 mole percent (in some embodiments 3.5 to 4.5 mole percent) of the crystalline metal oxide is $Y_2O_3$, and wherein the crystalline $ZrO_2$ has an average grain size in a range from 75 nanometers to 175 nanometers, the method comprising heating a crack-free, calcined metal oxide article described herein for a time and at at least one temperature sufficient to provide the crack-free, crystalline metal oxide article.

In another aspect, the present invention provides a crack-free, crystalline metal oxide article having x, y, and z dimensions of at least 3 mm and a density of at least 98.5 (in some embodiments, 99, 99.5, 99.9, or even at least 99.99) percent of theoretical density, wherein at least 70 mole percent of the crystalline metal oxide is $ZrO_2$, wherein from 1 to 5 mole percent (in some embodiments, 3.5 to 4.5 mole percent) of the crystalline metal oxide is $Y_2O_3$, and wherein the $ZrO_2$ has an average grain size in a range from 75 nanometers to 175 nanometers (in some embodiments, in a range from 100 nanometers to 165 nanometers).

In another aspect, the present disclosure provides a method of making a crack-free, crystalline metal oxide article having x, y, and z dimensions of at least 3 mm and a density of at least 98.5 (in some embodiments, 99, 99.5, 99.9, or even at least 99.99) percent of theoretical density, wherein at least 70 mole percent of the metal oxide is crystalline $ZrO_2$, wherein from 1 to 15 mole percent (in some embodiments 1 to 9 mole percent) of the crystalline metal oxide is $Y_2O_3$, and wherein the crystalline $ZrO_2$ has an average grain size in a range from 75 nanometers to 400 nanometers, the method comprising heating a crack-free, calcined metal oxide article described herein for a time and at at least one temperature sufficient to provide the crack-free, crystalline metal oxide article.

In another aspect, the present invention provides a crack-free, crystalline metal oxide article having x, y, and z dimensions of at least 3 mm and a density of at least 98.5 (in some embodiments, 99, 99.5, 99.9, or even at least 99.99) percent of theoretical density, wherein at least 70 mole percent of the crystalline metal oxide is $ZrO_2$, wherein in range from 6 to 9 mole percent (in some embodiments 7 to 8 mole percent) of the crystalline metal oxide is $Y_2O_3$, and wherein the $ZrO_2$ has an average grain size in a range from 100 nanometers to 400 nanometers (in some embodiments, in a range from 200 nanometers to 300 nanometers).

In another aspect, the present disclosure provides a method of making a crack-free, crystalline metal oxide article having x, y, and z dimensions of at least 3 mm and a density of at least 98.5 (in some embodiments, 99, 99.5, 99.9, or even at least 99.99) percent of theoretical density, wherein at least 70 mole percent of the crystalline metal oxide is $ZrO_2$, wherein in range from 6 to 9 mole percent (in some embodiments 7 to 8 mole percent) of the crystalline metal oxide is $Y_2O_3$, and wherein the $ZrO_2$ has an average grain size in a range from 100 nanometers to 400 nanometers, the method comprising heating a crack-free, calcined metal oxide article described herein for a time and at at least one temperature sufficient to provide the crack-free, crystalline metal oxide article.

In another aspect, the present disclosure provides a method of making a crack-free, crystalline metal oxide article having x, y, and z dimensions of at least 3 mm and a density of at least 98.5 (in some embodiments, 99, 99.5, 99.9, or even at least 99.99) percent of theoretical density, wherein at least 70 mole percent of the crystalline metal oxide is $ZrO_2$, and wherein the $ZrO_2$ has an average grain size less than 300 nanometers, the method comprising pressureless heating in air a crack-free, calcined metal oxide article having x, y, and z dimensions of at least 3 mm, a density in a range from 30 to 95 percent of theoretical density, wherein at least 70 mole percent of the metal oxide is crystalline $ZrO_2$, and wherein the crystalline $ZrO_2$ has an average grain size less than 100 nm for a time and at at least one temperature sufficient to provide the crack-free, crystalline metal oxide article, wherein the method is conducted at no greater than 1400° C. (in some embodiments, at at least one temperature in a range from 1000° C. to 1400° C., 1000° C. to 1350° C., or even 1200° C. to 1300° C.).

In this application:

"aggregation" refers to a strong association of two or more primary particles. For example, the primary particles may be chemically bound to one another. The breakdown of aggregates into smaller particles (e.g., primary particles) is generally difficult to achieve.

"aerogel" refers to a three-dimensional low density (i.e., less than 20% of theoretical density) solid. Aerogels are typically formed from a gel by solvent removal, for example, under supercritical conditions. During this process the network does not substantially shrink and a highly porous, homogeneous, low-density material could be obtained.

"agglomeration" refers to a weak association of two or more primary particles. For example, the primary particles may be held together by charge or polarity. The breakdown of agglomerates into smaller particles (e.g., primary particles) is less difficult than the breakdown of aggregates into smaller particles.

"associated" refers to a grouping of two or more primary particles that are aggregated and/or agglomerated. Similarly, the term "non-associated" refers to two or more primary particles that are free or substantially free from aggregation and/or agglomeration.

"calcining" refers to a process of heating solid material to drive off at least 90 percent by weight of volatile chemically bond components (e.g., organic components) (vs., for example, drying, in which physically bonded water is driven off by heating). Calcining is typically done at a temperature below a temperature needed to conduct a pre-sintering step.

"crack-free" means no cracks are visible from 15 cm (6 inches) away when viewed with 20-20 vision (if desired, a microscope can be used wherein the sample is observed using polarized light in transmission);

"crack" means a material segregation or partitioning (i.e. defect), wherein the ratio of the segregation or partitioning is about 1:10 in two dimensions, wherein for the thermal untreated material one dimension unit is above about 40 µm. A surface defect having one maximum dimension below 40 µm is not regarded as a crack.

"ceramic" means an inorganic non-metallic material that is produced by application of heat. Ceramics are usually hard, porous and brittle and, in contrast to glasses or glass ceramics, display an essentially purely crystalline structure.

"crystalline" means a solid composed of atoms arranged in a pattern periodic in three dimensions (i.e., has long range crystal structure as determined by X-ray diffraction).

"dental mill block" refers to a solid block (three-dimensional article) of material from which a dental article, dental workpiece, dental support structure or dental restoration can be machined. A dental mill blank may have a size of about 20 mm to about 30 mm in two dimensions, for example, may have a diameter in that range, and may be of a certain length in a third dimension. A blank for making a single crown may have a length of about 15 mm to about 30 mm, and a blank for making bridges may have a length of about 40 mm to about 80 mm. A typical size of a blank as it is used for making a single crown has a diameter of about 24 mm and a length of about 19 mm. Further, a typical size of a blank as it is used for making bridges has a diameter of about 24 mm and a length of about 58 mm. Besides the above mentioned dimensions, a dental mill blank may also have the shape of a cube, a cylinder or a cuboid. Larger mill blanks may be advantageous if more than one crown or bridge should be manufactured out of one blank. For these cases, the diameter or length of a cylindric or cuboid shaped mill blank may be in a range of about 100 to about 200 mm, with a thickness being in the range of about 10 to about 30 mm.

"dental ceramic article" means any article which can or is to be used in the dental or orthodontic field, especially for producing of or as dental restoration, a tooth model and parts thereof.

Examples of dental articles include crowns (including monolithic crowns), bridges, inlays, onlays, veneers, facings, copings, crown and bridged framework, implants, abutments, orthodontic appliances (e.g. brackets, buccal tubes, cleats and buttons) and parts thereof. The surface of a tooth is considered not to be a dental article.

"hydrothermal" refers to a method of heating an aqueous medium to a temperature above the normal boiling point of the aqueous medium at a pressure that is equal to or greater than the pressure required to prevent boiling of the aqueous medium.

"in the range" includes the endpoints of the range and all numbers between the endpoints. For example, in the range from 1 to 10 includes the numbers 1 and 10 as well as all numbers between 1 and 10.

"organic matrix" refers to any organic compound or mixture of such compounds. The organic matrix often includes one or more organic solvents, one or more monomers, one or more oligomers, one or more polymeric materials, or a combination thereof. In many embodiments, the organic matrix is an organic solvent and a polymerizable composition, or a polymerized composition.

"primary particle size" refers to the size of a non-associated single crystal zirconia particle. X-ray Diffraction (XRD) is typically used to measure the primary particle size using the techniques described herein.

"sol" refers to a continuous liquid phase containing discrete particles having sizes in a range from 1 nm to 100 nm.

"stable" in reference to a sol means that no more than 5 weight percent of the particles within the sol precipitate when the sol is stored for at least one week at room temperature (e.g., 20° C. to 25° C.). For example, less than 5 weight percent, less than 4 weight percent, less than 3 weight percent, less than 2 weight percent, less than 1 weight percent, or less than 0.5 weight percent of the particles within the sol precipitate under these storage conditions.

"diafiltration" is a technique that uses ultrafiltration membranes to completely remove, replace, or lower the concentration of salts or solvents from solutions containing organic molecules. The process selectively utilizes permeable (porous) membrane filters to separate the components of solutions and suspensions based on their molecular size.

It is known in the art that when conventional YTZP (yttria stabilized tetragonal) zirconia is in contact with water (including biological fluids containing water) for extended periods of time (which effects can be accelerated using the Hydrolytic Stability Test in the Examples section, below) the phase composition at the surface of the YTZP can change (sometimes referred to as "low temperature degradation"). That is, conventional YTZP does not have good hydrolytic stability. The tetragonal phase transforms partly into to the monoclinic phase which can be accompanied with a roughening of the material surface. For biomedical applications, for example, a zirconia material is desired to exhibit little or no tetragonal to monoclinic transformation under humid conditions (respectively hydrothermal treatment). Further details can be found, for example, in J. Chevalier, L. Gremillard, S. Deville, Annu. Rev. Mater. Res. 2007, 37, 1-32 and J. Chevalier, L. Gremillard, A. Virkar, D. R. Clarke, J. Am. Ceram. Soc., 2009, 92 [9], 1901-1920. Surprisingly, embodiments of crack-free, crystalline metal oxide articles described herein have good hydrolytic stability and pass the Hydrolytic Stability Test in the Examples section, below, even in some embodiments when crack-free, crystalline metal oxide articles described herein are subjected to the 5 hour exposure to saturated steam at 135° C. under a pressure of 0.2 MPa, one, two, three, four, or even at least five additional times.

Exemplary uses of crack-free, crystalline metal oxide articles described herein include optical windows, implants (e.g. tooth implants, artificial hip, and knee joints), and dental articles, especially dental ceramic articles (e.g., restoratives, replacements, inlays, onlays, veneers, full and partial crowns, bridges, implants, implant abutments, copings, anterior fillings, posterior fillings, and cavity liner, and bridge frameworks), and orthodontic appliances (e.g., brackets, buccal tubes, cleats, and buttons). Other applications may include where a combinations of high strength, translucency, high temperature stability, low to no hydrothermal degradation, high refractive index and/or low sintering temperatures are desirable.

DETAILED DESCRIPTION

Sols

Figure 1:
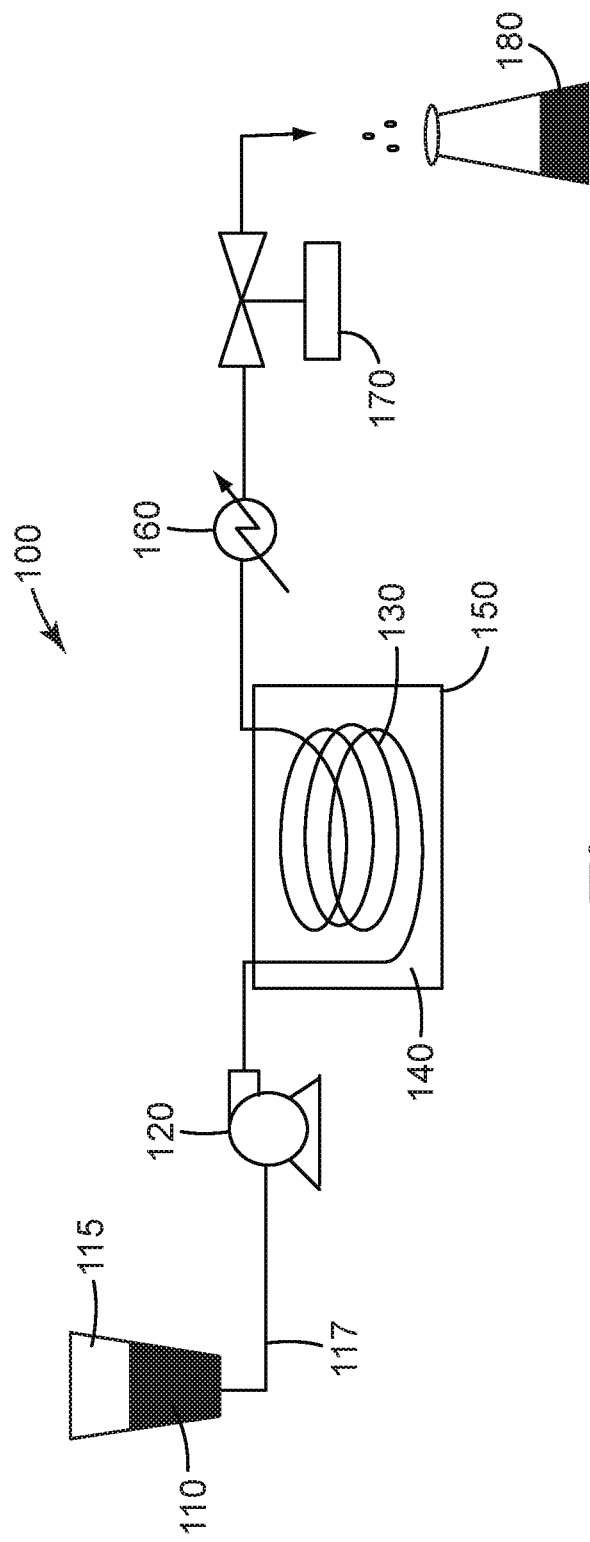
FIG. 1 is an exemplary continuous hydrothermal reactor system.

The zirconia sols are dispersions of zirconia based ceramic particles. The zirconia in the zirconia-based ceramic particles is crystalline, and has been observed to be cubic, tetragonal, monoclinic, or a combination thereof. Because the cubic and tetragonal phases are difficult to differentiate using x-ray diffraction techniques, these two phases are typically combined for quantitative purposes and are referred to as the cubic/tetragonal phase. "Cubic/tetragonal" or "C/T" is used interchangeably to refer to the cubic plus the tetragonal crystalline phases. The percent cubic/tetragonal phase can be determined, for example, by measuring the peak area of the x-ray diffraction peaks for each phase and using Equation (I).

$$\% \ C/T = 100(C/T) \div (C/T + M) \quad (I)$$

In Equation (I), C/T refers to the peak area of the diffraction peak for the cubic/tetragonal phase, M refers to the peak area of the diffraction peak for the monoclinic phase, and % C/T refers to the weight percent cubic/tetragonal crystalline phase. The details of the x-ray diffraction measurements are described more fully in the Example section below.

Typically, at least 50 (in some embodiments, at least 55, 60, 65, 70, 75, 80, 85, 90, or at least 95) weight percent of the zirconia-based particles are present in the cubic or tetragonal crystal structure (i.e., cubic crystal structure, tetragonal crystal structure, or a combination thereof). A greater content of the cubic/tetragonal phase is often desired.

For example, cubic/tetragonal crystals have been observed to be associated with the formation of low aspect ratio primary particles having a cube-like shape when viewed under an electron microscope. This particle shape tends to be relatively easily dispersed into an liquid matrix. Typically, the zirconia particles have an average primary particle size is up to 50 nm (in some embodiments, up to 40 nm, 30 nm, 25 nm, 20 nm, or even up to 15 nm), although larger sizes may also be useful. The average primary particle size, which refers to the non-associated particle size of the zirconia particles, can be determined by x-ray diffraction as described in the Example section. Zirconia sols described herein typically have primary particle size in a range of from 2 nm to 50 nm (in some embodiments, 5 nm to 50 nm, 2 nm to 25 nm, 5 nm to 25 nm, 2 nm to 15 nm, or even 5 nm to 15 nm).

In some embodiments, the particles in the sol are non-associated. In some embodiments, the particles are aggregated or agglomerated to a size up to 500 nm. The extent of association between the primary particles can be determined from the volume-average particle size. The volume-average particle size can be measured using Photon Correlation Spectroscopy as described in more detail in the Examples section below. Briefly, the volume distribution (percentage of the total volume corresponding to a given size range) of the particles is measured. The volume of a particle is proportional to the third power of the diameter. The volume-average size is the size of a particle that corresponds to the mean of the volume distribution. If the zirconia-based particles are associated, the volume-average particle size provides a measure of the size of the aggregates and/or agglomerates of primary particles. If the particles of zirconia are non-associated, the volume-average particle size provides a measure of the size of the primary particles. The zirconia-based particles typically have a volume-average size of up to 100 nm (in some embodiments, up to 90 nm, 80 nm, 75 nm, 70 nm, 60 nm, 50 nm, 40 nm, 30 nm, 25 nm, 20 nm, or even up to 15 nm).

A quantitative measure of the degree of association between the primary particles in the zirconia sol is the dispersion index. As used herein the "dispersion index" is defined as the volume-average particle size divided by the primary particle size. The primary particle size (e.g., the weighted average crystallite size) is determined using x-ray diffraction techniques and the volume-average particle size is determined using Photon Correlation Spectroscopy. As the association between primary particles decreases, the dispersion index approaches a value of 1 but can be somewhat higher or lower. The zirconia-based particles typically have a dispersion index in a range of from 1 to 7 (in some embodiments, 1 to 5, 1 to 4, 1 to 3, 1 to 2.5, or even 1 to 2).

Photon Correlation Spectroscopy also can be used to calculate the Z-average primary particle size. The Z-average size is calculated from the fluctuations in the intensity of scattered light using a cumulative analysis and is proportional to the sixth power of the particle diameter. The volume-average size will typically be a smaller value than the Z-average size. The zirconia particles tend to have a Z-average size that is up to 100 nanometers (in some embodiments, up to 90 nm, 80 nm, 70 nm, 60 nm, 50 nm, 40 nm, 35 nm, or even up to 30 nm).

Depending on how the zirconia-based particles are prepared, the particles may contain at least some organic material in addition to the inorganic oxides. For example, if the particles are prepared using a hydrothermal approach, there may be some organic material attached to the surface of the zirconia-based particles. Although not wanting to be bound by theory, it is believed that organic material originates from the carboxylate species (anion, acid, or both) included in the feedstock or formed as a byproduct of the hydrolysis and condensation reactions (i.e., organic material is often absorbed on the surface of the zirconia-based particles). For example, in some embodiments, the zirconia-based particles contain up to 15 (in some embodiments, up to 12, 10, 8, or even up to 6) weight percent organic material, based on the weight of the particles.

Although any of a variety of known methods can be used to provide the zirconia-based particles, preferably they are prepared using hydrothermal technology. In one exemplary embodiment, the zirconia-based sols are prepared by hydrothermal treatment of aqueous metal salt (e.g., a zirconium salt, an yttrium salt, and an optional lanthanide element salt or aluminum salt) solutions, suspensions or a combination of them.

The aqueous metal salts, which are selected to be soluble in water, are typically dissolved in the aqueous medium. The aqueous medium can be water or a mixture of water with other water soluble or water miscible materials. In addition, the aqueous metal salts and other water soluble or water miscible materials which may be present are typically selected to be removable during subsequent processing steps and to be non-corrosive.

At least a majority of the dissolved salts in the feedstock are usually carboxylate salts rather than halide salts, oxyhalide salts, nitrate salts, or oxynitrate salts. Although not wanting to be bound by theory, it is believed that halide and nitrate anions in the feedstock tend to result in the formation of zirconia-based particles that are predominately of a monoclinic phase rather than the more desirable tetragonal or cubic phases. Further, carboxylates and/or acids thereof tend to be more compatible with an organic matrix material compared to halides and nitrates. Although any carboxylate anion can be used, the carboxylate anion often has no greater than 4 carbon atoms (e.g., formate, acetate, propionate, butyrate, or a combination thereof). The dissolved salts are often acetate salts. The feedstock can further include, for example, the corresponding carboxylic acid of the carboxylate anion. For example, feedstocks prepared from acetate salts often contain acetic acid.

One exemplary zirconium salt is zirconium acetate salt, represented by a formula such as $ZrO_{((4-n/2)}{}^{n+}(CH_3COO^-)_n$, where n is in the range from 1 to 2. The zirconium ion may be present in a variety of structures depending, for example, on the pH of the feedstock. Methods of making zirconium acetate are described, for example, in W. B. Blumenthal, "The Chemical Behavior of Zirconium," pp. 311-338, D. Van Nostrand Company, Princeton, N.J. (1958). Suitable aqueous solutions of zirconium acetate are commercially available, for example, from Magnesium Elektron, Inc., Flemington, N.J., that contain, for example, up to 17 weight percent zirconium, up to 18 weight percent zirconium, up to 20 weight percent, up to 22 weight percent, up to 24 weight percent, up to 26 weight percent, and up to 28 weight percent zirconium, based on the total weight of the solution.

Similarly, exemplary yttrium salts, lanthanide element salts, and aluminum salts often have a carboxylate anion, and are commercially available. Because these salts are typically used at much lower concentration levels than the zirconium salt, however, salts other than carboxylate salts (e.g., acetate salts) may also be useful (e.g., nitrate salts).

The total amount of the various salts dissolved in the feedstock can be readily determined based on the total percent solids selected for the feedstock. The relative amounts of the various salts can be calculated to provide the selected composition for the zirconia-based particles.

Typically, the pH of the feedstock is acidic. For example, the pH is usually less than 6, less than 5, or even less than 4 (in some embodiments, in a range from 3 to 4).

The liquid phase of the feedstock is typically predominantly water (i.e., the liquid phase is an aqueous based medium). Preferably, the water is deionized to minimize the introduction of alkali metal ions, alkaline earth ions, or both into the feedstock. Optionally, water-miscible organic co-solvents are included in the liquid phase in amounts, for example, up 20 weight percent, based on the weight of the liquid phase. Suitable co-solvents include 1-methoxy-2-propanol, ethanol, isopropanol, ethylene glycol, N,N-dimethylacetamide, and N-methyl pyrrolidone.

Although, the feedstock typically is a solution and does not contain dispersed or suspended solids (e.g., seed particles usually are not present in the feedstock), the feedstock often contains greater than 5 (in some embodiments, greater than 10, 11, 12, 13, 14, 15, or up to 19, 20, 21, 22, 23, 24, or 25; in some embodiments, in a range from 10 to 25, 12 to 22, 14 to 20 weight percent, or even 15 to 19) weight percent solids and these solids are typically dissolved. As used herein, the "weight percent solids" is calculated by drying a sample at 120° C., and refers the portion of the feedstock that is not water, a water-miscible co-solvent, or another compound that can be vaporized at temperatures up to 120° C. The weight percent solids is equal to $$100 \text{ (dry weight)} \div \text{(wet weight)}.$$

In this equation, the term "wet weight" refers to the weight of a feedstock sample before drying and the term "dry weight" refers to the weight of the sample after drying, for example, at 120° C. for at least 30 minutes. When subjected to hydrothermal treatment, the various dissolved salts in the feedstock undergo hydrolysis and condensation reactions to form the zirconia-based particles. These reactions are often accompanied with the release of an acidic byproduct. That is, the byproduct is often one or more carboxylic acids corresponding to the zirconium carboxylate salt plus any other carboxylate salt in the feedstock. For example, if the salts are acetate salts, acetic acid is formed as a byproduct of the hydrothermal reaction.

Any suitable hydrothermal reactor can be used for the preparation of the zirconia-based particles. The reactor can be a batch or continuous reactor. The heating times are typically shorter and the temperatures are typically higher in a continuous hydrothermal reactor compared to a batch hydrothermal reactor. The time of the hydrothermal treatments can be varied depending, for example, on the type of reactor, the temperature of the reactor, and the concentration of the feedstock. The pressure in the reactor can be autogeneous (i.e., the vapor pressure of water at the temperature of the reactor), can be hydraulic (i.e., the pressure caused by the pumping of a fluid against a restriction), or can result from the addition of an inert gas such as nitrogen or argon. Suitable batch hydrothermal reactors are available, for example, from Parr Instruments Co., Moline, Ill. Some suitable continuous hydrothermal reactors are described, for example, in U.S. Pat. No. 5,453,262 (Dawson et al.) and U.S. Pat. No. 5,652,192 (Matson et al.); Adschiri et al., *J. Am. Ceram. Soc.*, 75, 1019-1022 (1992); and Dawson, *Ceramic Bulletin*, 67 (10), 1673-1678 (1988).

If a batch reactor is used to form the zirconia-based particles, the temperature is often in a range from 160° C. to 275° C. (in some embodiments, 160° C. to 250° C., 170° C. to 250° C., 175° C. to 250° C., 200° C. to 250° C., 175° C. to 225° C., 180° C. to 220° C., 180° C. to 215° C., or even, for example, 190° C. to 210° C.). Typically, the feedstock is typically placed in the batch reactor at room temperature. The feedstock within the batch reactor is heated to the designated temperature and held at that temperature for at least 30 minutes (in some embodiments, at least 1 hour, at least 2 hours, or even at least 4 hours), and up to 24 hours), (in some embodiments, up to 20 hours, up to 16 hours, or up to 8 hours). For example, the temperature can be held in the range from 0.5 to 24 hours (in some embodiments, in the range from 1 to 18 hours, 1 to 12 hours, or even 1 to 8 hours). Any of a variety sized batch reactor can be used. For example, the volume of the batch reactor can be in a range from several milliliters to several liters or more.

In some embodiments, the feedstock is passed through a continuous hydrothermal reactor. As used herein, the term "continuous" with reference to the hydrothermal reactor system means that the feedstock is continuously introduced and an effluent is continuously removed from the heated zone. The introduction of feedstock and the removal of the effluent typically occur at different locations of the reactor. The continuous introduction and removal can be constant or pulsed.

One exemplary continuous hydrothermal reactor system 100 is shown schematically in FIG. 1. Feedstock 110 is contained within feedstock tank 115. Feedstock tank 115 is connected with tubing or piping 117 to pump 120. Similar tubing or piping can be used to connect other components of the tubular reactor system. Tubing or piping 117 can be constructed of any suitable material such as metal, glass, ceramic, or polymer. Tubing or piping 117 can be, for example, polyethylene tubing or polypropylene tubing in the portions of continuous hydrothermal reactor system 100 that are not heated and that are not under high pressure. Any tubing that is heated or under pressure is often made of metal (e.g., stainless steel, carbon steel, titanium, nickel, or the like) or has a metal outer housing. Pump 120 is used to introduce feedstock 110 into tubular reactor 130. That is, pump 120 is connected to the inlet of tubular reactor 130. Any type of pump 120 can be used that is capable of pumping against the pressure within tubular reactor 130. The pump can provide a constant or pulsed flow of the feedstock solution into tubular reactor 130.

As used herein, the term "tubular reactor" refers to the portion of the continuous hydrothermal reactor system that is heated (i.e., the heated zone). Although tubular reactor 130 is shown in FIG. 1 as a coil of tubing, the tubular reactor can be in any suitable shape. The shape of the tubular reactor is often selected based on the desired length of the tubular reactor and the method used to heat the tubular reactor. For example, the tubular reactor can be straight, U-shaped, or coiled. The interior portion of the tubular reactor can be empty or can contain baffles, balls, or other known mixing techniques.

As shown in FIG. 1, tubular reactor 130 is placed in heating medium 140 within heating medium vessel 150. Heating medium 140 can be, for example, an oil, sand, salt, or the like, that can be heated to a temperature above the hydrolysis and condensation temperatures of the zirconium. Suitable oils include plant oils (e.g., peanut oil and canola oil). Some plant oils are preferably kept under nitrogen when heated to prevent or minimize oxidation of the oils. Other suitable oils include polydimethylsiloxanes such as those commercially available from Duratherm Extended Fluids, Lewiston, N.Y., under the trade designation "DURATHERM S". Suitable salts include, for example, sodium nitrate, sodium nitrite, potassium nitrate, or mixtures thereof. Heating medium vessel 150 can be any suitable container that can hold the heating medium and that can withstand the heating temperatures used for tubular reactor 130. Heating medium vessel 150 can be heated using any suitable means. In many embodiments, heating medium vessel 150 is positioned inside an electrically heated coil. Other types of heaters that can be used in place of heating vessel 150 and/or heating medium 140 include induction heaters, microwave heaters, fuel-fired heaters, heating tape, and steam coils.

Tubular reactor 130 can be made of any material capable of withstanding the temperatures and pressures used to prepare zirconia particles. Tubular reactor 130 preferably is constructed of a material that can resist dissolution in an acidic environment. For example, carboxylic acids can be present in the feedstock or can be produced as a reaction byproduct within the continuous hydrothermal reactor system. In some exemplary embodiments, the tubular reactor is made of stainless steel, nickel, titanium, or carbon-based steel.

In other exemplary embodiments, an interior surface of the tubular reactor contains a fluorinated polymeric material. This fluorinated polymeric material can include a fluorinated polyolefin. In some embodiments, the polymeric material is polytetrafluoroethylene (PTFE) such as that available under the trade designation "TEFLON" from DuPont, Wilmington, Del. Some tubular reactors have a PTFE hose within a metal housing such as a braided stainless steel housing. These carboxylic acids can leach metals from some known hydrothermal reactors such as those constructed of stainless steel.

The second end of tubular reactor 130 is usually connected to cooling device 160. Any suitable cooling device 160 can be used. In some embodiments, cooling device 160 is a heat exchanger that includes a section of tubing or piping that has an outer jacket filled with a cooling medium such as cool water. In other embodiments, cooling device 160 includes a coiled section of tubing or piping that is placed in a vessel that contains cooling water. In either of these embodiments, the tubular reactor effluent is passed through the section of tubing and is cooled from the tubular reactor temperature to a temperature no greater than 100° C. (in some embodiments, no greater than 80° C., 60° C., or even no greater than 40° C.). Other cooling devices that contain dry ice or refrigeration coils can also be used. After cooling, the reactor effluent can be discharged into product collection vessel 180. The reactor effluent is preferably not cooled below the freezing point prior to being discharged into product collection vessel 180.

The pressure inside the tubular reactor can be at least partially controlled with backpressure valve 170, which is generally positioned between cooling device 160 and sample collection vessel 180. Backpressure valve 170 controls the pressure at the exit of continuous hydrothermal reactor system 100 and helps to control the pressure within tubular reactor 130. The backpressure is often at least 100 pounds per square inch (0.7 MPa) (in some embodiments, at least 200 pounds per square inch (1.4 MPa), 300 pounds per square inch (2.1 MPa), 400 pounds per square inch (2.8 MPa), 500 pounds per square inch (3.5 MPa), 600 pounds per square inch (4.2 MPa), or even at least 700 pounds per square inch (4.9 MPa). The backpressure should be high enough to prevent boiling within the tubular reactor.

The dimensions of tubular reactor 130 can be varied and, in conjunction with the flow rate of the feedstock, can be selected to provide suitable residence times for the reactants within the tubular reactor. Any suitable length tubular reactor can be used provided that the residence time and temperature are sufficient to convert the zirconium in the feedstock to zirconia-based particles. The tubular reactor often has a length of at least 0.5 meter (in some embodiments, at least 1 meter, 2 meters, 5 meters, 10 meters, 15 meters, 20 meters, 30 meters, 40 meters, or even at least 50 meters). The length of the tubular reactor in some embodiments is less than 500 meters (in some embodiments, less than 400 meters, 300 meters, 200 meters, 100 meters, 80 meters, 60 meters, 40 meters, or even less than 20 meters).

Tubular reactors with a relatively small inner diameter are typically preferred. For example, tubular reactors having an inner diameter no greater than about 3 centimeters are often used because of the fast rate of heating of the feedstock that can be achieved with these reactors. Also, the temperature gradient across the tubular reactor is less for reactors with a smaller inner diameter compared to those with a larger inner diameter. The larger the inner diameter of the tubular reactor, the more this reactor resembles a batch reactor. However, if the inner diameter of the tubular reactor is too small, there is an increased likelihood of the reactor becoming plugged or partially plugged during operation resulting from deposition of material on the walls of the reactor. The inner diameter of the tubular reactor is often at least 0.1 cm (in some embodiments, at least 0.15 cm, 0.2 cm, 0.3 cm, 0.4 cm, 0.5 cm, or even at least 0.6 cm). In some embodiments, the diameter of the tubular reactor is no greater than 3 cm (in some embodiments, no greater than 2.5 cm, 2 cm, 1.5 cm, or even greater than 1 centimeter; in some embodiments, in a range from 0.1 to 2.5 cm, 0.2 cm to 2.5 cm, 0.3 cm to 2 cm, 0.3 cm to 1.5 cm, or even 0.3 cm to 1 cm).

In a continuous hydrothermal reactor, the temperature and the residence time are typically selected in conjunction with the tubular reactor dimensions to convert at least 90 mole percent of the zirconium in the feedstock to zirconia-based particles using a single hydrothermal treatment. That is, at least 90 mole percent of the dissolved zirconium in the feedstock is converted to zirconia-based particles within a single pass through the continuous hydrothermal reactor system.

Alternatively, for example, a multiple step hydrothermal process can be used. For example, the feedstock can be subjected to a first hydrothermal treatment to form a zirconium-containing intermediate and a by-product such as a carboxylic acid. A second feedstock can be formed by removing at least a portion of the by-product of the first hydrothermal treatment from the zirconium-containing intermediate. The second feedstock can then be subjected to a second hydrothermal treatment to form a sol containing the zirconia-based particles. Further details on this process are described, for example, in U.S. Pat. No. 7,241,437 (Davidson et al.).

If a two step hydrothermal process is used, the percent conversion of the zirconium-containing intermediate is typically in a range from 40 to 75 mole percent. The conditions used in the first hydrothermal treatment can be adjusted to provide conversion within this range. Any suitable method can be used to remove at least part of the by-product of the first hydrothermal treatment. For example, carboxylic acids such as acetic acid can be removed by a variety of methods such as vaporization, dialysis, ion exchange, precipitation, and filtration.

When referring to a continuous hydrothermal reactor, the term "residence time" means the average length of time that the feedstock is within the heated portion of the continuous hydrothermal reactor system. For the reactor depicted in FIG. 1, the residence time is the average time the feedstock is within tubular reactor 130 and is equal to the volume of the tubular reactor divided by the flow rate of the feedstock through the tubular reactor. The residence time in the tubular reactor can be varied by altering the length or diameter of the tubular reactor as well as by altering the flow rate of the feedstock. In some embodiments, the residence time is at least 1 minute (in some embodiments, at least 2 minutes, 4 minutes, 6 minutes, 8 minutes, or even at least 10 minutes), is typically no greater than 240 minutes (in some embodiments, no greater than 180 minutes, 120 minutes, 90 minutes, 60 minutes, 45 minutes, or even no greater than 30 minutes. In some embodiments, the residence time is in the range from 1 to 240 minutes, 1 to 180 minutes, 1 to 120 minutes, 1 to 90 minutes, 1 to 60 minutes, 10 to 90 minutes, 10 to 60 minutes, 20 to 60 minutes, or even 30 to 60 minutes.

Any suitable flow rate of the feedstock through the tubular reactor can be used as long as the residence time is sufficiently long to convert the dissolved zirconium to zirconia-based particles. That is, the flow rate is often selected based on the residence time needed to convert the zirconium in the feedstock to zirconia-based particles. Higher flow rates are desirable for increasing throughput and for minimizing the deposition of materials on the walls of the tubular reactor. A higher flow rate can often be used when the length of the reactor is increased or when both the length and diameter of the reactor are increased. The flow through the tubular reactor can be either laminar or turbulent.

In some exemplary continuous hydrothermal reactors, the reactor temperature is in the range from 170° C. to 275° C., 170° C. to 250° C., 170° C. to 225° C., 180° C. to 225° C., 190° C. to 225° C., 200° C. to 225° C., or even 200° C. to 220° C. If the temperature is greater than about 275° C., the pressure may be unacceptably high for some hydrothermal reactors systems. However, if the temperature is less than about 170° C., the conversion of the zirconium in the feedstock to zirconia-based particles may be less than 90 weight percent using typical residence times.

The effluent of the hydrothermal treatment (i.e., the product of the hydrothermal treatment) is a zirconia-based sol. The sol contains at least 3 weight percent zirconia-based particles dispersed, suspended, or a combination thereof in an aqueous medium. In some embodiments, the zirconia-based particles can contain (a) 0 to 5 mole percent of a lanthanide element oxide, based on total moles of inorganic oxide in the zirconia-based particles, and (b) 1 to 15 mole percent yttrium oxide, based on total moles of inorganic oxide in the zirconia-based particles. The zirconia-based particles are crystalline and have an average primary particle size no greater than 50 nanometers. In some embodiments, cerium oxide, magnesium oxide, ytterbium oxide, and/or calcium oxide may be used with or in place of the yttria.

The sol effluent of the hydrothermal treatment usually contains non-associated zirconia-based particles. The effluent is typically clear or slightly cloudy. By contrast, zirconia-based sols that contain agglomerated or aggregated particles usually tend to have a milky or cloudy appearance. The zirconia-based sols often have a high optical transmission due to the small size and non-associated form of the primary zirconia particles in the sol. High optical transmission of the sol can be desirable in the preparation of transparent or translucent composite materials. As used herein, "optical transmission" refers to the amount of light that passes through a sample (e.g., a zirconia-based sol) divided by the total amount of light incident upon the sample. The percent optical transmission may be calculated using the equation $$100 \, (I/I_o)$$

where I is the light intensity passing though the sample and $I_o$ is the light intensity incident on the sample. The optical transmission may be determined using an ultraviolet/visible spectrophotometer set at a wavelength of 600 nanometers with a 1 centimeter path length. The optical transmission is a function of the amount of zirconia in a sol. For zirconia-based sols having about 1 weight percent zirconia, the optical transmission is typically at least 70 percent (in some embodiments, at least 80 percent, even or at least 90 percent). For zirconia-based sols having about 10 weight percent zirconia, the optical transmission is typically at least 20 percent (in some embodiments, at least 50 percent, or even at least 70 percent).

In some embodiments, at least a portion of the aqueous-based medium is removed from the zirconia-based sol. Any known means for removing the aqueous-based medium can be used. This aqueous-based medium contains water and often contains dissolved carboxylic acids and/or anions thereof that are present in the feedstock or that are byproducts of the reactions that occur within the hydrothermal reactor. As used herein, the term "carboxylic acids and/or anions thereof" refers to carboxylic acids, carboxylate anions of these carboxylic acids, or mixtures thereof. The removal of at least a portion of these dissolved carboxylic acids and/or anions thereof from the zirconia-based sol may be desirable in some embodiments. The zirconia-based sol can be subjected, for example, to at least one of vaporization, drying, ion exchange, solvent exchange, diafiltration, or dialysis, for example, for concentrating, removal of impurities or to compatibilize with other components present in the sol.

In some embodiments, the zirconia sol (prepared from hydrothermal process or other processes) is concentrated. Along with removing at least a portion of the water present in the effluent, the concentration or drying process often results in the vaporization of at least a portion of the dissolved carboxylic acids.

In other embodiments, for example, the zirconia based sol can be subjected to dialysis or diafiltration. Dialysis and diafiltration both tend to remove at least a portion of the dissolved carboxylic acids and/or anions thereof. For dialysis, a sample of the effluent can be positioned within a membrane bag that is closed and then placed within a water bath. The carboxylic acid and/or carboxylate anions diffuse out of the sample within the membrane bag. That is, these species will diffuse out of the effluent through the membrane bag into the water bath to equalize the concentration within the membrane bag to the concentration in the water bath. The water in the bath is typically replaced several times to lower the concentration of species within the bag. A membrane bag is typically selected that allows diffusion of the carboxylic acids and/or anions thereof but does not allow diffusion of the zirconia-based particles out of the membrane bag.

For diafiltration, a permeable membrane is used to filter the sample. The zirconia particles can be retained by the filter if the pore size of the filter is appropriately chosen. The dissolved carboxylic acids and/or anions thereof pass through the filter. Any liquid that passes through the filter is replaced with fresh water. In a discontinuous diafiltration process, the sample is often diluted to a pre-determined volume and then concentrated back to the original volume by ultrafiltration. The dilution and concentration steps are repeated one or more times until the carboxylic acid and/or anions thereof are removed or lowered to an acceptable concentration level. In a continuous diafiltration process, which is often referred to as a constant volume diafiltration process, fresh water is added at the same rate that liquid is removed through filtration. The dissolved carboxylic acid and/or anions thereof are in the liquid that is removed.

While the majority of the yttrium and lanthanum, if present, are incorporated into the crystalline zirconia particles there is a fraction of these metals that can be removed during the diafiltration or dialysis process. The actual composition of a sol after diafiltration may be different than that before dialysis. For example, a sol produced with a 97.5:2.3:2 $ZrO_2$:$Y_2O_3$:$La_2O_3$ composition was observed to result in a sol with the composition 96.6:2.2:1.3 $ZrO_2$:$Y_2O_3$:$La_2O_3$ after the dialysis. In another example, a sol prepared with a 88:12 $ZrO_2$/$Y_2O_3$ composition was observed to result in a sol with the composition 90.7:9.3 $ZrO_2$/$Y_2O_3$ after the dialysis. The actual composition of the final sol and composites made from these can be calculated from these data and rule of mixtures.

A zirconia based sol comprises zirconia-based particles dispersed and/or suspended (i.e., dispersed, suspended, or a combination thereof) in an aqueous/organic matrix. In some embodiments, the zirconia-based particles can be dispersed and/or suspended in the organic matrix without any further surface modification. The organic matrix can be added directly to zirconia based sol. Also, for example, the organic matrix can be added to the zirconia based sol after treatment to remove at least some of the water, after treatment to remove at least some of the carboxylic acids and/or anions thereof, or after both treatments. The organic matrix that is added is often contains a polymerizable composition that is subsequently polymerized and/or crosslinked to form a gel.

In some embodiments, the zirconia based sol can be subjected to a solvent exchange process. An organic solvent having a higher boiling point than water can be added to the effluent. Examples of organic solvents that are suitable for use in a solvent exchange method include 1-methoxy-2-propanol and N-methyl pyrrolidone. The water then can be removed by a method such as distillation, rotary evaporation, or oven drying. Depending on the conditions used for removing the water, at least a portion of the dissolved carboxylic acid and/or anion thereof can also be removed. Other organic matrix material can be added to the treated effluent (i.e., other organic matrix material can be added to the zirconia-based particle suspended in the organic solvent used in the solvent exchange process).

In some embodiments, the zirconia-based sols are treated with a surface modification agent to improve compatibility with the organic matrix material. Surface modification agents may be represented by the formula A-B, where the A group is capable of attaching to the surface of a zirconia-based particle and B is a compatibility group. Group A can be attached to the surface by adsorption, formation of an ionic bond, formation of a covalent bond, or a combination thereof. Group B can be reactive or nonreactive and often tends to impart characteristics to the zirconia-based particles that are compatible (i.e., miscible) with an organic solvent, with another organic matrix material (e.g., monomer, oligomers, or polymeric material), or both. For example, if the solvent is non-polar, group B is typically selected to be non-polar as well. Suitable B groups include linear or branched hydrocarbons that are aromatic, aliphatic, or both aromatic and aliphatic. The surface modifying agents include carboxylic acids and/or anions thereof, sulfonic acids and/or anions thereof, phosphoric acids and/or anions thereof, phosphonic acids and/or anions thereof, silanes, amines, and alcohols. Suitable surface modification agents are further described, for example, in PCT Application Publication WO 2009/085926 (Kolb et al.), the disclosure of which is incorporated herein by reference.

A surface modification agent can be added to the zirconia-based particles using conventional techniques. The surface modification agent can be added before or after any removal of at least a portion of the carboxylic acids and/or anions thereof from the zirconia-based sol. The surface modification agent can be added before or after removal of the water from the zirconia-based sol. The organic matrix can be added before or after surface modification or simultaneously with surface modification. Various methods of adding the surface modification agent are further described, for example, in WO 2009/085926 (Kolb et al.), the disclosure of which is incorporated herein by reference.

The surface modification reactions can occur at room temperature (e.g., 20° C. to 25° C.) or at an elevated temperature (e.g., up to about 95° C.). When the surface modification agents are acids such as carboxylic acids, the zirconia-based particles typically can be surface-modified at room temperature. When the surface modification agents are silanes, the zirconia-based particles are typically surface modified at elevated temperatures.

The organic matrix typically includes a polymeric material or a precursor to a polymeric material such as a monomer or an oligomer having a polymerizable group and a solvent. The zirconia-based particles can be combined with the organic matrix using conventional techniques. For example, if the organic matrix is a precursor to a polymeric material, the zirconia-based particles can be added prior to the polymerization reaction. The composite material containing a precursor of a polymeric material is often shaped before polymerization.

Representative examples of monomers include (meth)acrylate-based monomers, styrene-based monomers, and epoxy-based monomers. Representative examples of reactive oligomers include, polyesters having (meth)acrylate groups, polyurethanes having (meth)acrylate groups, polyethers having (meth)acrylate groups, or acrylics. Representative examples of polymeric material include polyurethanes, poly(meth)acrylates, and polystyrenes.

Gels

The zirconia based sols are typically solidified by gelation. Preferably, the gelation process allows large gels to be formed without cracks and gels that can be further processed without inducing cracks. For example, preferably, the gelation process leads to a gel having a structure that will not collapse when the solvent is removed. The gel structure is compatible with and stable in a variety of solvents and conditions that may be necessary for supercritical extraction. Furthermore, the gel structure needs to be compatible with supercritical extraction fluids (e.g., supercritical $CO_2$). In other words, the gels should be stable and strong enough to withstand drying, so as to produce stable gels and give materials that can be heated to burn out the organics, pre-sintered, and densified without inducing cracks. Preferably, the resulting gels have relatively small and uniform pore size to aid in sintering them to high density at low sintering temperatures. However, preferably the pores of the gels are large enough to allow product gases of organic burnout escape without leading to cracking of the gel. Furthermore, the gelation step allows control of the density of the resulting gels aids in the subsequent processing of the gel such as supercritical extraction, organic burnout, and sintering. It is preferable that the gel contain the minimum amount of organic material or polymer modifiers.

The gels described herein contain zirconia-based particles. In some embodiments, the gels contain at least two types of zirconia-based particles varying in crystalline phases, composition, or particle size. We have found, particulate based gels can lead to less shrinkage compared to gels produced form alkoxides which undergo significant and complicated condensation and crystallization reactions during further processing. The crystalline nature allows combinations of different crystal phases on a nanoscale. Applicants have observed that formation of a gel thru polymerization of these reactive particles yield strong, resilient gels. Applicants have also found that the use of mixtures of sols with crystalline particles can allow formation of stronger and more resilient gels for further processing. For example, Applicants observed that a gel comprising a mixture of cubic and tetragonal zirconia particles was less susceptible to cracking during supercritical extraction and organic burnout steps.

The gels comprise organic material and crystalline metal oxide particles, wherein the crystalline metal oxide particles are present in a range from 3 to 20 volume percent, based on the total volume of the gel, wherein at least 70 (in some embodiments, at least 75, 80, 85, 90, 95, 96, 97, 98, or even at least 99; in a range from 70 to 99, 75 to 99, 80 to 99, or even 85 to 99) mole percent of the crystalline metal oxide is $ZrO_2$. Optionally, the gels may also include amorphous non-crystalline oxide sources.

In some embodiments, gels described herein, the crystalline metal oxide particles have an average primary particle size in a range from 5 nanometers to 50 nanometers (in some embodiments, in a range from 5 nanometers to 25 nanometers, 5 nanometers to 15 nanometers, or even from 5 nanometers to 10 nanometers). Typically, the average primary particle size is measured by using the X-Ray Diffraction technique. Preferably, the particles are not agglomerated but, it is possible that particles with some degree of aggregation may also be useful.

Exemplary sources of the $ZrO_2$, $Y_2O_3$, $La_2O_3$, and $Al_2O_3$ include crystalline zirconia based sols prepared by any suitable means. The sols described above are particularly well suited. The $Y_2O_3$, $La_2O_3$, and $Al_2O_3$, can be present in the zirconia based particles, and/or present as separate colloidal particles or soluble salts.

In some embodiments, for gels described herein the crystalline metal oxide particles comprise a first plurality of particles, and a second, different plurality of particles (i.e., is distinguishable by average composition, phase(s), microstructure, and/or size).

Typically, gels described herein have an organic content that is at least 3 (in some embodiments, at least 4, 5, 10, 15, or even at least 20) percent by weight, based on the total weight of the gel. In some embodiments, gels described herein have an organic content in a range from 3 to 30, 10 to 30, or even 10 to 20, percent by weight, based on the total weight of the gel.

Optionally, gels described herein comprise at least one of $Y_2O_3$ (e.g., in a range from 1 to 15, 1 to 9, 1 to 5, 6 to 9, 3.5 to 4.5, or even 7 to 8 mole percent of the crystalline metal oxide is $Y_2O_3$), $La_2O_3$ (e.g., up to 5 mole percent $La_2O_3$), or $Al_2O_3$ (e.g., up to 0.5 mole percent $Al_2O_3$). In one exemplary gel the crystalline metal oxide comprises in a range from 1 to 5 mole percent $Y_2O_3$, and in a range from 0 to 2 mole percent $La_2O_3$, and in a range from 93 to 97 mole percent $ZrO_2$. In another exemplary gel the crystalline metal oxide comprises in a range from 6 to 9 mole percent $Y_2O_3$, and in a range from 0 to 2 mole percent $La_2O_3$, and in a range from 89 to 94 mole percent $ZrO_2$. In another exemplary gel the crystalline metal oxide comprises in a range from 3.5 to 4.5 mole percent $Y_2O_3$, and in a range from 0 to 2 mole percent $La_2O_3$, and in a range from 93.5 to 96.5 mole percent $ZrO_2$. In another exemplary gel the crystalline metal oxide comprises in a range from 7 to 8 mole percent $Y_2O_3$, and in a range from 0 to 2 mole percent $La_2O_3$, and in a range from 90 to 93 mole percent $ZrO_2$. Other optional oxides that may be present in gels described herein include at least one of $CeO_2$, $Pr_2O_3$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Tm_2O_3$, $Yb_2O_3$, $Fe_2O_3$, $MnO_2$, $Co_2O_3$, $Cr_2O_3$, $NiO$, $CuO$, $Bi_2O_3$, $Ga_2O_3$, or $Lu_2O_3$. Additives that may add desired coloring to the resulting crack free crystalline metal oxide articles include at least one of $Fe_2O_3$, $MnO_2$, $Co_2O_3$, $Cr_2O_3$, $NiO$, $CuO$, $Bi_2O_3$, $Ga_2O_3$, $Er_2O_3$, $Pr_2O_3$, $Eu_2O_3$, $Dy_2O_3$, $Sm_2O_3$, $V_2O_5$, $W_2O_5$ or $CeO_2$. In some embodiments, the amount of optional oxide(s) is in an amount in a range from about 10 ppm to 20,000 ppm. In some embodiments, it is desirable to have sufficient oxides present to so the crack free crystalline metal oxide articles has coloring of a tooth.

One exemplary method for making gels described herein comprises providing a first zirconia sol comprising crystalline metal oxide particles having an average primary particle size of not greater than 15 nanometers (in some embodiments, in a range from 5 nanometers to 15 nanometers), wherein at least 70 (in some embodiments, at least 75, 80, 85, 90, 95, 96, 97, 98, or even at least 99; in a range from 70 to 99, 75 to 99, 80 to 99, or even 85 to 99) mole percent of the crystalline metal oxide is $ZrO_2$. The sol is optionally concentrated to provide a concentrated zirconia sol. A co-solvent, surface modifiers and optional monomers are added while stirring to obtain a well dispersed sol. Also, a radical initiator (e.g., ultraviolet (UV) or thermal initiator) is added to the radically polymerizable surface-modified zirconia sol. The resulting sol is optionally purged with $N_2$ gas to remove oxygen. The resulting sol can be gelled by radiating with actinic or heating at at least one temperature for a time sufficient to polymerize the radically surface-modified zirconia sol comprising the radical initiator to form a gel. Typically the resulting gel is a strong, translucent gel.

In some embodiments the sols for making aerogels described herein comprise zirconia based particles that are surface modified with a radically polymerizable surface treatment agent/modifier. The sol can be gelled, for example, by radical (thermal initiation or light initiation) polymerization. Exemplary radically polymerizable surface modifiers include acrylic acid, methacrylic acid, beta-carboxyethyl acrylate, and mono-2-(methacryloxyethyl)succinate. An exemplary modification agent for imparting both polar character and reactivity to the zirconia-containing nanoparticles is mono(methacryloxypolyethyleneglycol) succinate. Exemplary polymerizable surface modifiers can be can reaction products of hydroxyl containing polymerizable monomers with cyclic anhydrides such as succinic anhydride, maleic anhydride and pthalic anhydride. Exemplary polymerization hydroxyl containing monomers include hyroxyethyl acrylate, hydroxyethyl methacrylate, hydoxypropyl acrylate, hydoxyproyl methacrylate, hydroxyl butyl acrylate, and hydroxybutyl methacrylate. Acyloxy and methacryloxy functional polyethylene oxide, and polypropylene oxide may also be used as the polymerizable hydroxyl containing monomers. Exemplary polymerizable silanes include alkyltrialkoxysilanes methacryloxyalkyltrialkoxysilanes or acryloxyalkyltrialkoxysilanes (e.g., 3-methacryloxypropyltrimethoxysilane, 3-acryloxypropyltrimethoxysilane, and 3-(methacryloxy)propyltriethoxysilane; as 3-(methacryloxy)propylmethyldimethoxysilane, and 3-(acryloxypropyl)methyldimethoxysilane); methacryloxyalkyldialkylalkoxysilanes or acyrloxyalkyldialkylalkoxysilanes (e.g., 3-(methacryloxy)propyldimethylethoxysilane); mercaptoalkyltrialkoxylsilanes (e.g., 3-mercaptopropyltrimethoxysilane); aryltrialkoxysilanes (e.g., styrylethyltrimethoxysilane); vinylsilanes (e.g., vinylmethyldiacetoxysilane, vinyldimethylethoxysilane, vinylmethyldiethoxysilane, vinyltrimethoxysilane, vinyltriethoxysilane, vinyltriacetoxysilane, vinyltriisopropoxysilane, vinyltrimethoxysilane, and vinyltris(2-methoxyethoxy)silane).

In some embodiments, sols for making aerogels described herein comprise zirconia-based particles that are surface modified with nonreactive surface modifiers which can impart additional compatibility toward organic matrix. Exemplary nonreactive surface modifiers include 2-[2-(2-methoxyethoxy)ethoxy] acetic acid (MEEAA) and 2-(2-methoxyethoxy)acetic acid (MEAA). Other exemplary nonreactive surface modifiers include the reaction product of an aliphatic or aromatic anhydride and a polyalkylene oxide mono-ether (e.g., succinic acid mono-[2-(2-methoxyethoxy)-ethyl] ester, maleic acid mono-[2-(2-methoxyethoxy)-ethyl] ester, and glutaric acid mono-[2-(2-methoxyethoxy)-ethyl] ester). In some embodiments, the surface modification agent is a carboxylic acid and/or anion thereof and the compatibility group imparts a non-polar character to the zirconia-containing nanoparticles. For example, the surface modification agent can be a carboxylic acid and/or anion thereof having a linear or branched aromatic group or aliphatic hydrocarbon group. Exemplary non-polar surface modifiers include octanoic acid, dodecanoic acid, stearic acid, oleic acid, and combinations thereof. Exemplary silane surface modifiers include such as N-(3-triethoxysilylpropyl) methoxyethoxyethoxyethyl carbamate, N-(3-triethoxysilylpropyl) methoxyethoxyethoxyethyl carbamate (available under the trade designation "SILQUEST A-1230" from Momentive Specialty Chemicals, Columbus, Ohio), n-octyltrimethoxysilane, n-octyltriethoxysilane, isooctyltrimethoxysilane, dodecyltrimethoxysilane, octadecyltrimethoxysilane, and propyltrimethoxysilane and combinations thereof.

Methods for adding a surface modification agent to the zirconia-containing nanoparticles are known in the art. The surface modification agent can be added, for example, before or after any removal of at least a portion of the carboxylic acids and/or anions thereof from the zirconia-containing sol. The surface modification agent can be added, for example, before or after removal of the water from the zirconia-containing sol. The organic matrix can be added, for example, after surface modification or simultaneously with surface modification.

Optionally, a radically reactive co-monomer can be incorporated into the sol to be copolymerized into the gel. The monomers can be mono-functional, difunctional or multifunctional. The monomers can have methacrylate, acrylate or styrenic functionality. The type of monomer used may depend on solvent system used. The monomers can be stiff or flexible. Exemplary monomers include hydroxyethyl methacrylate, acrylamide, 1-vinyl-2-pyrrolidione, hydroxyethyl acrylate, and butyl acrylate. Other exemplary monomers include di and multifunctional acrylates and methacrylates (e.g., pentaerythritol tetraacrylate and pentaerythritol triacrylate (available, for example, under the trade designations "SARTOMER SR444" and "SARTOMER SR295" from Sartomer Corporation), ethoxylated pentaerythritol tetraacrylate (available, for example, under the trade designation "SARTOMER SR494" from Sartomer Corporation), polyethylene glycol (400) dimethacrylate (available, for example, under the trade designation "SARTOMER SR603" from Sartomer Corporation), ethoxylated (3) trimethylolpropane triacrylate (available, for example, under the trade designation "SARTOMER SR454" from Sartomer Corporation), ethoxylated (9) trimethylolpropane triacrylate (available, for example, under the trade designation "SARTOMER 502" from Sartomer Corporation) ethoxylated (15) trimethylolpropane triacrylate (available, for example, under the trade designation "SARTOMER 9035" from Sartomer Corporation), and mixtures thereof.

In one exemplary embodiment, the gel is formed by radical polymerization of the surface modified particles and optional monomers. The polymerization can be initiated by any suitable means such as thermally or actinic radiation or UV initiators. Exemplary thermal initiators include (2,2'-azobis(2-methylbutyronitrile) (available, for example, under the trade designation "VAZO 67" from E. I. du Pont de Nemours and Company, Wilmington, Del.), azobisisobutyronitrile (available, for example, under the trade designation "VAZO 64" from E. I. du Pont de Nemours and Company), 2,2'-azodi-(2,4-Dimethylvaleronitrile (available, for example, under the trade designation "VAZO 52" from E. I. du Pont de Nemours and Company), and 1,1'-azobis (cyclohexanecabonitrile) (available, for example, under the trade designation "VAZO 88" from E. I. du Pont de Nemours and Company). Peroxides and hydroperoxides (e.g., benzoyl peroxide and lauryl peroxide) may also be useful. The initiator selection may be influenced, for example, by solvent choice, solubility and desired polymerization temperature. A preferred initiator is the 2,2'-azobis(2-methylbutyronitrile) available from E. I. du Pont de Nemours and Company under the trade designation "VAZO 67").

Exemplary UV initiators include 1-hydroxycyclohexyl benzophenone (available, for example, under the trade designation "IRGACURE 184" from Ciba Specialty Chemicals Corp., Tarrytown, N.Y.), 4-(2-hydroxyethoxy)phenyl-(2-hydroxy-2-propyl) ketone (available, for example, under the trade designation "IRGACURE 2529" from Ciba Specialty Chemicals Corp.), 2-hydroxy-2-methylpropiophenone (available, for example, under the trade designation "DAROCURE D111" from Ciba Specialty Chemicals Corp. and bis(2,4,6-trimethylbenzoyl)-phenylposphineoxide (available, for example, under the trade designation "IRGACURE 819" from Ciba Specialty Chemicals Corp.).

In some embodiments, dissolved oxygen is removed from the zirconia-based sols before forming the zirconia based gels. This can be accomplished, for example, by techniques known in the art, such as vacuum degassing or nitrogen gas purging. For example, the zirconia-based sol may be gelled by purging with nitrogen gas before heating. In some embodiments, the zirconia-based sol to be gelled can be placed in a mold and sealed from the atmosphere before further processing.

Liquid in the gel can be exchanged with a second liquid, for example, by soaking the gel in the second liquid for a time sufficient to allow an exchange to occur. For example, water present in a gel can be removed by soaking the gel in a dry solvent (e.g., 200 proof ethanol). In one embodiment, gels are soaked in ethanol in an amount 10 times that of the water present in the gel for 24 hours. The alcohol is then replaced with fresh dry solvent, and the process repeated four times. The times the gels are exposed to air should be minimized as ambient drying of the gels tends to cause cracking.

Typically the gels have x, y, z dimensions of at least 1 mm (in some embodiments, at least 3 mm, at least 5 mm, 10 mm, 15 mm, 20 mm, or even at least 25 mm), although the specific size may depend on the intended use of the resulting ceramic. For example, for some dental applications, the gels have x, y, z dimensions of greater than 1 mm, 5, mm, or even greater than 10 mm. The maximum size of the gels is limited by the practicality of subsequent processing steps such as organic burnout and extraction.

Aerogels

Aerogels described herein are formed by removing solvent from zirconia gels described herein without excessive shrinkage (e.g., not greater than 10%). Any suitable gel can be used. The gels described here a particularly well suited. The gel structure must be strong enough to withstand at least some shrinkage and cracking during the drying (solvent removal). The structure of the aerogel is essentially homogeneous.

The aerogels can be prepared by drying gels via super critical extraction. In some embodiments, the aerogels are prepared by drying gels under supercritical conditions of the solvent used in preparing the gel.

In some embodiments, of aerogels described herein, the crystalline metal oxide particles have an average primary particle size in a range from 2 nm to 50 nm (in some embodiments, 5 nm to 50 nm, 2 nm to 25 nm, 5 nm to 25 nm, 2 nm to 15 nm, or even 5 nm to 15 nm). Typically, the average primary particle size is measured by using the X-Ray Diffraction technique.

In some embodiments, aerogels described herein the crystalline metal oxide particles comprise a first plurality of particles, and a second, different plurality of particles (i.e., is distinguishable by average composition, phase(s), microstructure, and/or size).

Typically, aerogels described herein have an organic content that is at least 3 (in some embodiments, at least 4, 5, 10, 15, or even at least 20) percent by weight, based on the total weight of the aerogel. In some embodiments, aerogels described herein have an organic content in a range from 3 to 30, 10 to 30, or even 10 to 20 percent by weight, based on the total weight of the aerogel.

Exemplary organic materials for making aerogel described herein include acetic acid, acrylic acid, 2-hydroxyethyl methaacrylate, acrylamide 1-vinyl-2-pyrrolidione, trimethylolpropane triacrylate and ethoxylated. Other exemplary organics are ethoxylated pentaerythritol tetraacrylate (available, for example, under the trade designations "SR351," "SR350," and "SR454" from Sartomer Corporation), pentaerythritol triacrylate, teteraacrylate and ethoxylated versions such as those available under the trade designations "SR295," "SR444," "SR494" from Sartomer Corporation. Others (meth)acrylate monomers could also possibly be used in those formulations. Surface treatment agents include carboxlic acids, sulfonic acids, phosphonic acids, silanes. Changing to other solvent systems could expand the possible monomer choices even more. The aerogels could also possibly contain residual solvent(s) (e.g., water, ethanol, methanol methoxypropanol).

Optionally, aerogels described herein comprise at least one of $Y_2O_3$ (e.g., in a range from 1 to 15, 1 to 9, 1 to 5, 6 to 9, 3.5 to 4.5, or even 7 to 8) mole percent of the crystalline metal oxide is $Y_2O_3$), $La_2O_3$ (e.g., up to 5 mole percent $La_2O_3$), $Al_2O_3$ (e.g., up to 0.5 mole percent $Al_2O_3$). One exemplary aerogel comprises in a range from 1 to 5 mole percent of the crystalline metal oxide is $Y_2O_3$, and in a range from 0 to 2 mole percent of the crystalline metal oxide is $La_2O_3$, and in a range from 93 to 99 mole percent of the crystalline metal oxide is $ZrO_2$. Another exemplary aerogel comprises in a range from 6 to 9 mole percent of the crystalline metal oxide is $Y_2O_3$, and in a range from 0 to 2 mole percent of the crystalline metal oxide is $La_2O_3$, and in a range from 89 to 94 mole percent of the crystalline metal oxide is $ZrO_2$. In another exemplary aerogel the crystalline metal oxide comprises in a range from 3.5 to 4.5 mole percent $Y_2O_3$, and in a range from 0 to 2 mole percent of the crystalline metal oxide is $La_2O_3$, and in a range from 93.5 to 96.5 mole percent $ZrO_2$. In another exemplary aerogel the crystalline metal oxide comprises in a range from 7 to 8 mole percent $Y_2O_3$, and in a range from 0 to 2 mole percent of the crystalline metal oxide is $La_2O_3$, and in a range from 90 to 93 mole percent $ZrO_2$. Other optional oxides that may be present in aerogels described herein include at least one of $CeO_2$, $Pr_2O_3$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Tm_2O_3$, $Yb_2O_3$, $Fe_2O_3$, $MnO_2$, $Co_2O_3$, $Cr_2O_3$, NiO, CuO, $Bi_2O_3$, $Ga_2O_3$, or $Lu_2O_3$. Additives that may add desired coloring to the resulting crack free crystalline metal oxide articles include at least one of $Fe_2O_3$, $MnO_2$, $Co_2O_3$, $Cr_2O_3$, NiO, CuO, $Bi_2O_3$, $Ga_2O_3$, $Er_2O_3$, $Pr_2O_3$, $Eu_2O_3$, $Dy_2O_3$, $Sm_2O_3$, or $CeO_2$. In some embodiments, the amount of optional oxide(s) is in an amount in a range from about 10 ppm to 20,000 ppm. In some embodiments, it is desirable to have sufficient oxides present to so the crack free crystalline metal oxide articles has coloring of a tooth.

Aerogels described herein typically have a volume percent of oxide in a range of 3 to 20 (in some embodiments, 3 to 15, 3 to 14, or even 8 to 14) percent. Aerogels with lower volume percents of oxide tend to be very fragile and crack during supercritical drying or subsequent processing. Aerogels with higher oxide contents tend to crack during organic burnout because it is more difficult for volatile by-products to escape from the denser structure.

In some embodiments, aerogels described herein have a surface area (e.g. a BET surface area) in the range of 100 $m^2/g$ to 300 $m^2/g$ (in some embodiments, 150 $m^2/g$ to 250 $m^2/g$), and a continuous pore channel size (also referred to as "average connected pore size") in a range of 10 nm to 20 nm. In some embodiments, the structure of aerogels described herein is a composite of oxide particles, 3 nm to 10 nm (in some embodiments, 4 nm to 8 nm) in size and organics composed of acetate groups and polymerized monomers. The amount of organic is typically 10 to 20 weight percent of the aerogel.

Aerogels described herein can be made, for example, by providing a first zirconia sol comprising crystalline metal oxide particles having an average primary particle size of up to 50 nm (in some embodiments, 2 nm to 50 nm, 5 nm to 25 nm, 2 nm to 15 nm, or even 5 nm to 15 nm), wherein at least 70 (in some embodiments, at least 75, 80, 85, 90, 95, 96, 97, 98, or even at least 99; in a range from 70 to 99, 75 to 99, 80 to 99, or even 85 to 99) mole percent of the crystalline metal oxide is $ZrO_2$. The first zirconia sol is then optionally concentrated to provide a concentrated zirconia sol. A cosolvent, surface modifiers and optional monomers are added while stirring to obtain a well dispersed sol, wherein the cosolvent is optional). A radical initiator (e.g., ultraviolet (UV) or thermal initiator) is added to the radically polymerizable surface-modified zirconia sol. Optionally the resulting sol is purged with $N_2$ gas to remove oxygen. The resulting sol is then gelled by radiating with actinic or heating at at least one temperature for a time sufficient to polymerize the radically surface-modified zirconia sol comprising the radical initiator to form a gel. Typically the resulting gel is a strong, translucent gel. The water, if present, is then removed from the gel via alcohol exchange to provide an at least partially de-watered gel. The gel is then converted to an aerogel by removing the alcohol, if present, from the partially de-watered gel via super critical extraction to provide the aerogel.

The liquid solvent from the at least partially de-watered gel preferably removed in the absence of capillary forces in the gel structure to provide the monolithic aerogel, as even the presence of small capillary forces during the solvent removal can result in the collapse of the gel skeleton and crack the gel. In one exemplary embodiment removing the liquid solvent comprises placing the wet, at least partially de-watered gel in an autoclave, heating the autoclave above the critical temperature of the liquid solvent, pressurizing the autoclave above the critical pressure of the liquid solvent, then slowly removing the liquid solvent by releasing the pressure in the autoclave to about 1 bar at that temperature (i.e., the applicable critical temperature) to provide the monolithic aerogel.

In one exemplary embodiment, removing the first liquid solvent from the at least partially de-watered gel comprises replacing the first liquid solvent with a second liquid solvent, then slowly increasing the temperature and pressure of the at least partially de-watered gels until supercritical conditions for the second solvent are obtained, then slowly releasing the pressure to about 1 bar to provide the monolithic aerogel.

In some embodiments, the complete exchange of the first liquid solvent with the second solvent is carried out under supercritical conditions. In some embodiments, the first liquid solvent is miscible with the second solvent. This method comprises placing the at least partially de-watered gel into a pressure vessel with a sufficient volume of the first liquid solvent to completely immerse the gel, pumping the second solvent into the autoclave at a temperature above the critical temperature of the second solvent until a pressure greater than the critical pressure of the second solvent is reached, maintaining the supercritical pressure in the pressure vessel for a time sufficient to complete the solvent exchange by pumping an additional quantity of the second solvent into the pressure vessel while simultaneously venting the mixture of the first and second solvents to a separator vessel, then slowly releasing the pressure to 1 bar to provide the monolithic aerogel. Typically, the second solvent is carbon dioxide. Exemplary first liquid solvents include methanol, ethanol, isopropanol, β-methoxyethanol, β-ethoxyethanol, methoxypropanol, t-butyl alcohol, sec-butyl alcohol, t-amyl alcohol, hexanol, cyclohexanol, cyclohexane, heptane, dodecane, formic acid, acetic acid, hexanoic cid, isohexanoic acid, octanoic acid, acetal, acetaldehyde, acetic anhydride, acetone, acetonitrile, acetophenone, acetyl chloride, acrolein, acetonitrile, benzene, benzaldehyde, benzonitrile, benzoyl chloride, 2-butanone, n-butyl ether, camphor, carbon disulfide, carbon tetrachloride, chloroacetone, chlorobenzene, chloroform, cyclohexanone, 1-decene, p-dichlorobenzene, diethylene glycol monoethyl ether, N,N-diethylacetamide, N,N-dimethylacetamide, N,N-dimethylformamide, N,N-diethylformamide, 2,2-dimethylpentane, p-dioxane, ethyl acetate, ethyl acetoacetate, ethyl benzoate, ethyl carbonate, ethyl chloroacetate, ethyl chloroformate, ethylene bromide, ethylene diformate, ethylene glycol monobutyl ether, ethyl ether, ethyl formate, ethyl lactate, ethyl maleate, ethyl oxalate, ethyl phenylacetate, ethyl salicylate, ethyl succinate, ethyl sulfate, furfural, 1-heptaldehyde, 2,5-hexanedione, indene, isopropyl ether, limonene, methyl acetate, methylal, methyl benzoate, methylcyclohexane, methyl formate, methyl salicylate, methyl sulfate, nitrobenzene, nitroethane, nitromethane, o-nitrophenol, p-nitrotoluene, 1-nitropropane, 2-octanone, thioxane, paraldehyde, pentanaldehyde, 2-picoline, pinene, propionaldehyde, pyridine, salicylaldehyde, thiophene, toluene, triacetin, tri-sec-butylbenzene, and 2,2,3-trimethylbutane. Preferred first liquid solvents include methanol, ethanol, and methoxypropanol.

Further information on the principles and practice of super critical extraction can be found, for example, in van Bommel, M. J., and de Haan, A. B. *J. Materials Sci.* 29 (1994) 943-948, Francis, A. W. *J. Phys. Chem.* 58 (1954) 1099-1114 and McHugh, M. A., and Krukonis, V. J. *Supercritical Fluid Extraction: Principles and Practice.* Stoneham, Mass., Butterworth-Heinemann, 1986.

According to one embodiment the aerogel can be characterized by at least one of the following features: a) comprising crystalline zirconia particles having an average primary particle size in a range from 10 nm to 50 nm; b) content of crystalline zirconia particles: at least about 85 mol.-%; c) having a BET surface area in the range of 100 $m^2/g$ to 300 $m^2/g$; d) having an organic content of at least 3 wt.-%; e) x, y, z dimension: at least about 5 mm; f) showing a hysteresis loop (especially in a $p/p_0$ range of 0.70 to 0.95) when the $N_2$ adsorption/desorption behaviour is analysed; g) showing a type H1 hysteresis loop (according to IUPAC classification); h) showing a $N_2$ adsorption of isotherm type IV (according to IUPAC classification).

A combination of features (a) and (f) or (c) and (f) or (a), (c) and (h) is sometimes preferred.

Crack-Free, Calcined Metal Oxide Articles

Crack-free, calcined metal oxide articles can have x, y, and z dimensions of at least 3 mm (in some embodiments, at least 5 mm, 10 mm, 15 mm, 20 mm, or even at least 25 mm) and a density of at least 30 (in some embodiments, at least 35, 40, 50, 95; in a range from 30 to 95) percent of theoretical density, and an average connected pore size in a range from 10 nm to 100 nm (in some embodiments, from 10 nm to 60 nm, 10 nm to 50 nm, 10 nm to 40 nm, or even from 10 nm to 30 nm), wherein at least 70 (in some embodiments, at least 75, 80, 85, 90, 95, 96, 97, 98, or even at least 99; in a range from 70 to 99, 75 to 99, 80 to 99, or even 85 to 99) mole percent of the metal oxide is crystalline $ZrO_2$, and wherein the crystalline $ZrO_2$ has an average grain size less than 100 nm (in some embodiments, in a range from 20 nm to 100 nm, 30 nm to 100 nm, or even 30 nm to 70 nm).

Optionally, crack-free calcined metal oxide articles described herein comprise at least one of $Y_2O_3$ (e.g., in a range from 1 to 15, 1 to 5, 6 to 9, 3.5 to 4.5 or even 7 to 8) mole percent of the crystalline metal oxide is $Y_2O_3$), $La_2O_3$ (e.g., up to 5 mole percent $La_2O_3$), $Al_2O_3$ (e.g., up to 0.5 mole percent $Al_2O_3$). One exemplary crack-free calcined metal oxide article comprises in a range from 1 to 5 mole percent of the crystalline metal oxide is $Y_2O_3$, and in a range from 0 to 2 mole percent crystalline metal oxide is $La_2O_3$, and in a range from 93 to 99 mole percent of the crystalline metal oxide is $ZrO_2$. Another exemplary crack-free calcined metal oxide article comprises in a range from 6 to 9 mole percent of the crystalline metal oxide is $Y_2O_3$, and in a range from 0 to 2 mole percent crystalline metal oxide is $La_2O_3$, and in a range from 89 to 94 mole percent of the crystalline metal oxide is $ZrO_2$. Another exemplary crack-free calcined metal oxide article comprises in a range from 3.5 to 4.5 mole percent $Y_2O_3$, and in a range from 0 to 2 mole percent crystalline metal oxide is $La_2O_3$, and in a range from 93.3 to 96.5 mole percent $ZrO_2$. Another exemplary crack-free calcined metal oxide article comprises in a range from 7 to 8 mole percent $Y_2O_3$, and in a range from 0 to 2 mole percent crystalline metal oxide is $La_2O_3$, and in a range from 90 to 93 mole percent $ZrO_2$.

In some embodiments, the crack-free, calcined metal oxide article has a sulfate equivalent less than 5 ppm and/or a chloride equivalent less than 5 ppm. The raw material used to prepare the zirconia sol often contains chloride and sulfate impurities. Several thousand ppm by weight of these ions can be present in the calcined metal oxide article. If not removed these impurities can volatilize at the temperatures used for sintering and become entrapped in the sintered body as pores. The chloride and sulfate impurities can be removed prior to sintering, for example, by infiltrating the calcined body with a solution of ammonia in water, allowing it to sand overnight, then exchanging the ammonia solution with water several times. During this treatment ammonia reacts with the chloride and sulfate impurities to form soluble ammonia salts. These are removed by diffusion into the water. It is also possible to remove these impurities by adjusting the heating profile so that sufficient volatilization occurs in the thermal treatment used to form the calcined article.

Crack-free, calcined metal oxide articles described herein can be made by a method comprising heating an aerogel described herein for a time and at at least one temperature sufficient to provide the crack-free, calcined metal oxide article. Typically, the aerogel is slowly heated at rates in the range from 5° C./hr to 20° C./hr to 600° C. to remove organics. Slow heating below 600° C. is typically necessary to volatize the organics without cracking the body, for example, because of nonuniform shrinkage or internal pressure of the volatile products. Thermogravimetric analysis and dilatometry can be used to track the weight loss and shrinkage which occurs at different heating rates. The heating rates in different temperature ranges can then be adjusted to maintain a slow and near constant rate of weight loss and shrinkage until the organics are removed. Careful control of the organic removal is critical to obtain crack-free bodies. Once the organic is removed the temperature can be raised at a faster rate (e.g., 100° C./hr to 600° C./hr) to a temperature in the range from 800° C. to 1100° C. and held at that temperature up to 5 hours. At these temperatures the strength of the material increases by additional sintering, but an open pore structure is retained. When an ion-exchange treatment is used to remove chloride and sulfate impurities, the temperature and time used for heating the calcined body is such that it is strong enough to resist the capillary forces associated with infiltration of an ammonia solution. Typically this requires a relative density above 40% of theoretical (preferably above 45%). For articles that are to be milled, having the temperature too high and/or time too long can make milling difficult. In some cases it may be convenient to conduct the organic burnout separately; however, in that case care may be necessary to prevent absorption of moisture from the atmosphere prior to the higher temperature treatment. The aerogel can be quite fragile after heating to just 600° C., and nonuniform absorption of moisture can result in cracking.

Useful embodiments of crack-free, calcined metal oxide articles described herein include mill blocks, including dental mill blocks.

Crack-Free, Crystalline Metal Oxide Articles

Crack-free, crystalline metal oxide articles described herein have an x, y, and z dimensions of at least 3 mm (in some embodiments, at least 5 mm, 10 mm, 15 mm, 20 mm, or even 25 mm) and a density of at least 98.5 (in some embodiments, 99, 99.5, 99.9, or even at least 99.99) percent of theoretical density, wherein at least 70 mole percent of the crystalline metal oxide is $ZrO_2$, and wherein the $ZrO_2$ has an average grain size less than 400 nanometers (in some embodiments, less than 300 nanometers, 200 nanometers, 150 nanometers, 100 nanometers, or even less than 80 nanometers).

Optionally, crack-free, crystalline metal oxide articles described herein comprise at least one of $Y_2O_3$ (e.g., in a range from 1 to 15, 1 to 5, 6 to 9, 3.5 to 4.5 or even 7 to 8) mole percent of the crystalline metal oxide is $Y_2O_3$), $La_2O_3$ (e.g., up to 5 mole percent $La_2O_3$), $Al_2O_3$ (e.g., up to 0.5 mole percent $Al_2O_3$). One exemplary crack-free, crystalline metal oxide article comprises in a range from 1 to 5 mole percent of the crystalline metal oxide is $Y_2O_3$, 0 to 2 mole percent of the crystalline metal oxide is $La_2O_3$ and in a range from 93 to 97 mole percent of the crystalline metal oxide is $ZrO_2$. This general composition has been observed to yield a combination of high biaxial flexure strength and good optical transmittance. Another exemplary crack-free, crystalline metal oxide article comprises in a range from 6 to 9 mole percent of the crystalline metal oxide is $Y_2O_3$, 0 to 2 mole percent of the crystalline metal oxide is $La_2O_3$, and in a range from 89 to 94 mole percent of the crystalline metal oxide is $ZrO_2$. This general composition range has been observed to yield a combination of good biaxial flexure strength and high optical transmittance. Another exemplary crack-free, crystalline metal oxide article comprises in a range from 3.5 to 4.5 mole percent $Y_2O_3$, 0-2 mole percent of the crystalline metal oxide is $La_2O_3$, and in a range from 93.5 to 96.5 mole percent $ZrO_2$. This general composition has been observed to yield a combination of especially high biaxial flexure strength and good optical transmittance. Another exemplary crack-free, crystalline metal oxide article comprises in a range from 7 to 8 mole percent $Y_2O_3$, 0 to 2 mole percent of the crystalline metal oxide is $La_2O_3$, and in a range from 90 to 93 mole percent $ZrO_2$. This general composition range has been observed a combination of good biaxial flexure strength and especially high optical transmittance. The lower yttria compositions are therefore believed to be more desirable where high strength is required and moderate optical transmittance is sufficient. The higher yttria compositions are therefore believed to be more desirable where high optical transmittance is required and moderate strength is sufficient.

In another aspect, the present disclosure provides a method of making crack-free, crystalline metal oxide articles described herein, the method comprising heating a crack-free, calcined metal oxide article described herein for a time and at at least one temperature sufficient to provide the crack-free, crystalline metal oxide article. Typically, the heating is conducted at at least one temperature in a range from 1000° C. to 1400° C. (in some embodiments, from 1000° C. to 1400° C., 1000° C. to 1350° C., or even 1200° C. to 1300° C.). Typically, all the heating at or above 1000° C. is conducted in less than 24 hours; typically in a range from about 2 to about 24 hours. Typically, all the heating at or above 1000° C. is conducted at less than 1.25 atm. of pressure. Typically, the heating rate to temperature is in a range from 50° C./hr. to 600° C./hr. Heating can be conducted in conventional furnaces, preferably those with programmable heating capabilities. The material to be heated can be placed, for example, in an alumina crucible.

In some embodiments of the crack-free, crystalline metal oxide article, the $ZrO_2$ is all cubic $ZrO_2$. In some embodiments, the $ZrO_2$ is all tetragonal. In some embodiments, the zirconia is a mixture of tetragonal and cubic. Although not wanting to be bound by theory, based on the equilibrium phase diagram for $ZrO_2$ and $Y_2O_3$, mixtures of the cubic and tetragonal phases would be expected when the $Y_2O_3$ content is in the range from 2 to 8 mole percent and the material is sintered in the range from about 1200° C. to about 1250° C.

Embodiments with about 3.5 to 4.5 mole percent $Y_2O_3$ with a mixture of tetragonal and some cubic structure exhibit an exceptional combination of strength and optical transmittance. When sintered at 1250° C. for 2 hr the average grain size in one instance was 156 nm. Surprisingly only the tetragonal crystal structure was observed even though a mixture of tetragonal and cubic crystals would be expected in this composition range. When these materials were held at the sintering temperature for a prolonged time the grain size increased to 168 nm, a mixture of tetragonal and cubic crystalline phases was formed, and the good transmittance of the material was substantially reduced. In a similar manner, if the sintering temperature was raised to about 1500° C. and held for 2 hours, the grain size increased to 444 nm, additional cubic phase was formed, and the good optical transmittance was further degraded. It appears that maintaining the single phase tetragonal crystal structure and grain size of this composition below 175 nm is helpful for good optical transmission of this composition. A possible explanation for the nonequilibrium structures is that the chemical elements are very uniformly distributed in the nanoparticles making up the initial sol and aerogel. These are able to sinter to full density before the elements can segregate into equilibrium structures which would normally be present.

Embodiments containing about 7 to 8 mole percent $Y_2O_3$, with a mixture of cubic and some tetragonal structure, exhibit the best transmittance, and may be particularly useful in applications where lower strength can be tolerated. Although a mixture of tetragonal and cubic phases would be expected for this composition the material was entirely cubic. This is surprising as it would be expected that compositions composed entirely of the cubic phase would exhibit the best transmission as there would be no tetragonal phase to scatter light.

In some embodiments, the crack-free, crystalline metal oxide article has a total transmittance of at least 65% at a thickness of 1 mm as determined by the procedure under the heading "Total Transmittance, Diffuse Transmittance, Haze" in the Example section below.

In some embodiments, the crack-free, crystalline metal oxide article is colorless in visual appearance.

In some embodiments, the crack-free, crystalline metal oxide article is opalescent in visual appearance.

In some embodiments, the crack-free, crystalline metal oxide article has an average biaxial flexural strength of at least 300 MPa (in some embodiments, at least 500 MPa, 750 MPa, 1000 MPa, or even at least 1300 MPa).

Figure 4:
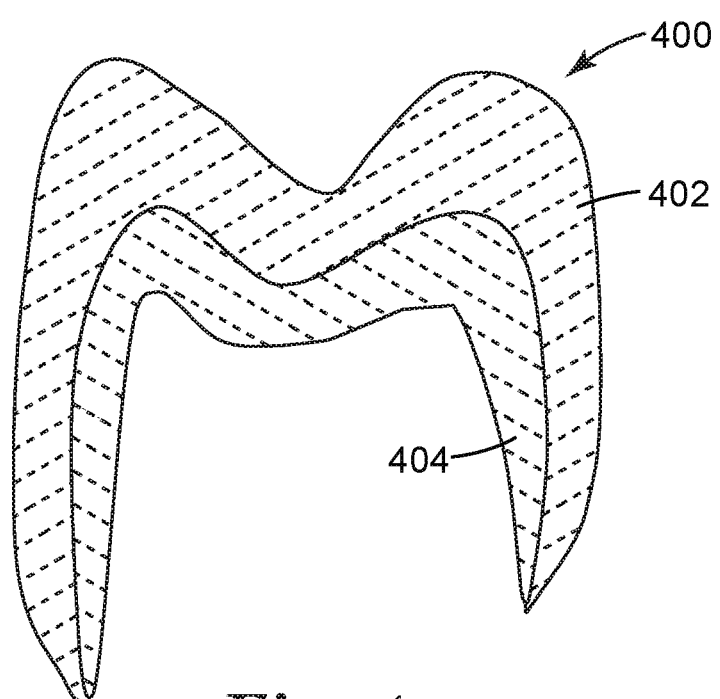
FIG. 4 is a cross-sectional view of an exemplary dental restoration.

Exemplary uses of crack-free, crystalline metal oxide articles described herein include optical windows, implants (e.g. tooth implants, artificial hip, and knee joints), and dental articles (e.g., restoratives (see, for example, FIG. 4 showing crown 400 with veneer 404 and coping 404, wither of which or both can comprising crack-free, crystalline metal oxide described herein), replacements, inlays, onlays, veneers, full and partial crowns, bridges, implants, implant abutments, copings, anterior fillings, posterior fillings, and cavity liner, and bridge frameworks) and orthodontic appliances (e.g., brackets, buccal tubes, cleats, and buttons). These articles could be milled, for example, from calcined oxide articles (mill-blocks) using computerized milling machines. Heating to temperatures near 1250° C. could complete sintering to full density.

According to one embodiment the crystalline metal oxide article can be characterized by the following features:
(a) showing a N2 adsorption of isotherm type IV according to IUPAC classification;
(b) showing a hysteresis loop when the N2 absorption/desorption behaviour is analysed;
(c) showing a N2 adsorption of isotherm type IV according to IUPAC classification and a hysteresis loop,
(d) showing a N2 adsorption of type IV with a hysteresis loop of type H1 according to IUPAC classification,
(e) showing a N2 adsorption of type IV with a hysterese loop of type H1 according to IUPAC classification in a p/p0 range of 0.70 to 0.95;
(f) average connected pore diameter: from about 10 to about 100 nm or from about 10 to about 70 nm or from about 10 to about or from about 10 to about 50 nm or from about 15 to about 40;
(g) average grain size: less than about 100 nm or less than about 80 nm or less than about 60 nm or from about 10 to about 100 or from about 15 to about 60 nm;
(h) BET surface: from about 10 to about 200 $m^2/g$ or from about 15 to about 100 $m^2/g$ or from about 16 to about 60 $m^2/g$;
(i) x, y, z dimension: at least about 5 mm or at least about 10 or at least about 20 mm.

A combination of the following features was found to be particularly beneficial: (a) and (h), or (a) and (b) and (h), or (c) and (g), or (c), (e), (g) and (h).

Surprisingly it was found that material showing a N2 adsorption of isotherm type IV (according to IUPAC classification) and/or a hysteresis loop (especially in a p/p0 range of 0.70 to 0.95) are particularly suitable.

According to one embodiment, the crystalline metal oxide article can be obtained by a process comprising the steps of
providing a zirconia sol comprising crystalline metal oxide particles and a solvent,
optionally concentrating the zirconia sol to provide a concentrated zirconia sol,
mixing the sol with a polymerizable organic matrix (e.g. adding a reactive surface modifier to the zirconia sol and optionally an initiator being able to polymerizable surface-modified particles of the zirconia sol);
optionally casting the zirconia sol into a mould to provide a casted zirconia sol,
curing the polymerizable organic matrix of the zirconia sol to form a gel (sometimes also referred to as gelation step),
removing the solvent from the gel (e.g. by first removing water, if present, from the gel via a solvent exchange process to provide an at least partially de-watered gel; followed by a further extraction step where the remaining solvent is extracted e.g. via super critical extraction) to provide the aerogel,
optionally cutting the aerogel into smaller pieces,
heat-treating the aerogel to obtain a machinable article.

According to a more specific embodiment, the crystalline metal oxide article can be obtained by a process comprising the steps of:
providing a zirconia sol comprising crystalline metal oxide particles,
optionally concentrating the zirconia sol to provide a concentrated zirconia sol,
adding a radically reactive surface modifier to the zirconia sol to provide surface-modified particles of the zirconia sol,
adding a radical initiator to the radically polymerizable surface-modified particles of the zirconia sol,
optionally casting the zirconia sol into a mould to provide a casted zirconia sol,
curing the radically polymerizable surface-modified particles of the zirconia sol to form a gel,
optionally removing water, if present, from the gel via a solvent exchange to provide an at least partially de-watered gel,
extracting solvent, if present, from the gel via super critical extraction to provide the aerogel,
optionally cutting the aerogel block into smaller pieces,
heat-treating the aerogel to obtain a machinable article.

Exemplary Embodiments

1A. An aerogel (in some embodiments, a monolithic aerogel (i.e., having x, y, and z dimensions of at least 1 mm (in some embodiments, at least 1.5 mm, 2 mm, 3 mm, 4 mm, 5 mm, 6 mm, 7 mm, 8 mm, 9 mm, or even at least 10 mm)) comprising organic material and crystalline metal oxide particles, wherein the crystalline metal oxide particles are in a range from 3 to 20 volume percent, based on the total volume of the aerogel, wherein at least 70 mole percent of the crystalline metal oxide is $ZrO_2$.

2A. The aerogel of Embodiment 1A, wherein the crystalline metal oxide particles have an average primary particle size in a range from 2 nanometers to 50 nanometers.

3A. The aerogel of any preceding Embodiment, wherein the crystalline metal oxide particles are in a range from 1 to 15 (in some embodiments, 1 to 9, 1 to 5, 6 to 9, 3.5 to 4.5 or even 7 to 8) mole percent of the crystalline metal oxide is $Y_2O_3$.

4A. The aerogel of any of Embodiments 1A to 3A, wherein the crystalline metal oxide particles further comprise at least one of $Y_2O_3$ or $La_2O_3$.

5A. The aerogel of any preceding Embodiment, wherein the crystalline metal oxide particles further comprise at least one of $CeO_2$, $Pr_2O_3$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Tm_2O_3$, $Yb_2O_3$, $Fe_2O_3$, $MnO_2$, $Co_2O_3$, $Cr_2O_3$, NiO, CuO, $Bi_2O_3$, $Ga_2O_3$, or $Lu_2O_3$.

6A. The aerogel of any of Embodiments 1A to 3A, wherein the crystalline metal oxide particles further comprise at least one of $Fe_2O_3$, $MnO_2$, $Co_2O_3$, $Cr_2O_3$, NiO, CuO, $Bi_2O_3$, $Ga_2O_3$, $Er_2O_3$, $Pr_2O_3$, $Eu_2O_3$, $Dy_2O_3$, $Sm_2O_3$, or $CeO_2$.

7A. The aerogel of any preceding Embodiment, wherein the crystalline metal oxide particles further comprise $Al_2O_3$.

8A. The aerogel of any preceding Embodiment, wherein the organic content is at least 3 percent by weight, based on the total weight of the aerogel.

9A. The aerogel of any preceding Embodiment having a surface area in a range from 100 $m^2/g$ to 300 $m^2/g$.

10A. The aerogel of any preceding Embodiment having an average connected pore size in a range from 10 nm to 20 nm.

11A. The aerogel of any preceding Embodiment, wherein the crystalline metal oxide particles comprise a first plurality of particles, and a second, different plurality of particles.

1B. A method of making the aerogel (in some embodiments, a monolithic aerogel (i.e., having x, y, and z dimensions of at least 1 mm (in some embodiments, at least 1.5 mm, 2 mm, 3 mm, 4 mm, 5 mm, or even at least 10 mm)) comprising organic material and crystalline metal oxide particles, wherein the crystalline metal oxide particles are in a range from 3 to 20 volume percent, based on the total volume of the aerogel, wherein at least 70 mole percent of the crystalline metal oxide is $ZrO_2$, the method comprising:
providing a first zirconia sol comprising crystalline metal oxide particles having an average primary particle size of not greater than 50 nanometers, wherein at least 70 mole percent of the crystalline metal oxide is $ZrO_2$;
optionally concentrating the first zirconia sol to provide a concentrated zirconia sol;
adding a radically reactive surface modifier to the zirconia sol to provide a radically polymerizable surface-modified zirconia sol;
adding a radical initiator to the radically polymerizable surface-modified zirconia sol;
heating at at least one temperature for a time sufficient to polymerize the radically surface-modified zirconia sol comprising the radical initiator to form a gel;
optionally removing water, if present, from the gel via alcohol exchange to provide an at least partially de-watered gel; and
extracting alcohol, if present, from the gel via super critical extraction to provide the aerogel.

2B. The method of Embodiment 1B further comprising adding a radically reactive co-monomer to the concentrated zirconia sol.

1C. A method of making a crack-free, calcined metal oxide article having x, y, and z dimensions of at least 5 mm, a density in as range from 30 to 95 percent of theoretical density, and an average connected pore size in a range from 10 nm to 100 nm, wherein at least 70 mole percent of the metal oxide is crystalline $ZrO_2$, and wherein the crystalline $ZrO_2$ has an average grain size less than 100 nm, the method comprising heating the monolithic aerogel of any of Embodiments 1A to 11A for a time and at at least one temperature sufficient to provide the crack-free, calcined metal oxide article.

2C. The method of Embodiment 1C further comprising chemically treating the calcined metal oxide article to remove volatile ions.

3C. The method of Embodiment 1C further comprising chemically treating the calcined metal oxide article to at least one remove Cl ions or $SO_4$ ions.

1D. A crack-free, calcined metal oxide article having x, y, and z dimensions of at least 5 mm, a density in a range from 30 to 95 percent of theoretical density, and an average connected pore size in a range from 10 nm to 100 nm, wherein at least 70 mole percent of the metal oxide is crystalline $ZrO_2$, and wherein the crystalline $ZrO_2$ has an average grain size less than 100 nm.

2D. The crack-free, calcined metal oxide of Embodiment 1D, wherein the crack-free, calcined metal oxide article has x, y, and z dimensions of at least 10 mm.

3D. The crack-free, calcined metal oxide of either Embodiment 1D or 2D, wherein at least 75 mole percent of the crystalline metal oxide present in the crack-free, calcined metal oxide article is crystalline $ZrO_2$.

4D. The crack-free, calcined metal oxide of any of Embodiments 1D to 3D, wherein the crystalline metal oxide comprises in a range from 1 to 15 (in some embodiments, 1 to 9, 1 to 5, 6 to 9 3.5 to 4.5, or even 7 to 8) mole percent of the crystalline metal oxide is $Y_2O_3$.

5D. The crack-free, calcined metal oxide of any of Embodiments 1D to 4D, wherein the crystalline metal oxide further comprises at least one of $Y_2O_3$ or $La_2O_3$.

6D. The crack-free, calcined metal oxide of any of Embodiments 1D to 5D, wherein the crystalline metal oxide further comprises at least one of $CeO_2$, $Pr_2O_3$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Tm_2O_3$, $Yb_2O_3$, $Fe_2O_3$, $MnO_2$, $Co_2O_3$, $Cr_2O_3$, NiO, CuO, $Bi_2O_3$, $Ga_2O_3$, or $Lu_2O_3$.

7D. The crack-free, calcined metal oxide of any of Embodiments 1D to 5D, wherein the crystalline metal oxide further comprises at least one of $Fe_2O_3$, $MnO_2$, $Co_2O_3$, $Cr_2O_3$, NiO, CuO, $Bi_2O_3$, $Ga_2O_3$, $Er_2O_3$, $Pr_2O_3$, $Eu_2O_3$, $Dy_2O_3$, $Sm_2O_3$, or $CeO_2$.

8D. The crack-free, calcined metal oxide of Embodiments 1D to 7D, wherein the crystalline metal oxide further comprises $Al_2O_3$.

9D. The crack-free, calcined metal oxide of any of Embodiments 1D to 8D having a sulfate equivalent less than 5 ppm and a chloride equivalent less than 5 ppm.

10D. The crack-free, calcined metal oxide of any of Embodiments 1D to 9D which is a mill block.

1E. A method of making a crack-free, crystalline metal oxide article having an x, y, and z dimensions of at least 3 mm and a density of at least 98.5 (in some embodiments, at least 99, 99.5, 99.9, or even at least 99.99) percent of theoretical density, wherein at least 70 mole percent of the crystalline metal oxide is $ZrO_2$, and wherein the $ZrO_2$ has an average grain size less than 400 nanometers (in some embodiments, less than 300 nanometers, 200 nanometers, 150 nanometers, 100 nanometers, or even less than 80 nanometers), the method comprising heating a crack-free, calcined metal oxide article of any of Embodiments 1D to 10D for a time and at at least one temperature sufficient to provide the crack-free, crystalline metal oxide article.

2E. The method of Embodiment 1E, wherein the heating is conducted at at least one temperature in a range from 1150° C. to 1300° C.

3E. The method of either Embodiment 1E or 2E, wherein all the heating is conducted in less than 24 hours.

4E. The method of any of Embodiments 1E to 3E, wherein all the heating is conducted at less than 1.25 atm. of pressure.

5E. The method of any of Embodiments 1E to 4E, wherein the $ZrO_2$ present in the crack-free, crystalline metal oxide article is all cubic $ZrO_2$.

6E. The method of any of Embodiments 1E to 4E, wherein the $ZrO_2$ present in the crack-free, crystalline metal oxide article comprises all tetragonal $ZrO_2$.

7E. The method of any of Embodiments 1E to 4E, wherein the $ZrO_2$ present in the crack-free, crystalline metal oxide article comprises cubic and tetragonal $ZrO_2$.

8E. The method of any of Embodiments 1E to 7E, wherein the crack-free, crystalline metal oxide article has a total transmittance of at least 65% at a thickness of 1 mm.

9E. The method of any of Embodiments 1E to 8E, wherein the crack-free, crystalline metal oxide article is colorless.

10E. The method of any of Embodiments 1E to 8E, wherein the crack-free, crystalline metal oxide article is opalescent.

11E. The method of any of Embodiments 1E to 10E, wherein the crack-free, crystalline metal oxide article has a biaxial flexural strength of at least 300 MPa (in some embodiments, in a range from 300 MPa to 1300 MPa).

12E. The method of any of Embodiments 1E to 11E, wherein the crack-free, crystalline metal oxide article is a dental article.

13E. The method of Embodiment 12E, wherein the dental article is selected from the group consisting of restoratives, replacements, inlays, onlays, veneers, full and partial crowns, bridges, implants, implant abutments, copings, anterior fillings, posterior fillings, and cavity liner, and bridge frameworks.

14E. The method of any of Embodiments 1E to 13E, wherein the crack-free, crystalline metal oxide article is an orthodontic appliance.

15E. The method of Embodiment 14E, wherein the orthodontic appliance is selected from the group consisting of brackets, buccal tubes, cleats, and buttons.

1F. A crack-free, crystalline metal oxide article having an x, y, and z dimensions of at least 3 mm and a density of at least 98.5 (in some embodiments, at least 99, 99.5, 99.9, or even at least 99.99) percent of theoretical density, wherein at least 70 mole percent of the crystalline metal oxide is $ZrO_2$, and wherein the $ZrO_2$ has an average grain size in a range from 75 nanometers to 400 nanometers.

2F. The crack-free, crystalline metal oxide article of Embodiment 1F, wherein the crystalline metal oxide comprises in a range from 1 to 15 mole percent (in some embodiments 1 to 9 mole percent) $Y_2O_3$.

3F. The crack-free, crystalline metal oxide article of either Embodiment 1F or 2F, wherein the crystalline metal oxide further comprises $La_2O_3$.

4F. The crack-free, crystalline metal oxide article of any of Embodiments 1F to 3F, wherein the crystalline metal oxide further comprises at least one of $CeO_2$, $Pr_2O_3$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Tm_2O_3$, $Yb_2O_3$, $Fe_2O_3$, $MnO_2$, $Co_2O_3$, $Cr_2O_3$, NiO, CuO, $Bi_2O_3$, $Ga_2O_3$, or $Lu_2O_3$.

5F. The crack-free, crystalline metal oxide article of any of Embodiments 1F to 3F, wherein the crystalline metal oxide further comprises at least one of $Fe_2O_3$, $MnO_2$, $Co_2O_3$, $Cr_2O_3$, NiO, CuO, $Bi_2O_3$, $Ga_2O_3$, $Er_2O_3$, $Pr_2O_3$, $Eu_2O_3$, $Dy_2O_3$, $Sm_2O_3$, or $CeO_2$.

6F. The crack-free, crystalline metal oxide article of any of Embodiments 1F to 5F, wherein the crystalline metal oxide further comprises $Al_2O_3$.

7F. The crack-free, crystalline metal oxide article of any of Embodiments 1F to 6F, wherein the $ZrO_2$ is all cubic $ZrO_2$.

8F. The crack-free, crystalline metal oxide article of any of Embodiments 1F to 7F, wherein the $ZrO_2$ is all tetragonal $ZrO_2$.

9F. The crack-free, crystalline metal oxide article of any of Embodiments 1F to 7F, wherein the $ZrO_2$ comprises cubic and tetragonal $ZrO_2$.

10F. The crack-free, crystalline metal oxide article of any of Embodiments 1F to 9F having a total transmittance of at least 65% at a thickness of 1 mm.

11F. The crack-free, crystalline metal oxide article of any of Embodiments 1F to 1° F. that is colorless.

12F. The crack-free, crystalline metal oxide article of any of Embodiments 1F to 10F that is opalescent.

13F. The crack-free, crystalline metal oxide article of any of Embodiments 1F to 12F that passes the Hydrolytic Stability Test.

14F. The crack-free, crystalline metal oxide article of any of Embodiments 1F to 13F that is a dental article.

15F. The crack-free, crystalline metal oxide article of Embodiment 14F, wherein the dental article is selected from the group consisting of restoratives, replacements, inlays, onlays, veneers, full and partial crowns, bridges, implants, implant abutments, copings, anterior fillings, posterior fillings, and cavity liner, and bridge frameworks.

16F. The crack-free, crystalline metal oxide article of any of Embodiments 1F to 13F that is an orthodontic appliance.

17F. The crack-free, crystalline metal oxide article of Embodiment 16F, wherein the orthodontic appliance is selected from the group consisting of brackets, buccal tubes, cleats, and buttons.

1G. A crack-free, crystalline metal oxide article having an x, y, and z dimensions of at least 3 mm and a density of at least 99.5 (in some embodiments, at least 99, 99.5, 99.9, or even at least 99.99) percent of theoretical density, wherein at least 70 mole percent of the crystalline metal oxide is $ZrO_2$, wherein in range from 1 to 5 mole percent (in some embodiments 3.5 to 4.5 mole percent) of the crystalline metal oxide is $Y_2O_3$, and wherein the $ZrO_2$ has an average grain size 75 nanometers to 175 nanometers (in some embodiments, in a range from 100 nanometers to 165 nanometers).

2G. The crack-free, crystalline metal oxide article of Embodiment 1G, wherein the crystalline metal oxide further comprises $La_2O_3$.

3G. The crack-free, crystalline metal oxide article of either Embodiment 1G or 2G, wherein the crystalline metal oxide further comprises at least one of $CeO_2$, $Pr_2O_3$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Tm_2O_3$, $Yb_2O_3$, $Fe_2O_3$, $MnO_2$, $Co_2O_3$, $Cr_2O_3$, NiO, CuO, $Bi_2O_3$, $Ga_2O_3$, or $Lu_2O_3$.

4G. The crack-free, crystalline metal oxide article of either Embodiment 1G or 2G, wherein the crystalline metal oxide further comprises at least one of $Fe_2O_3$, $MnO_2$, $Co_2O_3$, $Cr_2O_3$, NiO, CuO, $Bi_2O_3$, $Ga_2O_3$, $Er_2O_3$, $Pr_2O_3$, $Eu_2O_3$, $Dy_2O_3$, $Sm_2O_3$, or $CeO_2$.

5G. The crack-free, crystalline metal oxide article of any of Embodiments 1G to 4G, wherein the crystalline metal oxide further comprises $Al_2O_3$.

6G. The crack-free, crystalline metal oxide article of any of Embodiments 1G to 5G, wherein the $ZrO_2$ is all tetragonal $ZrO_2$.

7G. The crack-free, crystalline metal oxide article of any of Embodiments 1G to 5G, wherein the $ZrO_2$ comprises cubic and tetragonal $ZrO_2$.

8G. The crack-free, crystalline metal oxide article of any of Embodiments 1G to 7G having a total transmittance of at least 65% at a thickness of 1 mm.

9G. The crack-free, crystalline metal oxide article of any of Embodiments 1G to 7G that is colorless.

10G. The crack-free, crystalline metal oxide article of any of Embodiments 1G to 9G that is opalescent.

11G. The crack-free, crystalline metal oxide article of any of Embodiments 1G to 10G that passes the Hydrolytic Stability Test.

12G. The crack-free, crystalline metal oxide article of any of Embodiments 1G to 11G that is a dental article.

13G. The crack-free, crystalline metal oxide article of Embodiment 12G, wherein the dental article is selected from the group consisting of restoratives, replacements, inlays, onlays, veneers, full and partial crowns, bridges, implants, implant abutments, copings, anterior fillings, posterior fillings, and cavity liner, and bridge frameworks.

14G. The crack-free, crystalline metal oxide article of any of Embodiments 1G to 11G that is an orthodontic appliance.

15G. The crack-free, crystalline metal oxide article of Embodiment 14G, wherein the orthodontic appliance is selected from the group consisting of brackets, buccal tubes, cleats, and buttons.

16G. The crack-free, crystalline metal oxide article of any of Embodiments 1G to 15G, wherein the crack-free, crystalline metal oxide article is composed entirely of the tetragonal crystal structure.

1H. A method of making a crack-free, crystalline metal oxide article of any of Embodiments 1G to 12G the method comprising heating a crack-free, calcined metal oxide article for a time and at at least one temperature sufficient to provide the crack-free, crystalline metal oxide article, the crack-free, calcined metal oxide article having an x, y, and z dimensions of at least 3 mm, a density in a range from 30 to 95 percent of theoretical density, and an average connected pore size in a range from 10 nm to 100 nm, wherein at least 70 mole percent of the metal oxide is crystalline $ZrO_2$, wherein at least 70 mole percent of the crystalline metal oxide is $ZrO_2$, wherein in range from 1 to 5 mole percent (in some embodiments 3.5 to 4.5 mole percent) of the crystalline metal oxide is $Y_2O_3$, and wherein the crystalline $ZrO_2$ has an average grain size less than 100 nm.

2H. The method of Embodiment 1H, wherein the heating is conducted at at least one temperature in a range from 1150° C. to 1300° C.

3H. The method of either Embodiment 1H or 2H, wherein all the heating is conducted in less than 24 hours.

4H. The method of any of Embodiments 1H to 3H, wherein all the heating is conducted at less than 1.25 atm. of pressure.

5H. The method of any of Embodiments 1H to 4H, wherein the crack-free, calcined metal oxide article has x, y, and z dimensions of at least 10 mm.

6H. The method of any of Embodiments 1H to 5H, wherein at least 75 mole percent of the crystalline metal oxide present in the crack-free, calcined metal oxide article is crystalline $ZrO_2$.

7H. The method of any of Embodiments 1H to 6H, wherein the crack-free, calcined metal oxide article crystalline metal oxide further comprises $La_2O_3$.

8H. The method of any of Embodiments 1H to 7H, wherein the crack-free, calcined metal oxide article crystalline metal oxide further comprises at least one of $CeO_2$, $Pr_2O_3$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Tm_2O_3$, $Yb_2O_3$, $Fe_2O_3$, $MnO_2$, $Co_2O_3$, $Cr_2O_3$, NiO, CuO, $Bi_2O_3$, $Ga_2O_3$, or $Lu_2O_3$.

9H. The method of any of Embodiments 1H to 7H, wherein the crack-free, calcined metal oxide article crystalline metal oxide further comprises at least one of $Fe_2O_3$, $MnO_2$, $Co_2O_3$, $Cr_2O_3$, NiO, CuO, $Bi_2O_3$, $Ga_2O_3$, $Er_2O_3$, $Pr_2O_3$, $Eu_2O_3$, $Dy_2O_3$, $Sm_2O_3$, or $CeO_2$.

10H. The method of Embodiments 1H to 9H, wherein the crystalline metal oxide further comprises $Al_2O_3$.

11H. The method of any of Embodiments 1H to 10H, wherein the crack-free, calcined metal oxide has a sulfate equivalent less than 5 ppm and a chloride equivalent less than 5 ppm.

12H. The method of any of Embodiments 1H to 11H, wherein the crack-free calcined metal oxide article is a mill block.

1I. A crack-free, crystalline metal oxide article having an x, y, and z dimensions of at least 3 mm and a density of at least 98.5 (in some embodiments, 99, 99.5, 99.9, or at least at least 99.99) percent of theoretical density, wherein at least 70 mole percent of the crystalline metal oxide is $ZrO_2$, wherein in range from 6 to 9 mole percent (in some embodiments 7 to 8 mole percent) of the crystalline metal oxide is $Y_2O_3$, and wherein the $ZrO_2$ has an average grain size in a range from 100 nanometers to 400 nanometers (in some embodiments, in a range from 200 nanometers to 300 nanometers).

2I. The crack-free, crystalline metal oxide article of Embodiment 1I, wherein the crystalline metal oxide further comprises $La_2O_3$.

3I. The crack-free, crystalline metal oxide article of either Embodiment 1I or 2I, wherein the crystalline metal oxide further comprises at least one of $CeO_2$, $Pr_2O_3$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Tm_2O_3$, $Yb_2O_3$, $Fe_2O_3$, $MnO_2$, $Co_2O_3$, $Cr_2O_3$, NiO, CuO, $Bi_2O_3$, $Ga_2O_3$, or $Lu_2O_3$.

4I. The crack-free, crystalline metal oxide article of either Embodiment 1I or 2I, wherein the crystalline metal oxide further comprises at least one of $Fe_2O_3$, $MnO_2$, $Co_2O_3$, $Cr_2O_3$, NiO, CuO, $Bi_2O_3$, $Ga_2O_3$, $Er_2O_3$, $Pr_2O_3$, $Eu_2O_3$, $Dy_2O_3$, $Sm_2O_3$, or $CeO_2$.

5I. The crack-free, crystalline metal oxide article of any of Embodiments 1I to 4I, wherein the crystalline metal oxide further comprises $Al_2O_3$.

6I. The crack-free, crystalline metal oxide article of any of Embodiments 1I to 5I, wherein the $ZrO_2$ is all cubic $ZrO_2$.

7I. The crack-free, crystalline metal oxide article of any of Embodiments 1I to 5I, wherein the $ZrO_2$ comprises cubic and tetragonal $ZrO_2$.

8I. The crack-free, crystalline metal oxide article of any of Embodiments 1I to 7I having a total transmittance of at least 65% at a thickness of 1 mm.

9I. The crack-free, crystalline metal oxide article of any of Embodiments 1I to 8I that is colorless.

10I. The crack-free, crystalline metal oxide article of any of Embodiments 1I to 8I that is opalescent.

11I. The crack-free, crystalline metal oxide article of any of Embodiments 1I to 10I that passes the Hydrolytic Stability Test.

12I. The crack-free, crystalline metal oxide article of any of Embodiments 1I to 11I that is a dental article.

13I. The crack-free, crystalline metal oxide article of Embodiment 12I, wherein the dental article is selected from the group consisting of restoratives, replacements, inlays, onlays, veneers, full and partial crowns, bridges, implants, implant abutments, copings, anterior fillings, posterior fillings, and cavity liner, and bridge frameworks.

14I. The crack-free, crystalline metal oxide article of any of Embodiments 1I to 11I that is an orthodontic appliance.

15I. The crack-free, crystalline metal oxide article of Embodiment 14I, wherein the orthodontic appliance is selected from the group consisting of brackets, buccal tubes, cleats, and buttons.

16I. The crack-free, crystalline metal oxide article of any of Embodiments 1I to 15I, wherein the crack-free, crystalline metal oxide article contains less than 8 mole percent of $Y_2O_3$ and is composed entirely of the cubic crystal structure.

1J. A method of making a crack-free, crystalline metal oxide article of any of Embodiments 1I to 15I, the method comprising heating a crack-free, calcined metal oxide article for a time and at at least one temperature sufficient to provide the crack-free, crystalline metal oxide article, the crack-free, calcined metal oxide article having x, y, and z dimensions of at least 3 mm, a density in a range from 30 to 95 percent of theoretical density, and an average connected pore size in a range from 10 nm to 100 nm, wherein at least 70 mole percent of the metal oxide is crystalline $ZrO_2$, wherein at least 70 mole percent of the crystalline metal oxide is $ZrO_2$, wherein in range from 6 to 9 mole percent (in some embodiments, 7 to 8 mole percent) of the crystalline metal oxide is $Y_2O_3$, and wherein the crystalline $ZrO_2$ has an average grain size less than 100 nm.

2J. The method of Embodiment 1J, wherein the heating is conducted at at least one temperature in a range from 1150° C. to 1300° C.

3J. The method of either Embodiment 1J or 2J, wherein all the heating is conducted in less than 24 hours.

4J. The method of any of Embodiments 1J to 3J, wherein all the heating is conducted at less than 1.25 atm. of pressure.

5J. The method of any of Embodiments 1J to 4J, wherein the crack-free, calcined metal oxide article has x, y, and z dimensions of at least 10 mm.

6J. The method of any of Embodiments 1J to 5J, wherein at least 75 mole percent of the crystalline metal oxide present in the crack-free, calcined metal oxide article is crystalline $ZrO_2$.

7J. The method of any of Embodiments 1J to 6J, wherein the crack-free, calcined metal oxide article further comprises $La_2O_3$.

8J. The method of any of Embodiments 1J to 7J, wherein the crack-free, calcined metal oxide article further comprises at least one of $CeO_2$, $Pr_2O_3$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Tm_2O_3$, $Yb_2O_3$, $Fe_2O_3$, $MnO_2$, $Co_2O_3$, $Cr_2O_3$, NiO, CuO, $Bi_2O_3$, $Ga_2O_3$, or $Lu_2O_3$.

9J. The method of any of Embodiments 1J to 8J, wherein the crack-free, calcined metal oxide article further comprises at least one of $Fe_2O_3$, $MnO_2$, $Co_2O_3$, $Cr_2O_3$, NiO, CuO, $Bi_2O_3$, $Ga_2O_3$, $Er_2O_3$, $Pr_2O_3$, $Eu_2O_3$, $Dy_2O_3$, $Sm_2O_3$, or $CeO_2$.

10J. The method of Embodiments 1J to 9J, wherein the wherein the crack-free, calcined metal oxide article further comprises further comprises $Al_2O_3$.

11J. The method of any of Embodiments 1J to 10J, wherein the crack-free, calcined metal oxide article further comprises has a sulfate equivalent less than 5 ppm and a chloride equivalent less than 5 ppm.

12J. The method of any of Embodiments 1J to 11J, wherein the crack-free, calcined metal oxide article is a mill block.

1K. A method of making a crack-free, crystalline metal oxide article having an x, y, and z dimensions of at least 3 mm and a density of at least 98.5 (in some embodiments, at least 99, 99.5, 99.9, or even at least 99.99) percent of theoretical density, wherein at least 70 mole percent of the crystalline metal oxide is $ZrO_2$, and wherein the $ZrO_2$ has an average grain size less than 300 nanometers, the method comprising pressureless heating in air a crack-free, calcined metal oxide article having x, y, and z dimensions of at least 5 mm, a density of at least 30 percent of theoretical density, wherein at least 70 mole percent of the metal oxide is crystalline $ZrO_2$, and wherein the crystalline $ZrO_2$ has an average grain size less than 100 nm for a time and at at least one temperature sufficient to provide the crack-free, crystalline metal oxide article, wherein the method is conducted at no greater than 1400° C.

2K. The method of Embodiment 1K, wherein the heating is conducted at at least one temperature in a range from 1000° C. to 1400° C. (in some embodiments, 1000° C. to 1350° C., or even 1200° C. to 1300° C.).

3K. The method of either Embodiment 1K or 2K, wherein all the heating is conducted in less than 24 hours.

4K. The method of any of Embodiments 1K to 3K, wherein the $ZrO_2$ present in the crack-free, crystalline metal oxide article is all cubic $ZrO_2$.

5K. The method of any of Embodiments 1K to 3K, wherein the $ZrO_2$ present in the crack-free, crystalline metal oxide article comprises all tetragonal $ZrO_2$.

6K. The method of any of Embodiments 1K to 3K, wherein the $ZrO_2$ present in the crack-free, crystalline metal oxide article comprises cubic and tetragonal $ZrO_2$.

7K. The method of any of Embodiments 1K to 6K, wherein the crack-free, calcined metal oxide article further comprises $La_2O_3$.

8K. The method of any of Embodiments 1K to 7K, wherein the crack-free, calcined metal oxide article comprises at least one of $CeO_2$, $Pr_2O_3$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Tm_2O_3$, $Yb_2O_3$, $Fe_2O_3$, $MnO_2$, $Co_2O_3$, $Cr_2O_3$, NiO, CuO, $Bi_2O_3$, $Ga_2O_3$, or $Lu_2O_3$.

9K. The method of any of Embodiments 1K to 7K, wherein the crack-free, calcined metal oxide article comprises at least one of $Fe_2O_3$, $MnO_2$, $Co_2O_3$, $Cr_2O_3$, NiO, CuO, $Bi_2O_3$, $Ga_2O_3$, $Er_2O_3$ $Pr_2O_3$, $Eu_2O_3$, $Dy_2O_3$, $Sm_2O_3$, or $CeO_2$.

10K. The method of Embodiments 1K to 9K, wherein the crack-free, calcined metal oxide article further comprises $Al_2O_3$.

11K. The method of any of Embodiments 1K to 10K, wherein the crack-free, crystalline metal oxide article has a total transmittance of at least 65% at a thickness of 1 mm.

12K. The method of any of Embodiments 1K to 11K, wherein the crack-free, crystalline metal oxide article is colorless.

13K. The method of any of Embodiments 1K to 11K, wherein the crack-free, crystalline metal oxide article is opalescent.

14K. The method of any of Embodiments 1K to 13K, wherein the crack-free, crystalline metal oxide article has a biaxial flexural strength of at least 300 MPa (in some embodiments, in a range from 300 MPa to 1300 MPa).

15K. The method of any of Embodiments 1K to 14K, wherein the crack-free, crystalline metal oxide article is a dental article.

16K. The method of Embodiment 15K, wherein the dental article is selected from the group consisting of restoratives, replacements, inlays, onlays, veneers, full and partial crowns, bridges, implants, implant abutments, copings, anterior fillings, posterior fillings, and cavity liner, and bridge frameworks.

17K. The method of any of Embodiments 1K to 16K, wherein the crack-free, crystalline metal oxide article is an orthodontic appliance.

18K. The method of Embodiment 17K, wherein the orthodontic appliance is selected from the group consisting of brackets, buccal tubes, cleats, and buttons.

Advantages and embodiments of this invention are further illustrated by the following examples, but the particular materials and amounts thereof recited in these examples, as well as other conditions and details, should not be construed to unduly limit this invention. All parts and percentages are by weight unless otherwise indicated. In the following examples, "mol %" means mole percent.

Test Methods

X-ray Diffraction Analysis (XRD)

Samples of sintered bodies were examined without any further changes. Reflection geometry data were collected in the form of a survey scan by use of a diffractometer (obtained under the trade designation "BRUKER D8 ADVANCE DIFFRACTOMETER" from Bruker Corporation, Madison, Wis.) with copper $K_\alpha$ radiation, and detector registry of the scattered radiation. The diffractometer was fitted with variable incident beam slits and fixed diffracted beam slits. The survey scan was conducted in the coupled continuous mode from 10 to 80 degrees (2θ) using a 0.015 degree step size and 2 second dwell time. The x-ray generator settings of 40 kilovolts and 40 milliamps were employed.

The observed diffraction peaks were identified by comparison to the reference diffraction patterns contained within the International Center for Diffraction Data (ICDD) powder diffraction database (sets 1-47, ICDD, Newton Square, Pa.) and attributed to cubic (C), tetragonal (T), or monoclinic (M) phases of zirconia. The (111) peak was used for the cubic phase, the (101) peak was used for the tetragonal phase, and the (−111) and (111) peaks were used for the monoclinic phase. Because of the small crystalline size of the particles as prepared in the sol, the (111) peak for the cubic phase and the (101) peak for the tetragonal phase could not be separated. The phases are reported together as the C (111)/T (101) peak. The amounts of each zirconia phase were evaluated on a relative basis and the form of zirconia having the most intense diffraction peak was assigned the relative intensity value of 100. The strongest line of the remaining crystalline zirconia phase was scaled relative to the most intense line and given a value between 1 and 100.

Peak widths for the observed diffraction maxima due to corundum were measured by profile fitting. The relationship between mean corundum peak widths and corundum peak position (2θ) was determined by fitting a polynomial to these data to produce a continuous function used to evaluate the instrumental breadth at any peak position within the corundum testing range. Peak widths for the observed diffraction maxima due to zirconia were measured by profile fitting the observed diffraction peaks.

A Pearson VII peak shape model with $K_{\alpha 1}$ and $K_{\alpha 2}$ wavelength components accounted for, and linear background model were employed in all cases. Widths were found as the peak full width at half maximum (FWHM) having units of degrees. The profile fitting was accomplished by use of the capabilities of the JADE diffraction software suite.

Sample peaks were corrected for instrumental broadening by interpolation of instrumental breadth values from corundum instrument calibration and corrected peak widths converted to units of radians. The Scherrer equation was used to calculate the primary crystal size.

Crystallite Size $(D) = K\lambda/\beta(\cos \theta)$

In the Scherrer equation, K is the form factor (here 0.9), $\lambda$ is the wavelength (1.540598 Å), $\beta$ is the calculated peak width after correction for instrumental broadening (in radians), and $\theta$ equals half the peak position (scattering angle). $\beta$ is equal to [calculated peak FWHM—instrumental breadth] (converted to radians) where FWHM is full width at half maximum.

The weighted average of the cubic/tetragonal (C/T) and monoclinic phases (M) were calculated using the following equation.

Weighted average=[(% $C/T$)($C/T$ size)+(% $M$)($M$ size)]/100

In this equation, % C/T equals the percent crystallinity contributed by the cubic and tetragonal crystallite content of the $ZrO_2$ particles; C/T size equals the size of the cubic and tetragonal crystallites; % M equals the percent crystallinity contributed by the monoclinic crystallite content of the $ZrO_2$ particles; and M size equals the size of the monoclinic crystallites.

Inductively Coupled Plasma Atomic Emission Spectroscopy (ICP)

Inductively Coupled Plasma Atomic Emission Spectroscopy was used to analyze the zirconia-based sol samples for the lanthanide and yttrium element concentration. Liquid samples were aspirated into a high temperature argon plasma where desolvation, dissociation, atomization, and excitation occur. Each element has a well established and characteristic wavelengths associated with emission from an excited state. The intensity of the emission is typically proportional to the concentration of the element. The concentration of the element can be calculated by comparing the intensity of the emission with that of standards of known concentration.

The zirconia-based sols (0.2 to 0.3 gram) were accurately weighed into a centrifuge tube. Deionized water (40 ml) and hydrochloric acid (2 ml concentrated hydrochloric acid (37-38 percent; obtained from EMD Chemicals, Gibbstown, N.J. under trade designation EMD OMNITRACE)) was added. The solutions were then diluted to a total of 50 grams with deionized water. Duplicates of each sample were prepared. Two blanks containing just the hydrochloric acid and water were also prepared. Further dilutions were prepared as necessary to bring the concentration of the samples within the calibration range. The samples and blanks were analyzed on an Inductively Coupled Plasma optical emission spectrometer (obtained under the trade designation "PERKIN ELMER OPTIMA 4300" from Perkin Elmer, Shelton, Conn.). The instrument was calibrated using multi-element standards. The standards, which were obtained from solutions that are available from High Purity Standards, Charleston, S.C., had concentrations of 0.2 ppm, 0.5 ppm, and 1.5 ppm (microgram per milliliter). The results were normalized to the amount of zirconia in the starting zirconia-based sol.

Photon Correlation Spectroscopy (PCS)

Particle size measurements were made using a light scattering particle sizer equipped with a red laser having a 633 nm wavelength of light (obtained under the trade designation "ZETA SIZER-NANO SERIES, MODEL ZEN3600" from Malvern Instruments Inc., Westborough, Mass.). Each sample was analyzed in a one centimeter square polystyrene sample cuvette. The sample cuvette was filled with about 1 gram of deionized water, and then a few drops (about 0.1 gram) of the zirconia-based sol were added. The composition (e.g., sample) within each sample cuvette was mixed by drawing the composition into a clean pipette and discharging the composition back into the sample cuvette several times. The sample cuvette was then placed in the instrument and equilibrated at 25° C. The instrument parameters were set as follows: dispersant refractive index 1.330, dispersant viscosity 1.0019 MPa-second, material refractive index 2.10, and material absorption value 0.10 units. The automatic size-measurement procedure was then run. The instrument automatically adjusted the laser-beam position and attenuator setting to obtain the best measurement of particle size.

The light scattering particle sizer illuminated the sample with a laser and analyzed the intensity fluctuations of the light scattered from the particles at an angle of 173 degrees. The method of Photon Correlation Spectroscopy (PCS) was used by the instrument to calculate the particle size. PCS uses the fluctuating light intensity to measure Brownian motion of the particles in the liquid. The particle size is then calculated to be the diameter of sphere that moves at the measured speed.

The intensity of the light scattered by the particle is proportional to the sixth power of the particle diameter. The Z-average size or cumulant mean is a mean calculated from the intensity distribution and the calculation is based on assumptions that the particles are mono-modal, mono-disperse, and spherical. Related functions calculated from the fluctuating light intensity are the Intensity Distribution and its mean. The mean of the Intensity Distribution is calculated based on the assumption that the particles are spherical. Both the Z-average size and the Intensity Distribution mean are more sensitive to larger particles than smaller ones.

The Volume Distribution gives the percentage of the total volume of particles corresponding to particles in a given size range. The volume-average size is the size of a particle that corresponds to the mean of the Volume Distribution. Since the volume of a particle is proportional to the third power of the diameter, this distribution is less sensitive to larger particles than the Z-average size. Thus, the volume-average will typically be a smaller value than the Z-average size.

Field Emission Scanning Electron Microscopy (FESEM)

Samples were prepared by depositing a thin layer of Au—Pd to make the samples conductive. The microscope used was a field emission scanning electron microscope obtained under the trade designation "HITACHI S-4700" from Hitachi Ltd., Maidenhead, UK. Images (i.e., electron micrographs) were obtained while operating at 3.0 or 5.0 kilovolts and with a magnification of 30,000 or 70,000 times.

Line Intercept Analysis

FESEM micrographs with 70,000 times magnification were used for grain size measurement. Three or four micrographs taken from different areas of the sintered body were used for each sample. Ten horizontal lines, which were spaced at roughly equal intervals across the height of each micrograph, were drawn. The number of grain boundary intercepts observed on each line were counted and used to calculate the average distance between intercepts. The average distance for each line was multiplied by 1.56 to determine the grain size and this value was averaged over all the lines for all micrographs of each sample.

Method for Measuring N2 Sorption Isotherms, BET Surface Area, Pore Volume, Average Connected Pore Size and Porosity The samples were nm on either on a QUANTACHROME AUTOSORB-1 BET Analyzer" (Quantachrome Instruments, Boynton Beach, Fla.) or a BELSORP-mini instrument (BEL Japan Inc., Osaka, Japan). The samples were weighed and outgassed at 200° C. for two days then subjected to a N2 sorption process with an appropriate number and distribution of measurement points, e.g. 55 adsorb points and 20 desorb points from a $P/P_o$ range $1\times10^6$ to 1 and back to 0.05 giving full isotherms. The specific surface area S was calculated by the BET method (Details regarding calculation see Autosorb-1 Operating Manual Ver. 1.51 IV. Theory and Discussion, Quantachrome Instruments, Inc.). The total pore volume $V_{liq}$ is derived from the amount of vapor adsorbed at a relative pressure close to unity ($P/P_o$ closest to 1), by assuming that the pores are then filled with liquid adsorbate (Details regarding calculation see Autosorb-1 Operating Manual Ver. 1.51 IV. Theory and Discussion, Quantachrome Instruments, Inc.). The average pore diameter (d) is calculated from the surface area (S) and the total pore volume ($V_{liq}$):

$$d = \frac{4Vliq}{S}$$

Method for Measuring Weight Percent Solids

The weight percent solids were determined by drying a sample weighing 3-6 grams at 120° C. for 30 minutes. The percent solids can be calculated from the weight of the wet sample (i.e., weight before drying, $weight_{wet}$) and the weight of the dry sample (i.e., weight after drying, $weight_{dry}$) using the following equation.

Wt-% solids=100 ($weight_{dry}$)/$weigh_{wet}$

Method for Measuring Oxide Content of a Solid

The oxide content of a sol sample is determined by measuring the percent solids content as described in the "Method for Measuring Weight Percent Solids" then measuring the oxide content of those solids as described in this section.

The oxide content of a solid was measured via thermal gravimetric analysis (obtained under the trade designation "TGA Q500" from TA Instruments, New Castle, Del.). The solids (about 50 mg) were loaded into the TGA and the temperature was taken to 900° C. The oxide content of the solid is equal to the residual weight after heating to 900° C.

Method for Measuring Biaxial Flexure Strength

The strength of various zirconia bodies was measured using the biaxial flexure strength.

Samples were circular sintered wafers, roughly 12 mm in diameter and 1.5 mm thick. The wafers were ground to different thickness on a polishing wheel using a 45 micrometer metal bonded diamond disc (identified as Part No: 156145 from Buehler, Lake Bluff, Ill.), followed by 30 micrometer and 9 micrometer diamond lapping film (obtained under the trade designation "3M DIAMOND LAPPING FILM 668X" from 3M Company, St. Paul, Minn.) and finally 3 micrometer diamond suspension (obtained under the trade designation "METADI DIAMOND SUSPENSION" from Buehler) on a polishing cloth (obtained under the trade designation "TEXMET POLISHING CLOTH" from Buehler). A minimum of 4 samples were measured to determine the average strength.

The polished side of each wafer was centered on a support consisting of three steel balls, 3 mm diameter, spaced at 120° intervals, on a circle with a diameter of 8 mm. The support and wafer were placed in a fixture with a vertical punch that rested on the center of the upper, unpolished side of the wafer. The punch diameter in contact with the wafer was 1.8 mm. The fixture was loaded in a universal test machine (identified as "Series 1101" from Applied Test Systems, Inc., Butler, Pa.). The punch was pushed into the wafer at a rate of 0.2 mm per min. until the wafer fractured. The load at fracture was recorded. The strength value was calculated from the following formula:

$$S=-0.2387P(X-Y)/d^2$$

Where:
P=load at fracture in Newtons
$X=(1+v)\ln(r_2/r_3)^2+[(1-v)/2](r_2/r_3)^2$
$Y=(1+v)[1+\ln(r_1/r_3)^2]+(1-v)(r_1/r_3)^2$
In which:
v=Poisson's Ratio (assumed a value of 0.23)
$r_1$=the radius of the support circle in mm
$r_2$=the radius of the upper punch contact in mm
$r_3$=the radius of the sample wafer in mm
d=the thickness of the sample wafer in mm Volume Percent Metal Oxide The volume percent of oxide present in an aerogel or a calcined metal oxide was determined by back-calculation using shrinkage data and assuming that the final sintered body was a 1 cm cube, 100% dense. The total volume of the aerogel or calcined metal oxide is then $(Vt)=[1/(1-S)]^3$, where S is the fractional shrinkage from the aerogel or calcined state to the final sintered material. The volume of metal oxide is the volume of the sintered cube (V)=1. The percent metal oxide (Vol %)=$(1/V_t)100$.

Method for Measuring Archimedes' Density

The density of the sintered material was measured by an Archimedes technique. The measurements were made on a precision balance (identified as "AE 160" from Mettler Instrument Corp., Hightstown, N.J.) using a density determination kit (identified as "ME 33360" from Mettler Instrument Corp.). In this procedure the sample was first weighed in air (A), then immersed in water (B). The water was distilled and deionized. One drop of a wetting agent (obtained under trade designation "TERGITOL-TMN-6" from Dow Chemical Co., Danbury, Conn.) was added to 250 ml of water. The density was calculated using the formula $p=(A/(A-B)) \rho_0$, where $\rho_0$ is the density of water.

The relative density can be calculated by reference to the theoretical density ($\rho_t$) of the material, $\rho_r=(\rho/\rho_t)100$.

Total Transmittance, Diffuse Transmittance, Haze

Figure 2:
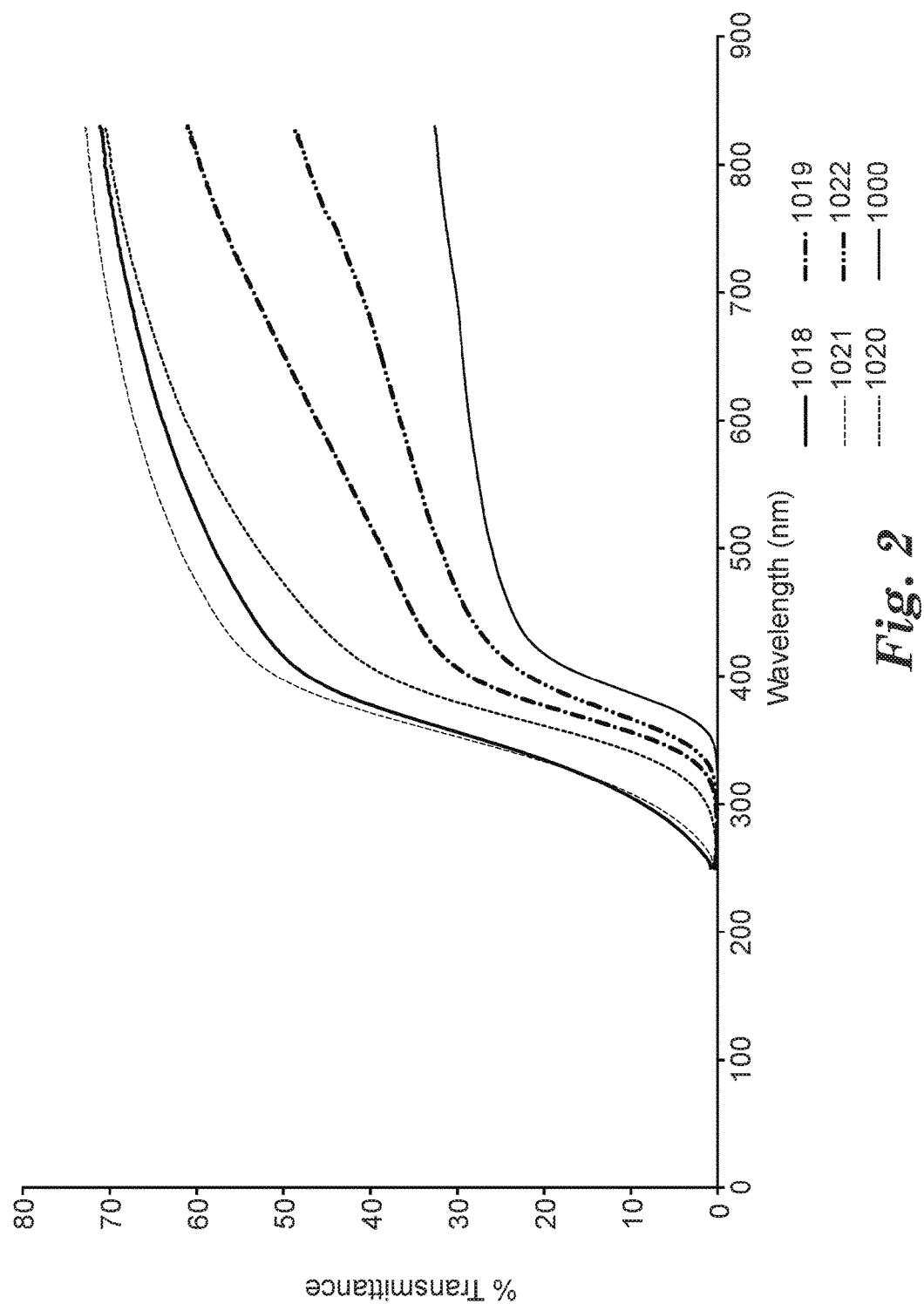
FIG. 2 is a total transmittance versus wavelength for various Examples and Comparative Examples.
Figure 3:
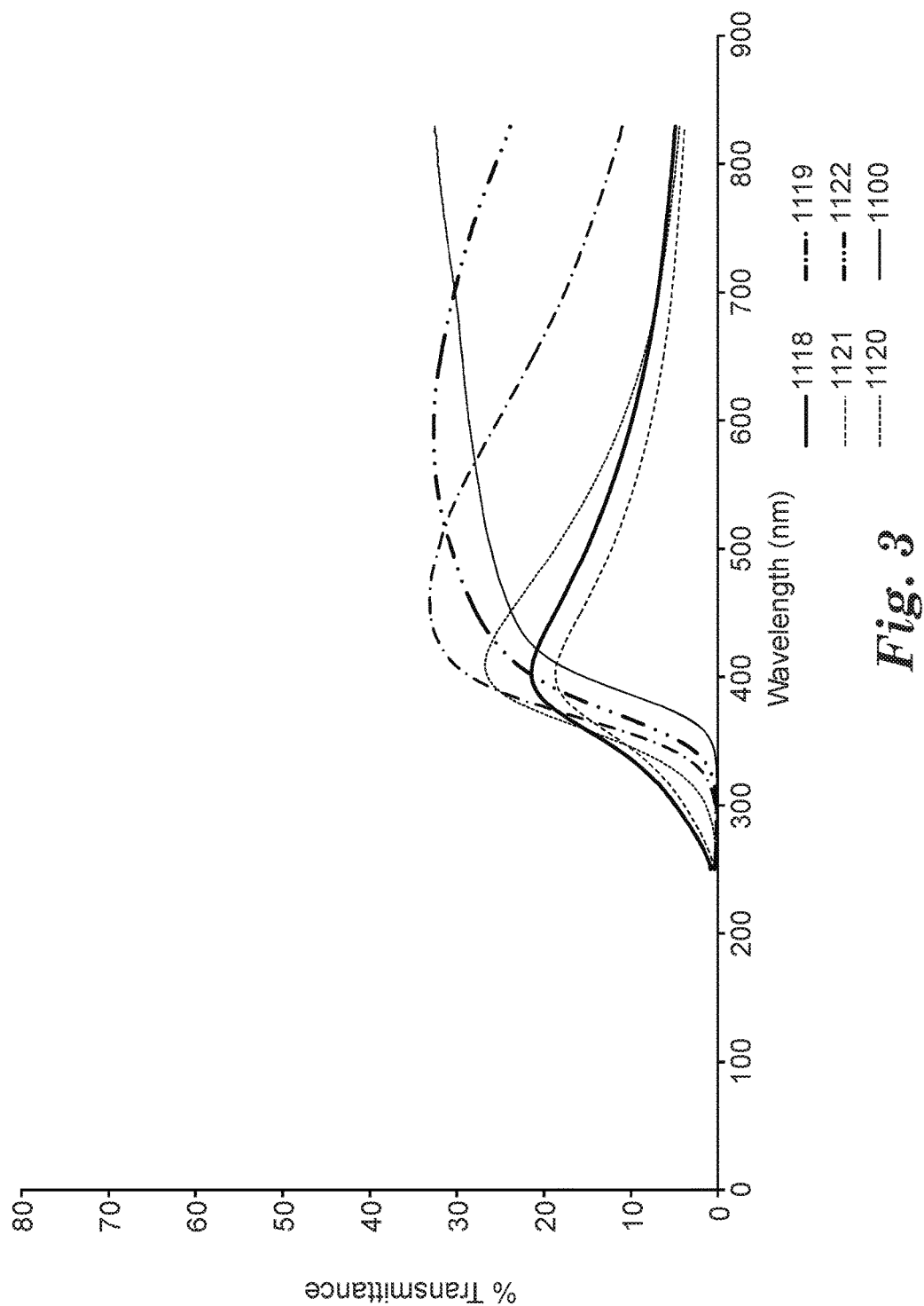
FIG. 3 is a diffuse transmittance versus wavelength for various Examples and Comparative Examples.

The samples were measured using a spectrophotometer (obtained under the trade designation "PERKIN ELMER LAMBDA 1050" from Perkin Elmer Corporation, Waltham, Mass.) fitted with a integrating sphere accessory. This sphere was 150 mm (6 inches) in diameter and complied with ASTM methods E903, D1003, E308, et al. as published in "ASTM Standards on Color and Appearance Measurement", Third Edition, ASTM, 1991. The values of Total (TLT) and Diffuse (DLT) Light Transmittance corresponding to Commission Internationale de L'Eclairage (CIE) Light Source C with a wavelength range between 380 nm and 780 nm were calculated from the sum-product of the TLT and DLT transmitted spectra using the CIE weighting table. The recorded TLT and DLT spectra used for the calculations were measured from 250 nm to 830 nm and are shown in FIGS. 2 and 3.

% Haze was calculated according to ASTM D1003 (CIE Source C) as follows:

% Haze=(% DLTs/% TLTs)*100, where TLTs is the TLT of the sample, DLTs is the DLT of the sample.

A small spot accessory was used with center focus so that the area of the sample illuminated at the front sample port was about the same as the area illuminated at the rear sample port (where white plate or light trap were used to record T100 and T0 spectra, respectively). The test parameters were as follows:

Scan Speed: 102 nm/min (approximately)
UV-Vis Integration: 0.56 ms/pt
Data Interval: 1 nm
Slit Width: 5 nm
Mode: % Transmission (Total and Diffuse)

Hydrolytic Stability Test

The hydrolytic stability of some Examples was tested generally according to ISO 13356:2008, entitled "Implants for surgery—Ceramic Materials Based On Yttria-Stabilized Tetragonal Zirconia (Y-TZP)", chapter 4.8 (2008).

More specifically, sintered samples were placed in an autoclave and exposed to saturated steam at 135° C. under a pressure of 0.2 MPa for 5 hours.

After the 5 hour exposure to saturated steam at 135° C. under a pressure of 0.2 MPa, the crystal phases of the sample surface were measured with x-ray diffraction equipment with a Bragg-Brentano geometry (obtained under the trade designation "BRUKER D8 DISCOVER" from Bruker AXS GmbH, Karlsruhe, Germany) with quantitative phase analysis based on the Rietveld method (software obtained under the trade designation "BRUKER TOPAS" from Bruker AXS GmbH, Karlsruhe, Germany) to determine the amount of monoclinic phase.

To pass this Hydrolytic Stability Test, not more than 25% monoclinic phase is permitted after being subjected to the 5 hour exposure to saturated steam at 135° C. under a pressure of 0.2 MPa.

Materials Used

TABLE 1

| Material name or abbreviation | Description |
|---|---|
| MEEAA | 2-(2-(2-Methoxyethoxy) Ethoxy) Acetic Acid obtained from Aldrich Chemical Company, Milwaukee, WI |
| Zirconium acetate | An aqueous solution of zirconium acetate containing nominally 16.3weight percent Zr obtained from Magnesium Elektron, Inc., Flemington, NJ. The aqueous solution was exposed to an ion exchange resin (obtained under the trade designation "AMBERLYTE IR 120" from Rohm and Haas Company, Philadelphia, PA) before use (oxide content 21.85 wt. %) |
| DI water | De-ionized water |
| Yttrium acetate | Yttrium (III) acetate tetrahydrate obtained from AMR Technologies Inc., Toronto, Canada (oxide content 33.4 wt. %) |
| 1-Methoxy-2-propanol | An alcohol obtained from Aldrich Chemical Company |
| 2-Hydroxyethyl methacrylate (HEMA) | An acrylate monomer obtained from Aldrich Chemical Company |
| Triethylamine | A base obtained from Aldrich Chemical Company |
| Lanthanum Acetate | Lathanum (III) acetate hydrate obtained from Alfa Aesar, Ward Hill, MA (oxide content 45.5 wt. %) |

TABLE 1-continued

| Material name or abbreviation | Description |
|---|---|
| Acrylamide | Acrylamide obtained from Alfa Aesar |
| 1-vinyl-2-pyrrolidione | 1-vinyl-2-pyrrolidione obtained from Alfa Aesar |
| 2,2'-Azobis(2-methylbutyronitrile), ("VAZO 67") | 2,2'-Azobis(2-methylbutyronitrile), obtained from E. I. du Pont de Nemours and Company, Wilmington, DE under the trade designation "VAZO 67" |
| Ethoxylated Pentaerythritol Tetraacrylate ("SR454") | Ethoxylated Pentaerythritol Tetraacrylate, obtained from Sartomer Company Inc., Exton, PA, under the trade designation "SR454" |
| Ethoxylated Pentaerythritol Tetraacrylate ("SR494") | Ethoxylated Pentaerythritol Tetraacrylate, obtained from Sartomer Company Inc., under the trade designation "SR494" |
| Polyethylene Glycol (400) dimethacrylate ("SR603") | Polyethylene Glycol (400) dimethacrylate, obtained from Sartomer Company Inc., under the trade designation "SR603" |
| Ethoxylated (9) Trimethylolpropane Triacrylate ("SR502") | Ethoxylated (9) Trimethylolpropane Triacrylate Obtained from Sartomer Company Inc., under the trade designation "SR502" |
| Ethoxylated (15) Trimethylolpropane Triacrylate ("SR9035") | Ethoxylated (15) Trimethylolpropane Triacrylate Obtained from Sartomer Company Inc., under the trade designation "SR9035" |
| Butyl Acrylate | Butyl Acrylate obtained from Alfa Aesar |

Preparation of $ZrO_2$ (95.7 mol %)/$Y_2O_3$ (2.3 mol %)/$La_2O_3$ (2 mol %) Sol (Sol T1)

Sol compositions are reported in mole percent inorganic oxide. The following hydrothermal reactor was used for preparing Sol T1 and all other sols in this application.

The hydrothermal reactor was prepared from 15 meters of stainless steel braided smooth tube hose (0.64 cm inside diameter, 0.17 cm thick wall; obtained under the trade designation "DUPONT T62 CHEMFLUOR PTFE" from Saint-Gobain Performance Plastics, Beaverton, Mich.). This tube was immersed in a bath of peanut oil heated to the desired temperature. Following the reactor tube, a coil of an additional 3 meters of stainless steel braided smooth tube hose ("DUPONT T62 CHEMFLUOR PTFE"; 0.64 cm I.D., 0.17 cm thick wall) plus 3 meters of 0.64 cm stainless-steel tubing with a diameter of 0.64 cm and wall thickness of 0.089 cm that was immersed in an ice-water bath to cool the material and a backpressure regulator valve was used to maintain an exit pressure of 2.76 MPa.

A precursor solution was prepared by combining the zirconium acetate solution (2,000 grams) with DI water (1000 grams). Yttrium acetate (57.6 grams) was added while mixing until full dissolution. Lanthanum acetate (53.1 grams) and D.I water (600 grams) were added and mixed until fully dissolved. The solids content of the resulting solutions was measured gravimetrically (120° C./hr. forced air oven) to be 21.9 wt. %. D.I. water (567 grams) was added to adjust the final concentration to 19 wt. %. This procedure was repeated four times of give a total of about 17,100 grams of precursor material. The resulting solution was pumped at a rate of 11.48 ml/min. through the hydrothermal reactor. The temperature was 225° C. and the average residence time was 42 minutes. A clear and stable zirconia sol was obtained.

Preparation of $ZrO_2$ (88 mol %)/$Y_2O_3$ (12 mol %) Sol (Sol C2)

A precursor solution was prepared by combining the zirconium acetate solution (2,000 grams) with DI water (2000 grams). Yttrium acetate (326.8 grams) was added while mixing. The solids content of the resulting solutions was measured gravimetrically (120° C./hr. forced air oven) to be 22.2 wt. %. D.I. water (728 grams) was added to adjust the final concentration to 19 wt. %. This procedure was repeated three times to produce a total of about 15,100 grams of precursor solution. The resulting solution was pumped at a rate of 11.48 ml/min. through the hydrothermal reactor. The temperature was 225° C. and the average residence time was 42 minutes. A clear and stable zirconia sol was obtained.

Table 2 (below) is a summary of the compositions and the process conditions used for other sols produced in a similar manner to Sol T1.

TABLE 2

| Sol | $ZrO_2$, mol % | $Y_2O_3$, mol % | $La_2O_3$, mol % | Residence time, min. | Temperature, ° C. |
|---|---|---|---|---|---|
| T1 | 95.7 | 2.3 | 2.0 | 42 | 225 |
| T2 | 95.7 | 2.3 | 2.0 | 42 | 225 |
| C1 | 88 | 12 | 0 | 42 | 225 |
| C2 | 88 | 12 | 0 | 42 | 225 |
| C3 | 88 | 12 | 0 | 42 | 225 |
| C4 | 88 | 12 | 0 | 42 | 225 |
| B1 | 95 | 5 | 0 | 42 | 225 |
| S1 | 97.7 | 2.3 | 0 | 42 | 215 |
| S2 | 97.7 | 2.3 | 0 | 42 | 215 |
| S3 | 97.7 | 2.3 | 0 | 42 | 215 |
| S4 | 97.7 | 2.3 | 0 | 42 | 215 |
| A1 | 95 | 3.0 | 2.0 | 42 | 225 |

Sol Concentration and Diafiltration

The resulting sols were concentrated (20-35 wt. % solids) first via ultrafiltration using a membrane cartridge (obtained under the trade designation "M21S-100-01P" from Spectrum Laboratories Inc., Rancho Dominguez, Calif.), and then via constant volume diafiltration using the same membrane cartridge. The resulting sol was then further concentrated via rotary evaporation.

The diafiltration process resulted in some loss of yttrium and lanthanum from the zirconia sol. ICP was used to determine the following data.

A sol prepared at 97.5/2.3/2 $ZrO_2$:$Y_2O_3$:$La_2O_3$ resulted in a sol with the following composition 96.6/2.2/1.3 $ZrO_2$:$Y_2O_3$:$La_2O_3$.

A sol prepared with an 88/12 $ZrO_2$/$Y_2O_3$ composition resulted in a sol with the following composition 90.7/9.3 $ZrO_2$:$Y_2O_3$.

A sol prepared with a 97.7/2.3 $ZrO_2$/$Y_2O_3$ composition resulted in a sol with the following composition 97.7/2.3 $ZrO_2$:$Y_2O_3$.

A sol prepared with a 95/5 $ZrO_2$/$Y_2O_3$ composition resulted in a sol with the following composition 95.6/4.4 $ZrO_2$:$Y_2O_3$.

COMPARATIVE EXAMPLE A

A partially sintered zirconia-based material (60 mm zirconia block; obtained under the trade designation "LAVA" 3M ESPE, St. Paul, Minn.) was removed from a 3-unit frame (obtained under the trade designation "LAVA" from 3M ESPE). The cylindrical block was diced into wafers 1-2 millimeter in thickness with a low speed diamond saw using de-ionized water as a lubricant. The wafers were dried at 60° C. and then sintered in a rapid temperature furnace (obtained from CM Furnaces Inc., Bloomfield, N.J.) by heating at a rate of 7.5° C./minute to 1500° C.; holding at 1500° C. for 2 hours; and cooling at 10° C./minute to 20° C.

Sintered wafers were ground to different thicknesses on a polishing wheel using a 45 micrometer metal bonded diamond disc (obtained as Part No: 156145 from Buehler), followed by 30 micrometer and 9 micrometer diamond lapping film ("3M DIAMOND LAPPING FILM 668X") and finally 3 micrometer diamond suspension ("METADI DIAMOND SUSPENSION") on a polishing cloth ("TEXMET POLISHING CLOTH"). Each wafer was mounted in a lapping fixture (obtained as Model 150 from South Bay Technology, Inc., Temple City, Calif.) during grinding and polishing to maintain flat and parallel faces. Wafers were bonded to the lapping fixture using a hot-melt adhesive (obtained under trade designation "QUICKSTICK 135" from South Bay Technology, Inc., Temple City, Calif.). One side of each wafer was ground and polished, then the wafer was remounted and the other side was ground and polished. Polishing to finer finishes had negligible impact on the measured transmission. Wafers with the following thickness values in millimeters were prepared; 1.00, 0.85, 0.60, 0.50, 0.45, and 0.38.

The optical density (OD) of each wafer was measured on a densitometer (obtained under the trade designation "TD504" from Macbeth, Newburgh, N.Y.). The total transmission (T) was calculated using the formula:

$$OD = \log_{10}(1/T)$$

The total transmission was then plotted as a function of wafer thickness (t) and found to form a near linear plot with the following equation:

$$T = -24.249t + 52.704$$

This equation was used to calculate the Lava reference transmission at any desired thickness in the range.

Example wafers were ground and polished and the total transmission measured following the same procedures used for the Lava wafers. The ratio of this value to the Lava value ($T/T_L$) calculated for the same thickness was used for comparative purposes.

To measure the total transmittance, diffuse transmittance, and haze of Comparative Example A, a partially sintered zirconia-based material (block 60 mm; "LAVA") was removed from a 3-unit frame ("LAVA"). A wafer 2 mm thick was diced from the block with a low speed diamond saw using de-ionized water as a lubricant. The wafer was dried at 90-125° C.

The wafer was set on a bed of zirconia beads in an alumina crucible, covered with alumina fiberboard then sintered in air according to the following schedule in a rapid temperature furnace (obtained from CM Furnaces Inc.): i—heat from 20° C. to 1500° C. at 450° C./hr. rate; ii—hold at 1500° C. for 2 hours; and iii—cool down from 1500° C. to 20° C. at 600° C./hr. rate.

The sintered wafer was polished on both faces using polishing equipment comprised of an electrically driven head obtained under the trade designation ("VECTOR POWER HEAD" from Buehler) and a grinder-polisher (obtained under the trade designation "BETA GRINDER-POLISHER" from Buehler). First the sample was ground flat using a 45 micrometer metal bonded diamond disc (identified as Part No: 156145 from Buehler). Then 30 micrometer diamond lapping film ("3M DIAMOND LAPPING FILM 668X") was used until the majority of the 45 micrometer scratches were removed. Then 9 micrometer diamond lapping film ("3M DIAMOND LAPPING FILM 668X") was used until the majority of the 30 micrometer scratches were removed. Next the sample was polished using 3 micrometer diamond suspension ("METADI DIA- MOND SUSPENSION") on a polishing cloth ("TEXMET POLISHING CLOTH") until the majority of the 9 micrometer scratches were removed. Finally the sample was polished using 0.25 micrometer diamond suspension ("METADI DIAMOND SUSPENSION") on a polishing cloth ("TEXMET POLISHING CLOTH") until the majority of the 3 micrometer scratches were removed. The wafer was mounted in a lapping fixture (Model 150, South Bay Technology, Inc.) during grinding and polishing to maintain flat and parallel faces. The wafer was bonded to the lapping fixture using a hot-melt adhesive ("QUICKSTICK 135"). One side of the wafer was ground and polished, then the wafer was remounted and the other side was ground and polished.

The total transmittance was 27.9%, the diffuse transmittance was 27.7%, and the haze was 99.4%, measured using the spectrophotometer procedure described earlier. The TLT and DLT spectra are designated in FIGS. 2 and 3 as 1000 and 1100, respectively. The sample thickness was 0.99 mm.

To measure the biaxial flexural strength of Comparative Example A, a partially sintered zirconia-based material (block 60 mm; "LAVA") was removed from a 3-unit frame ("LAVA"). The diameter of the cylindrical block was ground down to a diameter of 18 mm using a 45 micrometer metal bonded diamond disc (identified as Part No: 156145 from Buehler). The reduced block was diced into wafers 1.1 mm in thickness with a low speed diamond saw using de-ionized water as a lubricant. The wafers were dried at 60° C.

The wafers were set on a bed of zirconia beads in an alumina crucible, covered with alumina fiberboard then sintered in air according to the following schedule in a rapid temperature furnace (CM Furnaces Inc.): i—heat from 20° C. to 1500° C. at 450° C./hr. rate; ii—hold at 1500° C. for 2 hours; and iii-cool down from 1500° C. to 20° C. at 600° C./hr. rate.

This produced wafers of about the same dimensions as the materials described in the examples. It was then possible to use the same fixture geometry for comparative strength measurements.

The wafers were polished on one face using a 12 open face lapping machine (obtained under the trade designation "LAPMASTER" from Lapmaster International Limited, Mt. Prospect, Ill.) for all but the final polishing step. The samples were all adhered to a sample plate and were then ground flat using 20 micrometer diamond tile (obtained under the trade designation "3M TRIZACT DIAMOND TILE" from 3M Company) at a speed of 30 rpm. The abrasive was then switched to 9 micrometer diamond tile (obtained under the trade designation "3M TRIZACT DIAMOND TILE" from 3M Company) and grinding continued at 30 rpm until the majority of the 20 micrometer scratches were removed. The abrasive was then switched to 3 micrometer diamond tile (obtained under the trade designation "3M TRIZACT DIAMOND TILE" from 3M Company) and grinding continued at 30 rpm until the majority of the 9 micrometer scratches were removed. The final polish was done using polishing equipment comprised of an electrically driven head ("VECTOR POWER HEAD") and a grinder-polisher ("BETA GRINDER-POLISHER") and 3 micrometer diamond suspension ("METADI DIAMOND SUSPENSION") on a polishing cloth ("TEXMET POLISHING CLOTH") until the majority of the scratches were removed.

The biaxial flexure strength of 15 wafers was measured using the procedure described earlier. The average value was 1101 MPa.

EXAMPLE 1 and 2

To prepare Example 1, Sol S1 was diafiltered and concentrated as described above for Sol T1. The resulting sol was 55.4 wt. % $ZrO_2/Y_2O_3$ and 5.65 wt % acetic acid. The sol (200 grams) was charged to a 500 ml round bottom (RB) flask. Ethanol (60.6 grams), acrylic acid (11.5 grams), and HEMA (5.9 grams) were added to the flask. 2,2'-azobis(2-methylbutyronitrile) ("VAZO 67") (0.6 gram) was added and the contents stirred for 4 hours. The contents of the flask were then purged with $N_2$ gas for 6 minutes. The sample (translucent and low viscosity) was charged to cylindrical containers (29 mm diameter). Each container was about 18 mlin volume and each was sealed on both ends (very little air gap was left between the top and liquid). The samples were allowed to stand about 1 hour then placed in an oven to cure (50° C., 4 hours). This results in a clear translucent blue gel. The gel was removed from the container and placed in a 473 mlwide mouth jar. The jar was filled with ethanol (denatured). The sample was soaked for 24 hr then the ethanol was replaced with fresh ethanol. The sample was soaked for 24 hr then the ethanol was replaced with a third batch of fresh ethanol. The sample was allowed to soak until the supercritical extraction was done. The above manipulations were done minimizing the amount of time the gel was exposed to the air.

To prepare Example 2, Sol S2 was diafiltered and concentrated as described above for Sol T1. The resulting sol was 55.8 wt % $ZrO_2/Y_2O_3$ and about 5.5 wt % acetic acid. The sol (195.6 grams) was charged to a 500 ml RB flask. Ethanol (60.6 grams), acrylic acid (11.5 grams) and HEMA (5.9 grams) were added to the flask. 2,2'-azobis(2-methylbutyronitrile) ("VAZO 67") (0.60 gram) was added and the contents stirred for 4 hours. The contents of the flask were then purged with $N_2$ gas for 12.5 minutes). The sample (translucent and low viscosity) was charged to cylindrical containers (29 mm diameter). Each container was about 18 ml in volume and each was sealed on both ends (very little air gap was left between the top and liquid). The samples were allowed to stand about 1 hour then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

Extraction Process

The wet $ZrO_2$-based gels of Examples 1 and 2 were removed separately from the ethanol bath, weighed, placed individually inside small canvas pouches, and then stored briefly in another ethanol bath. The wet weight of Example 1 was 19.9 grams. The wet weight of Example 2 was 23 grams. About 790 ml of 200-proof ethanol was added to the 10-1 extractor of a laboratory-scale supercritical fluid extractor unit designed by and obtained from Thar Process, Inc., Pittsburgh, Pa. The canvas bags containing the wet zirconia-based gels were transferred from the ethanol bath into the 10-1 extractor so that the wet gels were completely immersed in the liquid ethanol inside the jacketed extractor vessel, which was heated and maintained at 60° C. After the extractor vessel lid was sealed in place, liquid carbon dioxide was pumped by a chilled piston pump (setpoint: 12.5° C.) through a heat exchanger to heat the $CO_2$ to 60° C. and into the 10-L extractor vessel until an internal pressure of 13.3 MPa was reached. At these conditions, carbon dioxide is supercritical. Once the extractor operating conditions of 13.3 MPa and 60° C. were met, a needle valve regulated the pressure inside the extractor vessel by opening and closing to allow the extractor effluent to pass through a porous 316L stainless steel frit (obtained from Mott Corporation, New Britain, Conn., as Model #1100S-5.480 DIA-.062-10-A), then through a heat exchanger to cool the effluent to 30° C., and finally into a 5-L cyclone separator vessel that was maintained at room temperature and pressure less than 5.5 MPa, where the extracted ethanol and gas-phase $CO_2$ were separated and collected throughout the extraction cycle for recycling and reuse. Supercritical carbon dioxide ($scCO_2$) was pumped continuously through the 10-L extractor vessel for 7 hours from the time the operating conditions were achieved. After the 7-hour extraction cycle, the extractor vessel was slowly vented into the cyclone separator over 16 hours from 13.3 MPa to atmospheric pressure at 60° C. before the lid was opened and the dried canvas pouches containing the aerogels were removed. The dry aerogels were removed from their canvas pouches, weighed, and transferred into a 237 ml glass jar packed with tissue paper for storage. The dry Example 1 aerogel was semi-translucent with a bluish tint and weighed 10.4 grams, corresponding to an overall weight loss during the supercritical extraction process of 47.7%. The dry Example 2 aerogel was semi-translucent with a bluish tint and weighed 12.5 grams, corresponding to an overall weight loss during the supercritical extraction process of 45.7%.

Organic Burnout and Pre-sinter Process

The extracted aerogel sample of Examples 1 from above was removed from its closed container and its weight, diameter and height were measured. The sample was set on a bed of zirconia beads in an unglazed porcelain crucible, covered with an alumina fiberboard then fired in air according to the following schedule in a high temperature furnace (obtained under the trade designation "THERMOLYNE TYPE 46200" from Thermo Fischer Scientific, Inc., Waltham, Mass.): i—heat from 20° C. to 225° C. at 18° C./hr. rate; ii—hold at 225° C. for 24 hours; iii—heat from 225° C. to 400° C. at 6° C./hr. rate; iv—heat from 400° C. to 600° C. at 18° C./hr. rate; and v—cool down from 600° C. to 20° C. at 600° C./hr. rate.

The sample was set on an alumina fiberboard contained in an alumina crucible, covered with an alumina crucible then fired in air according to the following schedule in a crucible furnace (Model 56724; "LINDBERG/BLUE M 1700° C." from Thermo Fischer Scientific, Inc.): i—heat from 20° C. to 665° C. at 600° C./hr. rate; ii—heat from 665° C. to 800° C. at 120° C./hr rate; and iii—cool down from 800° C. to 20° C. at 600° C./hr. rate.

The sample was then set on a bed of zirconia beads in an alumina crucible, covered with an alumina fiberboard then fired in air according to the following schedule in a crucible furnace (Model 56724; LINDBERG/BLUE M 1700° C.): i—heat from 20° C. to 665° C. at 600° C./hr. rate; ii—heat from 665° C. to 950° C. at 120° C./hr. rate; iii—hold at 950° C. for 2 hours; and iv—cool down from 950° C. to 20° C. at 600° C./hr. rate.

The extracted aerogel of Example 2 and pre-sintered aerogel of Example 1 samples were analyzed to determine the BET surface area, pore size and porosity. The extracted aerogel of Example 2 (which was crack free) had a surface area of 198 m$^2$/g, total pore volume of 0.806 cm$^3$/g and an average pore diameter of 163 Angstroms (Å). The pre-sintered sample of Example 1 had a surface area of 35 m$^2$/g, total pore volume of 0.285 cm$^3$/g and an average pore diameter of 329 A.

EXAMPLE 3

A 277 gram sample of Sol T1 (prepared and diafiltered and concentrated as described above, 29.5 wt. % oxide and 3.2 wt. % acetic acid) was charged to 500 ml round-bottom (RB) flask. Water (127 grams) was removed via rotary evaporation, resulting in a viscous somewhat dry material. Ethanol (45.5 grams), acrylic acid (8.6 grams) and 2-Hydroxyethyl methacrylate (HEMA) (4.4 grams) were added to the flask. The contents were stirred for about 4 hours resulting is a fluid translucent sol. 2,2'-azobis(2-methylbutyronitrile) ("VAZO 67") (0.45 gram) was added and the contents stirred for 5 minutes. The contents of the flask were then purged with $N_2$ gas for 4 minutes. The sample (translucent and low viscosity) was charged to cylindrical containers (29 mm diameter). Each container was about 18 ml in volume and each was sealed on both ends (very little air gap was left between the top and liquid). The samples were allowed to stand for about 1 hour then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hr then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

Extraction Process

The wet $ZrO_2$-based gels of Example 3 were removed separately from the ethanol bath, weighed, placed inside an individual, small canvas pouch, and then stored briefly in another ethanol bath before being loaded into the 10-L extractor vessel. The wet weight of Example 3A was 20.3 grams. The wet weight of Example 3B was 21.5 grams. The wet weight of Example 3C was 15.5 grams. The wet weight of Example 3D was 18.8 grams. For all samples in Example 3, about 800 ml of 200-proof ethanol was added to the 10-L extractor of a laboratory-scale supercritical fluid extractor unit. The canvas bags containing the wet zirconia-based gels were transferred from the ethanol bath into the 10-L extractor so that the wet gels were completely immersed in the liquid ethanol inside the jacketed extractor vessel, which was heated and maintained at 60° C. The Example 3A-3D samples were subjected to the same extraction process as described above for Examples 1 and 2. Afterwards, the dry aerogels were removed from their canvas pouches, weighed, and transferred into individual 237 ml glass jars packed with tissue paper for storage. The dry Example 3A aerogel was semi-translucent with a bluish tint and weighed 10.8 grams, corresponding to an overall weight loss during the supercritical extraction process of 46.8%. The dry Example 3B aerogel was semi-translucent with a bluish tint and weighed 11.3 grams, corresponding to an overall weight loss during the supercritical extraction process of 47.4%. The dry Example 3C aerogel was semi-translucent with a bluish tint and weighed 8.2 grams, corresponding to an overall weight loss during the supercritical extraction process of 47.1%. The dry Example 3D aerogel was semi-translucent with a bluish tint and weighed 9.9 grams, corresponding to an overall weight loss during the supercritical extraction process of 47.3%.

Organic Burnout and Pre-sinter Process

The extracted aerogel samples of Examples 3A-3D from above were removed from their closed containers and the weight, diameter and height were measured. The samples were set on alumina fiberboard supports in an unglazed porcelain crucible, covered with an alumina fiberboard then fired in a high temperature furnace ("THERMOLYNE TYPE 46200") in air according to the following schedule:

i—heat from 20° C. to 225° C. at 18° C./hr. rate; ii—hold at 225° C. for 24 hours; iii—heat from 225° C. to 400° C. at 6° C./hr. rate; iv—heat from 400° C. to 600° C. at 18° C./hr. rate; and v—cool down from 600° C. to 20° C. at 600° C./hr. rate.

After firing (i.e., organic burnout) the samples were crack free. The samples were then set on an alumina fiberboard support in an alumina crucible, covered with an alumina fiberboard then pre-sinter fired in air according to the following schedule in a crucible furnace (Model 56724; "LINDBERG/BLUE M 1700° C."): i—heat from 20° C. to 665° C. at 600° C./hr. rate; ii—heat from 665° C. to 1090° C. at 120° C./hr. rate; and iii—cool down from 1090° C. to 20° C. at 600° C./hr. rate.

After pre-sinter firing the samples were crack free. The cylinders were diced into about 1 mm thick wafers or about 1.5 mm thick wafers. The wafers were ion exchanged by first placing them in a 118 ml glass jar containing distilled water at a depth of about 2.5 cm and then vacuum infiltrating. The water was replaced with about a 2.5 cm depth of 1.0N NH$_4$OH and the wafers were soaked overnight for at least 16 hours. The NH$_4$OH was then poured off and the jar was filled with distilled water. The wafers were then soaked in the distilled water for 1 hour. The water was then replaced with fresh distilled water. This step was repeated until the pH of the soak water was equal to that of fresh distilled water. The wafers were then dried at 90-125° C. for a minimum of 1 hour. The aerogel of Example 3A had 12.2 volume % of oxides while the pre-sintered (at 1090° C.) aerogel of Example 3A had 41.7 volume % of oxides. The Volume percent oxide values were calculated using the method described above.

Sintering Process

The pre-sintered wafers from above were set on an alumina fiberboard in an alumina crucible, covered with an alumina fiberboard then sintered in air according to the following schedule in a crucible furnace (Model 56724: "LINDBERG/BLUE M 1700° C."): i—heat from 20° C. to 1090° C. at 600° C./hr. rate; ii—heat from 1090° C. to 1210° C. at 120° C./hr. rate; iii—hold at 1210° C. for 12 hours; and iv—cool down from 1210° C. to 20° C. at 600° C./hr. rate.

The appearance of the sintered wafers was similar to that of Comparative Example A ("LAVA"). The wafers that were diced to a thickness of 1 mm were polished on both faces. The samples were polished using polishing equipment comprised of an electrically driven head ("VECTOR POWER HEAD") and a grinder-polisher ("BETA GRINDER-POLISHER"). The samples were ground flat on both sides using 30 micrometer diamond lapping film ("3M DIAMOND LAPPING FILM 668X"). Then 9 micrometer diamond lapping film ("3M DIAMOND LAPPING FILM 668X") was used on both sides until the majority of the 30 micrometer scratches were removed. Next, the sample was polished on both sides using 6 micrometers diamond suspension ("METADI DIAMOND SUSPENSION") on a polishing cloth ("TEXMET POLISHING CLOTH") until the majority of the 9 micrometer scratches were removed. Finally, the sample was polished on both sides using 3 micrometer diamond suspension ("METADI DIAMOND SUSPENSION") on a polishing cloth ("TEXMET POLISHING CLOTH") until the majority of the 6 micrometer scratches were removed. The polished samples were then characterized for their T/T$_L$ (measured using the process described above for Comparative Example A), Archimedes' density, and phase composition, as determined by XRD, using the methods described above.

The sample was then set on a bed of zirconia beads in an alumina crucible and thermally etched in air in a rapid temperature furnace (CM Furnaces Inc.), as follows: i—heat from 20° C. to 1160° C. at 450° C./hr. rate; ii—hold at 1160° C. for 1 hour; and iii—cool from 1160° C. to 20° C. at 600° C./hr. rate.

FESEM was done on the thermally etched sample as described in the test method described above. The grain size was determined using the line intercept method described above.

The wafers that were diced to a thickness of 1.5 mm were polished on one face in preparation for biaxial flexural strength testing according to the test method above. The samples were polished using a 12 open face lapping machine ("LAPMASTER") for all but the final polishing step. The samples were all adhered to a sample plate and were then ground flat using 20 micrometer diamond tile ("3M TRIZACT DIAMOND TILE") at a speed of 30 rpm. The abrasive was then switched to 9 micrometer diamond tile ("3M TRIZACT DIAMOND TILE") and grinding continued at 30 rpm until the majority of the 20 micrometer scratches were removed. The abrasive was then switched to 3 micrometer diamond tile ("3M TRIZACT DIAMOND TILE") and grinding continued at 30 rpm until the majority of the 9 micrometer scratches were removed. The final polish was done using Buehler polishing equipment comprised of an electrically driven head ("VECTOR POWER HEAD") and a grinder-polisher ("BETA GRINDER POLISHER") and 3 micrometer METADI diamond suspension ("DIAMOND SUSPENSION") on a polishing cloth ("TEXMET POLISHING CLOTH") until the majority of the scratches were removed. The properties of the sintered wafers are given in Table 3, below.

TABLE 3

| Example | Archimedes Density, g/cm$^3$ | Polished Thickness, mm | Polished T/T$_L$ | Grain Size, nm | Strength, MPa | Phase Composition (XRD) |
|---|---|---|---|---|---|---|
| 3A | 6.10 | 0.74 | 1.07 | | | |
| 3B | 6.10 | 0.69 | 1.06 | 127 | | [ZrO$_2$(T) a = 3.612, c = 5.1 89 A° major] + [La$_2$Zr$_2$O$_7$ minor] |
| 3B | | 0.97 | | | 1080 | |
| 3C | | 0.97 | | | 1080 | |
| 3D | | 0.97 | | | 1080 | |

EXAMPLE 4

A 76.2 gram sample of Sol B1 (prepared and diafiltered and concentrated as described above, 35.8 wt. % oxide and 3.2 wt. % acetic acid) was charged in to a 500 ml RB flask. Water (26.5 grams) was removed via rotary evaporation resulting in a viscous somewhat dry material. Ethanol (15.3 grams), acrylic acid (2.88 grams) and HEMA (1.5 gram) and D.I water (0.4 gram) were added to the flask. The contents were stirred overnight resulting is a fluid translucent sol. 2,2'-azobis(2-methylbutyronitrile) ("VAZO 67") (0.15 gram) was added and stirred until dissolved. The contents of the flask were then purged with N$_2$ gas for 3 minutes). The sample (translucent and low viscosity) was charged to cylindrical containers (29 mm diameter). Each container was about 18 ml in volume and each was sealed on both ends (very little air gap was left between the top and liquid). The samples were allowed to stand for about 1 hour then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

Extraction Process

The wet $ZrO_2$-based gel of Example 4 was removed from the ethanol bath, weighed, placed inside a small canvas pouch, and then stored briefly in another ethanol bath before being loaded into the 10-L extractor vessel. The wet weight of Example 4 was 17.9 grams. About 850 ml of 200-proof ethanol was added to the 10-L extractor of a laboratory-scale supercritical fluid extractor unit. The canvas bag containing the wet zirconia-based gel was transferred from the ethanol bath into the 10-L extractor so that the wet gel was completely immersed in the liquid ethanol inside the jacketed extractor vessel, which was heated and maintained at 60° C. The Example 4 sample was subjected to the same extraction process as described above for Examples 1 and 2 samples. Afterwards, the dry aerogel was removed from its canvas pouch, weighed, and transferred into a 237 ml glass jar packed with tissue paper for storage. The dry Example 4 aerogel was semi-translucent with a bluish tint and weighed 9.6 grams, corresponding to an overall weight loss during the supercritical extraction process of 46.4%.

Organic Burnout and Pre-sinter Process

The extracted aerogel sample of Example 4 from above was removed from its closed container and immediately set on a bed of zirconia beads in an unglazed porcelain crucible, covered with alumina fiberboard then fired in air according to the following schedule in a high temperature furnace ("THERMOLYNE TYPE 46200"): i—heat from 20° C. to 225° C. at 18° C./hr. rate; ii—hold at 225° C. for 24 hours; iii—heat from 225° C. to 400° C. at 6° C./hr. rate; iv—heat from 400° C. to 600° C. at 18° C./hr. rate; v—heat from 600° C. to 1090° C. at 120° C./hr. rate; and vi—cool down from 1090° C. to 20° C. at 600° C./hr. rate.

After firing the sample was crack free. The cylinder was diced into about 2 mm thick wafers. The wafers were ion exchanged by first placing them in a 118 ml glass jar containing distilled water at a depth of about 2.5 cm and then vacuum infiltrating. The water was replaced with about a 2.5 cm depth of 1.0N $NH_4OH$ and the wafers were soaked overnight for 16 hours or longer. The $NH_4OH$ was then poured off and the jar was filled with distilled water. The wafers were soaked in the distilled water for 1 hour. The water was then replaced with fresh distilled water. This step was repeated until the pH of the soak water was equal to that of fresh distilled water. The wafers were then dried at 90-125° C. for a minimum of 1 hour. The pre-sintered at 1090° C. aerogel of Example 4 had 50.4 volume % of oxides as determined by dividing the geometric density of the pre-sintered wafer by the Archimedes density of the sintered wafer and then multiplying by 100.

Sintering Process

A wafer of Example 4 prepared as described above was set on a bed of zirconia beads in an alumina crucible, covered with alumina fiberboard then sintered in air according to the following schedule in a crucible furnace (Model 56724; "LINDBERG/BLUE M 1700° C."): i—heat from 20° C. to 1090° C. at 600° C./hr. rate; ii—heat from 1090° C. to 1250° C. at 120° C./hr. rate; iii—hold at 1250° C. for 2 hours; and iv—cool down from 1250° C. to 20° C. at 600° C./hr. rate.

The wafer was polished on both faces using polishing equipment comprised of an electrically driven head ("VECTOR POWER HEAD") and a grinder-polisher ("BETA GRINDER-POLISHER). The sample was ground flat on both sides using 30 micrometer diamond lapping film ("3M DIAMOND LAPPING FILM 668X"). Then 9 micrometer diamond lapping film ("3M DIAMOND LAPPING FILM 668X") was used on both sides until the majority of the 30 micrometer scratches were removed. Next the sample was polished on both sides using 6 micrometer diamond suspension ("METADI DIAMOND SUSPENSION") on a polishing cloth ("TEXMET POLISHING CLOTH"), until the majority of the 9 micrometer scratches were removed. Finally the sample was polished on both sides using 3 micrometer diamond suspension ("METADI DIAMOND SUSPENSION") on a polishing cloth ("TEXMET POLISHING CLOTH"), until the majority of the 6 micrometer scratches were removed. The polished sample was translucent and lines were distinct when the sample was placed directly on top of them and at a distance. The sample appeared reddish in color in transmitted light and appeared bluish in color in reflected light. The Archimedes density and $T/T_L$ were measured as described in the test methods described above. The sample was then set on a bed of zirconia beads in an alumina crucible and thermally etched in air in a Rapid Temperature Furnace as follows: i—heat from 20° C. to 1200° C. at 450° C./hr. rate; ii—hold at 1200° C. for 0.5 hour; and iii—cool from 1200° C. to 20° C. at 600° C./hr. rate.

FESEM was done on the thermally etched sample as described in the test method described above. The grain size was determined using the line intercept method described in the test method above.

The sintered Example 4 samples had an Archimedes density of 6.06 g/cm$^3$, a polished $T/T_L$ of 1.6 at a polished thickness of 1.2 mm, and an average grain size of 195 nm.

EXAMPLE 5

A 29.3 gram sample of Sol C4 (prepared and diafiltered and concentrated as described above, 27.9 wt. % oxide and 3 wt. % acetic acid) and 196.5 grams of Sol T2 (prepared and diafiltered and concentrated as described above, 23.6 wt. % oxide and 2.26 wt. % acetic acid) was charged in to a 500 ml RB flask. Water (125.8 grams) was removed via rotary evaporation resulting in a viscous somewhat dry material. Ethanol (30.3 grams), acrylic acid (5.8 grams), HEMA (2.95 grams) were added to the flask. The contents were stirred overnight resulting in a fluid translucent sol. 2,2'-azobis(2-methylbutyronitrile) ("VAZO 67") (0.3 gram) was added and stirred until dissolved. The contents of the flask were then purged with $N_2$ gas 6 minutes). The sample (translucent and low viscosity) was charged to cylindrical containers (29 mm diameter). Each container was about 18 ml in volume and each was sealed on both ends (very little air gap was left between the top and liquid). The samples were allowed to stand for about 1 hour then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

Extraction Process

The wet $ZrO_2$-based gels of Example 5 were removed separately from the ethanol bath, weighed, placed individually inside small canvas pouches, and then stored briefly in another ethanol bath before being loaded into the 10-L extractor vessel. The wet weight of Example 5A was 20.5 grams. The wet weight of Example 5B and Example 5C were 19.6 grams and 21.6 grams, respectively. For extraction of all the gels of Example 5A-C, about 850-875 ml of 200-proof ethanol was added to the 10-L extractor of a laboratory-scale supercritical fluid extractor unit. The canvas bags containing the wet zirconia-based gels were transferred from the ethanol bath into the 10-L extractor so that the wet gels were completely immersed in the liquid ethanol inside the jacketed extractor vessel, which was heated and maintained at 60° C. After the extractor vessel lid was sealed in place, liquid carbon dioxide was pumped by a chilled piston pump (setpoint: −12.5° C.) through a heat exchanger to heat the $CO_2$ to 60° C. and into the 10-L extractor vessel until an internal pressure of 11 MPa was reached. At these conditions, carbon dioxide is supercritical. Once the extractor operating conditions of 11 MPa and 60° C. were met, a PID-controlled needle valve regulated the pressure inside the extractor vessel by opening and closing to allow the extractor effluent to pass through a porous 316L stainless steel frit (obtained from Mott Corporation as Model #1100S-5.480 DIA-.062-10-A), then through a heat exchanger to cool the effluent to 30° C., and finally into a 5-L cyclone separator vessel that was maintained at room temperature and pressure less than 5.5 MPa, where the extracted ethanol and gas-phase $CO_2$ were separated and collected throughout the extraction cycle for recycling and reuse. Supercritical carbon dioxide ($scCO_2$) was pumped continuously through the 10-L extractor vessel for 7 hours from the time the operating conditions were achieved. After the 7-hour extraction cycle, the extractor vessel was slowly vented into the cyclone separator over 16 hours from 11 MPa to atmospheric pressure at 60° C. before the lid was opened and the dried canvas pouches containing the aerogel were removed. The dry Example 5 aerogels were removed from their canvas pouches, weighed, and transferred into 237 ml glass jars packed with tissue paper for storage. The dry Example 5A aerogel was semi-translucent with a bluish tint and weighed 10.8 grams, corresponding to an overall weight loss during the supercritical extraction process of 47.3%. The dry Example 5B aerogel was semi-translucent with a bluish tint and weighed 10.2 grams corresponding to an overall weight loss during the supercritical extraction process of 48%. The dry Example 5C aerogel was semi-translucent with a bluish tint and weighed 11.3 grams corresponding to an overall weight loss during the supercritical extraction process of 47.7%.

Organic Burnout and Pre-sinter Process

The extracted Example 5 aerogel samples from above were removed from their closed container and the weight, diameter and height were measured prior to being set on a bed of zirconia beads in an unglazed porcelain crucible, covered with alumina fiberboard then fired in air according to the following schedule in a high temperature furnace ("THERMOLYNE TYPE 46200"): i—heat from 20° C. to 225° C. at 18° C./hr. rate; ii—hold at 225° C. for 24 hour; iii—heat from 225° C. to 400° C. at 6° C./hr. rate; iv—heat from 400° C. to 600° C. at 18° C./hr. rate; v—heat from 600° C. to 1090° C. at 120° C./hr. rate; and vi—cool down from 1090° C. to 20° C. at 600° C./hr. rate.

After firing the samples were crack free. The samples of Example 5 were diced into about 2.5 mm thick wafers. The wafers were ion exchanged by first placing them in a 118 ml glass jar containing distilled water at a depth of about 2.5 cm and then vacuum infiltrating. The water was replaced with about a 2.5 cm depth of 1.0N $NH_4OH$ and the wafers were soaked overnight for 16 hours or longer. The $NH_4OH$ was then poured off and the jar was filled with distilled water. The wafers were soaked in the distilled water for 1 hour. The water was then replaced with fresh distilled water. This step was repeated until the pH of the soak water was equal to that of fresh distilled water. The wafers were then dried at 125° C. for a minimum of 1 hour. The aerogel of Example 5A had 11.8 volume % of oxides while the pre-sintered (at 1090° C.) aerogel of Example 5A had 50.4 volume % of oxides. The aerogel of Example 5B had 12 volume % of oxides while the pre-sintered (at 1090° C.) aerogel of Example 5B had 49.8 volume % of oxides. The aerogel of Example 5C had 11.9 volume % of oxides while the pre-sintered (at 1090° C.) aerogel of Example 5C had 49.7 volume % of oxides. The volume percent oxide values were calculated using the method described above.

Sintering Process

The wafers prepared as described above were set on a bed of zirconia beads in an alumina crucible, covered with alumina fiberboard then sintered in air according to the following schedule in a crucible furnace (Model 56724; ("LINDBERG/BLUE M 1700° C."): i—heat from 20° C. to 1090° C. at 600° C./hr. rate; ii—heat from 1090° C. to 1250° C. at 120° C./hr. rate; iii—hold at 1250° C. for 2 hours; and iv—cool down from 1250° C. to 20° C. at 600° C./hr. rate.

The 1 mm thick Example 5A sample wafer was polished on both faces using Buehler polishing equipment comprised of an electrically driven head ("VECTOR POWER HEAD") and a grinder-polisher ("BETA GRINDER-POLISHER"). The sample was ground flat on both sides using 30 micrometer diamond lapping film ("3M DIAMOND LAPPING FILM 668X"). Then 9 micrometer diamond lapping film ("3M DIAMOND LAPPING FILM 668X") was used on both sides until the majority of the 30 micrometer scratches were removed. Next the sample was polished on both sides using 6 micrometer diamond suspension ("METADI DIAMOND SUSPENSION") on a polishing cloth ("TEXMET POLISHING CLOTH") until the majority of the 9 micrometer scratches were removed. Finally, the sample was polished on both sides using 3 micrometer diamond suspension ("METADI DIAMOND SUSPENSION") on a polishing cloth ("TEXMET POLISHING CLOTH") until the majority of the 6 micrometer scratches were removed. The polished sample was translucent and lines were distinct when the sample was placed directly on top of them and at a distance. The sample appeared reddish in color in transmitted light and appeared bluish in color in reflected light. The Archimedes density and $T/T_L$ were measured as determined by the method described above. The sintered Example 5A sample had an Archimedes density of 6.07 $g/cm^3$, and a polished $T/T_L$ of 1.1 at a polished thickness of 0.63 mm.

The Example 5B and Example 5C samples 2.5 mm wafers were polished on one face using a 12 open face lapping machine ("LAPMASTER") for all but the final polishing step. The biaxial flexural strength was measured on the 2.5 mm samples after polishing using the test method above. The samples were all adhered to a sample plate and were then ground flat using 20 micrometer diamond tile ("3M TRIZACT DIAMOND TILE") at a speed of 30 rpm. The abrasive was then switched to 9 micrometer diamond tile ("3M TRIZACT DIAMOND TILE") and grinding continued at 30 rpm until the majority of the 20 micrometer scratches were removed. The abrasive was then switched to 3 micrometer diamond tile ("3M TRIZACT DIAMOND TILE") and grinding continued at 30 rpm until the majority of the 9 micrometer scratches were removed. The final polish was done using polishing equipment comprised of an electrically driven head ("VECTOR POWER HEAD") and a grinder-polisher ("BETA GRINDER-POLISHER") and 3 micrometer diamond suspension ("METADI DIAMOND SUSPENSION") on a polishing cloth ("TEXMET POLISHING CLOTH") until the majority of the scratches were removed. The average biaxial flexural strength was measured to be 1305 MPa using the test method described above.

EXAMPLE 6

A 39 gram sample of Sol C4 (prepared and diafiltered and concentrated as described above, 27.9 wt. % oxide and 3 wt. % acetic acid) and 184.9 grams of Sol T2 (prepared and diafiltered and concentrated as described above, 23.6 wt. % oxide and 2.3 wt. % acetic acid) was charged in to a 500 ml RB flask. Water (123.9 grams) was removed via rotary evaporation resulting in viscous somewhat dry material. Ethanol (30.3 grams), acrylic acid (5.8 grams), HEMA (3 grams) were added to the flask. The contents were stirred overnight resulting is a fluid translucent sol. 2,2'-azobis(2-methylbutyronitrile) ("VAZO 67") (0.3 gram) was added and stirred until dissolved. The contents of the flask were then purged with $N_2$ gas for 6 minutes). The sample (translucent and low viscosity) was charged to cylindrical containers (29 mm diameter). Each container was about 18 ml in volume and each was sealed on both ends (very little air gap was left between the top and liquid). The samples were allowed to stand for about 1 hour then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

Extraction Process

The wet $ZrO_2$-based gels of Example 6 were removed separately from the ethanol bath, weighed, placed individually inside small canvas pouches, and then stored briefly in another ethanol bath before being loaded into the 10-L extractor vessel. The wet weight of sample Example 6A was 19.5 grams. The wet weight of sample Example 6B was 19.3 grams. The wet weight of sample Example 6C was 19.5 grams. For extraction of all the gels of Example 6, about 850-875 ml of 200-proof ethanol was added to the 10-L extractor of a laboratory-scale supercritical fluid extractor. The canvas bags containing the wet zirconia-based gels were transferred from the ethanol bath into the 10-L extractor so that the wet gels were completely immersed in the liquid ethanol inside the jacketed extractor vessel, which was heated and maintained at 60° C. The Example 6 samples were subjected to the same extraction process as described above for the Example 5 samples. Afterwards, the dry aerogels were removed from their canvas pouches, weighed, and transferred into 237 ml glass jar packed with tissue paper for storage. The dry Example 6A aerogel was semi-translucent with a bluish tint and weighed 10.4 grams, corresponding to an overall weight loss during the supercritical extraction process of 46.7%. The dry Example 6B aerogel was semi-translucent with a bluish tint and weighed 10.2 grams corresponding to an overall weight loss during the supercritical extraction process of 47.2%. The dry Example 6C aerogel was semi-translucent with a bluish tint and weighed 10.3 grams corresponding to an overall weight loss during the supercritical extraction process of 47.2%.

Organic Burnout and Pre-sinter Process

The extracted Example 6 aerogel samples from above were removed from their closed container and the weight, diameter and height were measured prior to being set on a bed of zirconia beads in an unglazed porcelain crucible, covered with alumina fiberboard then fired in air according to the following schedule in a high temperature furnace ("THERMOLYNE TYPE 46200"): i—heat from 20° C. to 225° C. at 18° C./hr. rate; ii—hold at 225° C. for 24 hours; iii—heat from 225° C. to 400° C. at 6° C./hr. rate; iv—heat from 400° C. to 600° C. at 18° C./hr. rate; v—heat from 600° C. to 1090° C. at 120° C./hr. rate; and vi—cool down from 1090° C. to 20° C. at 600° C./hr. rate.

After firing, the samples were crack free. The samples of Example 6 were diced into about 1 mm or 2.5 mm thick wafers. The wafers were ion exchanged by first placing them in a 118 ml glass jar containing distilled water at a depth of about 2.5 cm and then vacuum infiltrating. The water was replaced with about a 2.5 cm depth of 1.0N $NH_4OH$ and the wafers were soaked overnight for 16 hours or longer. The $NH_4OH$ was then poured off and the jar was filled with distilled water. The wafers were soaked in the distilled water for 1 hour. The water was then replaced with fresh distilled water. This step was repeated until the pH of the soak water was equal to that of fresh distilled water. The wafers were then dried (90° C. to 125° C.) for a minimum of 1 hour. The aerogel of Example 6A had 12.2 volume % of oxides while the pre-sintered at 1090° C. aerogel of Example 6A had 51.4 volume % of oxides. The aerogel of Example 6B had 12.4 volume % of oxides while the pre-sintered (at 1090° C.) aerogel of Example 6B had 50.4 volume % of oxides. The aerogel of Example 6C had 12.35 volume % of oxides while the pre-sintered (at 1090° C.) aerogel of Example 6C had 49.8 volume % of oxides. The volume percent oxide values were calculated using the method described above.

Sintering Process

The wafers prepared above were set on a bed of zirconia beads in an alumina crucible, covered with alumina fiberboard then sintered in air according to the following schedule in a crucible furnace (Model 56724; "LINDBERG/BLUE M 1700° C."): i—heat from 20° C. to 1090° C. at 600° C./hr. rate; ii—heat from 1090° C. to 1250° C. at 120° C./hr. rate; iii—hold at 1250° C. for 2 hours; and iv—cool down from 1250° C. to 20° C. at 600° C./hr. rate.

Then the 1 mm thick Example 6A wafer was polished on both faces using Buehler polishing equipment comprised of an electrically driven head ("VECTOR POWER HEAD") and a grinder-polisher ("BETA GRINDER-POLISHER"). The sample was ground flat on both sides using 30 micrometer diamond lapping film ("3M DIAMOND LAPPING FILM 668X"). Then 9 micrometer diamond lapping film ("3M DIAMOND LAPPING FILM 668X") was used on both sides until the majority of the 30 micrometer scratches were removed. Next the sample was polished on both sides using 6 micrometer diamond suspension ("METADI DIAMOND SUSPENSION") on a polishing cloth ("TEXMET POLISHING CLOTH") until the majority of the 9 micrometer scratches were removed. Finally the sample was polished on both sides using 3 micrometer diamond suspension ("METADI DIAMOND SUSPENSION") on a polishing cloth ("TEXMET POLISHING CLOTH") until the majority of the 6 micrometer scratches were removed. The polished sample was translucent and lines were distinct when the sample was placed directly on top of them and at a distance. The sample appeared reddish in color in transmitted light and appeared bluish in color in reflected light. The Archimedes density and $T/T_L$ were measured as described above. The sintered Example 6A sample had an Archimedes density of 6.05 g/cm$^3$, and a polished $T/T_L$ of 1.15 at a polished thickness of 0.65 mm.

The Example 6B and Example 6C samples 2.5 mm wafers were polished on one face using a 12 open face lapping machine ("LAPMASTER") for all but the final polishing step. The biaxial flexural strength was measured on the 2.5 mm samples after polishing using the test method above. The samples were all adhered to a sample plate and were then ground flat using 20 micrometer diamond tile ("3M TRIZACT DIAMOND TILE") at a speed of 30 rpm. The abrasive was then switched to 9 micrometer diamond tile ("3M TRIZACT DIAMOND TILE") and grinding continued at 30 rpm until the majority of the 20 micrometer scratches were removed. The abrasive was then switched to 3 micrometer diamond tile ("3M TRIZACT DIAMOND TILE") and grinding continued at 30 rpm until the majority of the 9 micrometer scratches were removed. The final polish was done using Buehler polishing equipment comprised of an electrically driven head ("VECTOR POWER HEAD") and a grinder-polisher ("BETA GRINDER POLISHER") and 3 micrometer METADI diamond suspension ("DIAMOND SUSPENSION") on a polishing cloth ("TEXMET POLISHING CLOTH") until the majority of the scratches were removed. The average biaxial flexural strength was measured to be 1202 MPa using the test method described above.

EXAMPLE 7 and 8

For Example 7, a 23.3 gram sample of Sol C3 (prepared and diafiltered and concentrated as described above, 29.5 wt. % oxide and 3.1 wt. % acetic acid) and 32.4 grams of Sol T2 (prepared and diafiltered and concentrated as described above, 54.7 wt. % oxide and about 5.5 wt. % acetic acid) was charged in to a 500 ml RB flask. Water (7.9 grams) was removed via rotary evaporation resulting in a viscous somewhat dry material. Ethanol (18.2 grams), acrylic acid (2.9 grams) and HEMA (1.46 gram) were added to the flask. The contents were stirred overnight resulting in a fluid translucent sol. 2,2'-azobis(2-methylbutyronitrile) ("VAZO 67") (0.15 gram) was added and stirred until dissolved. The contents of the flask were then purged with $N_2$ gas for 3 minutes. The sample (translucent and low viscosity) was charged to cylindrical containers (29 mm diameter). Each container was about 18 ml in volume and each was sealed on both ends (very little air gap was left between the top and liquid). The samples were allowed to stand for about 1 hour then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

For Example 8, a 48.78 gram sample of Sol C4 (prepared and diafiltered and concentrated as described above, 27.9 wt. % oxide and 3 wt. % acetic acid) and 153.2 grams of Sol T2 (prepared and diafiltered and concentrated as described above, 26.6 wt. % oxide and 2.55 wt. % acetic acid) was charged in to a 500 ml RB flask. Water (102.7 grams) was removed via rotary evaporation resulting in a viscous somewhat dry material. Ethanol (30.3 grams), acrylic acid (5.8 grams) HEMA (2.9 grams) and DI water (0.7 gram) were added to the flask. The contents were stirred overnight resulting is a fluid translucent sol. 2,2'-azobis(2-methylbutyronitrile) ("VAZO 67") (0.3 gram) was added and stirred until dissolved. The contents of the flask were then purged with $N_2$ gas for 6 minutes. The sample (translucent and low viscosity) was charged to cylindrical containers (29 mm diameter). Each container was about 18 ml in volume and each was sealed on both ends (very little air gap was left between the top and liquid). The samples were allowed to stand for about 1 hour then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

Extraction Process

The wet $ZrO_2$-based gels of Examples 7 and 8 were removed separately from the ethanol bath, weighed, placed individually inside small canvas pouches, and then stored briefly in another ethanol bath before being loaded into the 10-L extractor vessel. The wet weight of sample Example 7A was 21.5 grams. The wet weight of sample Example 7B was 20.5 grams. The wet weight of sample Example 7C was 19.9 gram. The wet weight of sample Example 8 was 20.2 grams. For extraction of all the gels of Examples 7 and 8, about 800 ml of 200-proof ethanol was added to the 10-L extractor of a laboratory-scale supercritical fluid extractor. The canvas bags containing the wet zirconia-based gels were transferred from the ethanol bath into the 10-L extractor so that the wet gels were completely immersed in the liquid ethanol inside the jacketed extractor vessel, which was heated and maintained at 60° C. The Example 7A, 7B, 7C, and Example 8 samples were subjected to the same extraction process as described above for Examples 1 and 2 samples. Afterwards, the dry aerogels were removed from their canvas pouches, weighed, and transferred into individual 237 ml glass jars packed with tissue paper for storage. The dry Example 7A aerogel was semi-translucent with a bluish tint and weighed 11.5 grams, corresponding to an overall weight loss during the supercritical extraction process of 46.5%. The dry Example 7B aerogel was semi-translucent with a bluish tint and weighed 11.1 grams, corresponding to an overall weight loss during the supercritical extraction process of 45.9%. The dry Example 7C aerogel was semi-translucent with a bluish tint and weighed 10.7 grams, corresponding to an overall weight loss during the supercritical extraction process of 46.2%. The dry Example 8 aerogel was semi-translucent with a bluish tint and weighed 11.1 grams, corresponding to an overall weight loss during the supercritical extraction process of 45%.

Organic Burnout and Pre-sinter Process

The extracted Example 7A and 7B aerogel samples prepared above were removed from their closed containers and dried for 1 hour in open air prior to being set on a bed of zirconia beads in an unglazed porcelain crucible, covered with alumina fiberboard then fired in air according to the following schedule in a high temperature furnace ("THERMOLYNE TYPE 46200"): i—heat from 20° C. to 225° C. at 18° C./hr. rate; ii—hold at 225° C. for 24 hours; iii—heat from 225° C. to 400° C. at 6° C./hr. rate; iv—heat from 400° C. to 600° C. at 18° C./hr. rate; v—heat from 600° C. to 1090° C. at 120° C./hr. rate; and vi—cool down from 1090° C. to 20° C. at 600° C./hr. rate.

After firing the samples were crack free. The cylinders were diced into about 1 mm or 2.5 mm thick wafers. The samples of Examples 7A and 7B wafers were ion exchanged by first placing them in a 118 ml glass jar containing distilled water at a depth of about 2.5 cm and then vacuum infiltrating. The water was replaced with about a 2.5 cm depth of 1.0N $NH_4OH$ and the wafers were soaked overnight for 16 hours or longer. The $NH_4OH$ was then poured off and the jar was filled with distilled water. The wafers were soaked in the distilled water for 1 hour. The water was then replaced with fresh distilled water. This step was repeated until the pH of the soak water was equal to that of fresh distilled water. The wafers were then dried at 90-125° C. for a minimum of 1 hour.

The extracted aerogel sample of Example 7C prepared above was analyzed to determine the BET surface area, pore size and porosity. The aerogel of Example 7C had a 222 $m^2/g$ of surface area MBET, 0.826 $cm^3/g$ of total pore volume and 149 Angstrom of average pore diameter.

Example 8 samples had the same organic burnout and pre-sinter conditions as Examples 7A and 7B except it was not dried in open air prior to organic burnout and pre-sinter. Also, half of the Example 8 wafers were ion exchanged as described for Examples 7A and 7B and the other half were not.

The pre-sintered at 1090° C. aerogels of Examples 7A, 7B and Example 8A (ion-exchanged) and Example 8B (not ion-exchanged) had 45.2, 47, 44.6, and 44.5 volume % of oxides, respectively, as determined by dividing the geometric density of the pre-sintered wafer by the Archimedes density of the sintered wafer and then multiplying by 100.

Sintering Process

Wafers were set on a bed of zirconia beads in an alumina crucible, covered with alumina fiberboard then sintered in air according to the following schedule in a crucible furnace (Model 56724; "LINDBERG/BLUE M 1700° C."): i—heat from 20° C. to 1090° C. at 600° C./hr. rate; ii—heat from 1090° C. to 1250° C. at 120° C./hr. rate; iii—hold at 1250° C. for 2 hours; and iv—cool down from 1250° C. to 20° C. at 600° C./hr. rate.

An as fired 7A wafer was submitted for XRD. The 1 mm wafers were polished on both faces and the 2.5 mm wafers were polished on one face using a 12 open face lapping machine ("LAPMASTER") for all but the final polishing step. The biaxial flexural strength was measured on the 2.5 mm samples after polishing using the test method above. The samples were all adhered to a sample plate and were then ground flat using a 20 micrometer diamond tile ("3M TRIZACT DIAMOND TILE") at a speed of 30 rpm. The abrasive was then switched to a 9 micrometer diamond tile ("3M TRIZACT DIAMOND TILE") and grinding continued at 30 rpm until the majority of the 20 micrometer scratches were removed. The abrasive was then switched to a 3 micrometer diamond tile ("3M TRIZACT DIAMOND TILE") and grinding continued at 30 rpm until the majority of the 9 micrometer scratches were removed. The final polish was done using polishing equipment comprised of an electrically driven head ("VECTOR POWER HEAD") and a grinder-polisher ("BETA GRINDER-POLISHER") and 3 micrometer diamond suspension ("METADI DIAMOND SUSPENSION") on a polishing cloth ("TEXMET POLISHING CLOTH") until the majority of the scratches were removed. The samples polished on both faces were translucent and lines were distinct when the samples were placed directly on top of them and at a distance. The samples appeared reddish in color in transmitted light and appeared bluish in color in reflected light. The Example 8B sample that was not ion exchanged exhibited a slight tan color that was not seen in the sample that was ion exchanged. The Archimedes density and $T/T_L$ were measured as described above. After strength testing a piece of sintered Example 7B was set on a bed of zirconia beads in an alumina crucible and thermally etched in air in a rapid temperature furnace (CM Furnaces Inc.) as follows: i—heat from 20° C. to 1200° C. at 450° C./hr. rate; ii—hold at 1200° C. for 0.5 hour; and iii—cool from 1200° C. to 20° C. at 600° C./hr. rate.

FESEM was done on the thermally etched sample as described in the test method described above. The grain size was determined using the line intercept method described in the test method above.

The properties of the sintered wafers of Examples 7A, 7B, Example 8A (ion-exchanged) and Example 8B (not ion-exchanged) are given in Table 4, below.

TABLE 4

| Example | Archimedes Density, $g/cm^3$ | Polished Thickness, mm | Polished $T/T_L$ | Grain Size, nm | Strength, MPa | Phase Composition (XRD) |
| --- | --- | --- | --- | --- | --- | --- |
| 7A | 6.03 | 0.31 | 1.46 | | | [ZrO2(T) major a = 3.628 c = 5.179] |
| 7B | 6.07 | 1.71 | | 156 | 1323 | |
| 8A | 6.05 | 0.55 | 1.36 | | | |
| 8B | 6.05 | 0.49 | 1.35 | | | |

EXAMPLE 9

For Example 9, a 68.25 gram sample of Sol C4 (prepared, diafiltered and concentrated as described above, 27.9 wt. % oxide and 3 wt. % acetic acid) and 150.4 gram of Sol T2 (prepared and diafiltered and concentrated as described above, 23.55 wt. % oxide and 2.3 wt. % acetic acid) was charged in to a 500 ml RB flask. Water (118.6 grams) was removed via rotary evaporation resulting in a viscous somewhat dry material. Ethanol (30.3 grams), acrylic acid (5.8 grams) HEMA (2.9 grams) and DI water (0.7 gram) were added to the flask. The contents were stirred overnight resulting in a fluid translucent sol. 2,2'-azobis(2-methylbutyronitrile) ("VAZO 67") (0.3 gram) was added and stirred until dissolved. The contents of the flask were then purged with $N_2$ gas for 6 minutes. The sample (translucent and low viscosity) was charged to cylindrical containers (29 mm diameter). Each container was about 18 ml in volume and each was sealed on both ends (very little air gap was left between the top and liquid). The samples were allowed to stand for about 1 hour then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

Extraction Process

The wet $ZrO_2$ based gels of Example 9 were removed separately from the ethanol bath, weighed, placed individually inside small canvas pouches, and then stored briefly in another ethanol bath before being loaded into the 10-L extractor vessel. The wet weight of Example 9A was 20.4 grams. The wet weight of Example 9B was 21.3 grams. The wet weight of Example 9C was 21.1 grams. For extraction on all the gels of Example 9, about 850-875 ml of 200-proof ethanol was added to the 10-L extractor of a laboratory-scale supercritical fluid extractor unit. The canvas bags containing the wet zirconia-based gels were transferred from the ethanol bath into the 10-L extractor so that the wet gels were completely immersed in the liquid ethanol inside the jacketed extractor vessel, which was heated and maintained at 60° C. The Example 9 samples were subjected to the same extraction process as described above for the Example 5 sample. Afterwards, the dry aerogels were removed from their canvas pouches, weighed, and transferred into a 237 ml glass jar packed with tissue paper for storage. The dry Example 9A aerogel was semi-translucent with a bluish tint and weighed 10.9 grams, corresponding to an overall weight loss during the supercritical extraction process of 46.6%. The dry Example 9B aerogel was semi-translucent with a bluish tint and weighed 11.3 grams corresponding to an overall weight loss during the supercritical extraction process of 47%. The dry Example 9C aerogel was semi-translucent with a bluish tint and weighed 11.2 grams corresponding to an overall weight loss during the supercritical extraction process of 46.9%.

Organic Burnout and Pre-Sinter Process

The extracted Example 9 aerogel samples from above were removed from their closed containers and the weight, diameter and height were measured prior to being set on a bed of zirconia beads in an unglazed porcelain crucible, covered with alumina fiberboard then fired in air according to the following schedule in a high temperature furnace ("THERMOLYNE TYPE 46200"): i—heat from 20° C. to 225° C. at 18° C./hr. rate; ii—hold at 225° C. for 24 hours; iii—heat from 225° C. to 400° C. at 6° C./hr. rate; iv—heat from 400° C. to 600° C. at 18° C./hr. rate; v—heat from 600° C. to 1090° C. at 120° C./hr. rate; and vi—cool down from 1090° C. to 20° C. at 600° C./hr. rate.

After firing the samples were crack free. The samples of Example 9 were diced into about 1 mm or 2.5 mm thick wafers. The wafers were ion exchanged by first placing them in a 118 ml glass jar containing distilled water at a depth of about 2.5 cm and then vacuum infiltrating. The water was replaced with about a 2.5 cm depth of 1.0N $NH_4OH$ and the wafers were soaked overnight for 16 hours or longer. The $NH_4OH$ was then poured off and the jar was filled with distilled water. The wafers were soaked in the distilled water for 1 hour. The water was then replaced with fresh distilled water. This step was repeated until the pH of the soak water was equal to that of fresh distilled water. The wafers were then dried (at 90° C. to 125° C.) for a minimum of 1 hour. The aerogel of Example 9A had 12 volume % of oxides while the pre-sintered (at 1090° C.) aerogel of Example 9A had 49.3 volume % of oxides. The aerogel of Example 9B had 12.1 volume % of oxides while the pre-sintered (at 1090° C.) aerogel of Example 9B had 47.9 volume % of oxides. The aerogel of Example 9C had 12 volume % of oxides while the pre-sintered (at 1090° C.) aerogel of Example 9C had 47.8 volume % of oxides. The volume percent oxide values were calculated using the method described above.

Sintering Process

The wafers prepared as described above were set on a bed of zirconia beads in an alumina crucible, covered with alumina fiberboard then sintered in air according to the following schedule in a crucible furnace (Model 56724; "LINDBERG/BLUE M 1700° C."): i—heat from 20° C. to 1090° C. at 600° C./hr. rate; ii—heat from 1090° C. to 1250° C. at 120° C./hr. rate; iii—hold at 1250° C. for 2 hours; and iv—cool down from 1250° C. to 20° C. at 600° C./hr. rate.

The 1 mm thick Example 9A wafer was polished on both faces using polishing equipment comprised of an electrically driven head ("VECTOR POWER HEAD") and a grinder-polisher ("BETA GRINDER-POLISHER"). The sample was ground flat on both sides using 30 micrometer diamond lapping film ("3M DIAMOND LAPPING FILM 668X"). Then 9 micrometer diamond lapping film ("3M DIAMOND LAPPING FILM 668X") was used on both sides until the majority of the 30 micrometer scratches were removed. Next the sample was polished on both sides using 6 micrometer diamond suspension ("METADI DIAMOND SUSPENSION") on a polishing cloth ("TEXMET POLISHING CLOTH") until the majority of the 9 micrometer scratches were removed. Finally the sample was polished on both sides using 3 micrometer diamond suspension ("METADI DIAMOND SUSPENSION") on a polishing cloth ("TEXMET POLISHING CLOTH") until the majority of the 6 micrometer scratches were removed. The polished sample was translucent and lines were distinct when the sample was placed directly on top of them and at a distance. The sample appeared reddish in color in transmitted light and appeared bluish in color in reflected light. The Archimedes density and $T/T_L$ were measured as described above. The sintered Example 9A samples had an Archimedes density of 6.03 g/cm³, a polished $T/T_L$ of 1.5 at a polished thickness of 0.66 mm.

The Example 9B and Example 9C samples 2.5 mm wafers were polished on one face using a 12 open face lapping machine "LAPMASTER") for all but the final polishing step. The biaxial flexural strength was measured on the 2.5 mm samples after polishing using the test method above. The samples were all adhered to a sample plate and were then ground flat using 20 micrometer diamond tile ("3M TRIZACT DIAMOND TILE") at a speed of 30 rpm. The abrasive was then switched to 9 micrometer diamond tile ("3M TRIZACT DIAMOND TILE") and grinding continued at 30 rpm until the majority of the 20 micrometer scratches were removed. The abrasive was then switched to 3 micrometer diamond tile ("3M TRIZACT DIAMOND TILE") and grinding continued at 30 rpm until the majority of the 9 micrometer scratches were removed. The final polish was done using Buehler polishing equipment comprised of an electrically driven head ("VECTOR POWER HEAD") and a grinder-polisher ("BETA GRINDER POLISHER") and 3 micrometer METADI diamond suspension ("DIAMOND SUSPENSION") on a polishing cloth ("TEXMET POLISHING CLOTH") until the majority of the scratches were removed. The average biaxial flexural strength was measured to be 757 MPa using the test method described above.

EXAMPLE 10

For Examples 10A and 10B, a 46.3 gram sample of Sol C3 (prepared and diafiltered and concentrated as described above, 29.5 wt. % oxide and 3.1 wt. % acetic acid) and 24.9 grams of Sol T2 (prepared and diafiltered and concentrated as described above, 54.7 wt. % oxide and about 5.5 wt. % acetic acid) was charged in to a 500 ml RB flask. Water (26.8 grams) was removed via rotary evaporation resulting in a viscous somewhat dry material. Ethanol (20.7 grams), acrylic acid (2.9 grams) HEMA (1.47 gram) were added to the flask. The contents were stirred overnight resulting in a fluid translucent sol. 2,2'-azobis(2-methylbutyronitrile) ("VAZO 67") (0.15 gram) was added and stirred until dissolved. The contents of the flask were then purged with $N_2$ gas for 3 minutes. The sample (translucent and low viscosity) was charged to cylindrical containers (29 mm diameter). Each container was about 18 ml in volume and each was sealed on both ends (very little air gap was left between the top and liquid). The samples were allowed to stand for about 1 hr then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

Extraction Process

The wet $ZrO_2$-based gels of Example 10A and 10B were removed separately from the ethanol bath, weighed, placed individually inside small canvas pouches, and then stored briefly in another ethanol bath before being loaded into the 10-L extractor vessel. The wet weight of Example 10A was 19.4 grams. The wet weight of sample Example 10B was 21.6 grams. For the extraction of both Examples 10A and 10B, about 800 ml of 200-proof ethanol was added to the 10-L extractor of a laboratory-scale supercritical fluid extractor unit. The canvas bags containing the wet zirconia-based gels were transferred from the ethanol bath into the 10-L extractor so that the wet gels were completely immersed in the liquid ethanol inside the jacketed extractor vessel, which was heated and maintained at 60° C. The Example 10A and 10B samples were subjected to the same extraction process as described above for Examples 1 and 2 samples. Afterwards, the dry aerogels were removed from their canvas pouches, weighed, and transferred into individual 237 ml glass jars packed with tissue paper for storage. The dry Example 10A aerogel was semi-translucent with a bluish tint and weighed 10.3 grams, corresponding to an overall weight loss during the supercritical extraction process of 46.9%. The dry Example 10B aerogel was semi-translucent with a bluish tint and weighed 11.5 grams, corresponding to an overall weight loss during the supercritical extraction process of 46.8%.

Organic Burnout and Pre-sinter Process

The extracted Example 10A and 10B aerogel samples from above were removed from their closed containers and dried for 1 hour in open air prior to being set on a bed of zirconia beads in an unglazed porcelain crucible, covered with alumina fiberboard then fired in air according to the following schedule in a high temperature furnace ("THERMOLYNE TYPE 46200"): i—heat from 20° C. to 225° C. at 18° C./hr. rate; ii—hold at 225° C. for 24 hours; iii—heat from 225° C. to 400° C. at 6° C./hr. rate; iv—heat from 400° C. to 600° C. at 18° C./hr. rate; v—heat from 600° C. to 1090° C. at 120° C./hr. rate; and vi—cool down from 1090° C. to 20° C. at 600° C./hr. rate.

After firing the samples were crack free. The cylinders were diced into about 1 mm or 2.5 mm thick wafers. The samples of Example 10A and 10B wafers were ion exchanged by first placing them in a 118 ml glass jar containing distilled water at a depth of about 2.5 cm and then vacuum infiltrating. The water was replaced with about a 2.5 cm depth of 1.0N $NH_4OH$ and the wafers were soaked overnight for 16 hours or longer. The $NH_4OH$ was then poured off and the jar was filled with distilled water. The wafers were soaked in the distilled water for 1 hour. The water was then replaced with fresh distilled water. This step was repeated until the pH of the soak water was equal to that of fresh distilled water. The wafers were then dried at 90-125° C. for a minimum of 1 hour. The pre-sintered at 1090° C. aerogels of Example 10A and 10B had 45.6 and 46.2 volume % of oxides, respectively, as determined by dividing the geometric density of the pre-sintered wafer by the Archimedes density of the sintered wafer and then multiplying by 100.

Sintering Process

Wafers were set on a bed of zirconia beads in an alumina crucible, covered with alumina fiberboard then sintered in air according to the following schedule in a crucible furnace (Model 56724; "LINDBERG/BLUE M 1700° C."): i—heat from 20° C. to 1090° C. at 600° C./hr. rate; ii—heat from 1090° C. to 1250° C. at 120° C./hr. rate; iii—hold at 1250° C. for 2 hours; and iv—cool down from 1250° C. to 20° C. at 600° C./hr. rate.

A sample of Example 10A as-fired wafer was analyzed using XRD. The 1 mm wafers were polished on both faces and the 2.5 mm wafers were polished on one face using a 12 open face lapping machine ("LAPMASTER") for all but the final polishing step. The biaxial flexural strength was measured on the 2.5 mm samples after polishing using the test method above. The samples were all adhered to a sample plate and were then ground flat using 20 micrometer diamond tile ("3M TRIZACT DIAMOND TILE") at a speed of 30 rpm. The abrasive was then switched to 9 micrometer diamond tile ("3M TRIZACT DIAMOND TILE") and grinding continued at 30 rpm until the majority of the 20 micrometer scratches were removed. The abrasive was then switched to 3 micrometer diamond tile ("3M TRIZACT DIAMOND TILE") and grinding continued at 30 rpm until the majority of the 9 micrometer scratches were removed. The final polish was done using Buehler polishing equipment comprised of an electrically driven head ("VECTOR POWER HEAD") and a grinder-polisher ("BETA GRINDER-POLISHER") and 3 micrometer diamond suspension ("METADI DIAMOND SUSPENSION") on a polishing cloth ("TEXMET POLISHING CLOTH") until the majority of the scratches were removed. The samples polished on both faces were translucent and lines were distinct when the samples were placed directly on top of them and at a distance. The samples appeared reddish in color in transmitted light and appeared bluish in color in reflected light. The Archimedes density and $T/T_L$ were measured as described above. After strength testing a piece of aerogel of Example 10B was set on a bed of zirconia beads in an alumina crucible and thermally etched in air in a rapid temperature furnace (CM Furnaces Inc.) as follows: i—heat from 20° C. to 1200° C. at 450° C./hr. rate; ii—hold at 1200° C. for 0.5 hour; and iii-cool from 1200° C. to 20° C. at 600° C./hr. rate.

FESEM was done on the thermally etched sample as described in the test method described above. The grain size was determined using the line intercept method described in the test methods above.

The properties of the sintered wafers are given in Table 5, below.

TABLE 5

| Example | Archimedes Density, g/cm³ | Polished Thickness, mm | Polished T/T$_L$ | Grain Size, nm | Strength, MPa | Composition (XRD) |
|---|---|---|---|---|---|---|
| 10A | 6.02 | 0.52 | 1.77 | | | [ZrO2(T) major a = 3.637 c = 5.177] |
| 10B | 6.05 | 1.71 | | 183 | 494 | |

EXAMPLE 11

For Examples 11A and 11B, a 30.2 gram sample of Sol C4 (prepared and diafiltered and concentrated as described above, 27.9 wt. % oxide and 3.05 wt. % acetic acid) and 52.55 grams of Sol B1 (prepared and diafiltered and concentrated as described above, 35.8 wt. % oxide and 3.2 wt. % acetic acid) was charged in to a 500 ml RB flask. Water (39.3 grams) was removed via rotary evaporation resulting in a viscous somewhat dry material. Ethanol (15.15 grams), acrylic acid (1.5 gram), HEMA (1.5 gram) and DI water (1.2 gram) were added to the flask. The contents were stirred overnight resulting in a fluid translucent sol. 2,2'-azobis(2-methylbutyronitrile) ("VAZO 67") (0.15 gram) was added and stirred until dissolved. The contents of the flask were then purged with $N_2$ gas for 3 minutes. The sample (translucent and low viscosity) was charged to cylindrical containers (29 mm diameter). Each container was about 18 ml in volume and each was sealed on both ends (very little air gap was left between the top and liquid). The samples were allowed to stand for about 1 hour then placed in an oven to cure (50° C., 4 hours). This resulted in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

Extraction Process

The wet $ZrO_2$-based gels of Examples 11A and 11B were removed separately from the ethanol bath, weighed, placed individually inside small canvas pouches, and then stored briefly in another ethanol bath before being loaded into the 10-L extractor vessel. The wet weight of Example 11A was 18.7 gram. The wet weight of Example 11B was 19.9 grams. About 850 ml of 200-proof ethanol was added to the 10-L extractor of a laboratory-scale supercritical fluid extractor unit. The canvas bags containing the wet zirconia-based gels were transferred from the ethanol bath into the 10-L extractor so that the wet gels were completely immersed in the liquid ethanol inside the jacketed extractor vessel, which was heated and maintained at 60° C. The Example 11A and 11B samples were subjected to the same extraction process as described above for Examples 1 and 2 samples. Afterwards, the dry aerogels were removed from their canvas pouches, weighed, and transferred into individual 237 ml glass jars packed with tissue paper for storage. The dry Example 11A aerogel was semi-translucent with a bluish tint and weighed 10.4 grams, corresponding to an overall weight loss during the supercritical extraction process of 44.4%. The dry Example 11B aerogel was semi-translucent with a bluish tint and weighed 11.2 grams, corresponding to an overall weight loss during the supercritical extraction process of 43.7%.

Organic Burnout and Pre-Sinter Process

The extracted Example 11A and 11B aerogel samples from above were removed from their closed containers and immediately set on a bed of zirconia beads in an unglazed porcelain crucible, covered with alumina fiberboard then fired in air according to the following schedule in a high temperature furnace ("THERMOLYNE TYPE 46200"): i—heat from 20° C. to 225° C. at 18° C./hr. rate; ii-hold at 225° C. for 24 hours; iii—heat from 225° C. to 400° C. at 6° C./hr. rate; iv—heat from 400° C. to 600° C. at 18° C./hr. rate; v—heat from 600° C. to 1090° C. at 120° C./hr. rate; and vi—cool down from 1090° C. to 20° C. at 600° C./hr. rate.

After firing, the samples were crack free. The Example 11A cylinder was diced into about 1 mm or 2 mm thick wafers. The Example 11A wafers were ion exchanged by first placing them in a 118 ml glass jar containing distilled water at a depth of about 2.5 cm and then vacuum infiltrating. The water was replaced with about a 2.5 cm depth of 1.0N $NH_4OH$ and the wafers were soaked overnight for 16 hours or longer. The $NH_4OH$ was then poured off and the jar was filled with distilled water. The wafers were soaked in the distilled water for 1 hour. The water was then replaced with fresh distilled water. This step was repeated until the pH of the soak water was equal to that of fresh distilled water. The wafers were then dried at 90-125° C. for a minimum of 1 hour. The pre-sintered at 1090° C. aerogel of Example 11A had 47.8 volume % of oxides, as determined by dividing the geometric density of the pre-sintered wafer by the Archimedes density of the sintered wafer and then multiplying by 100.

Sintering Process 2 mm wafers of Example 11A were set on a bed of zirconia beads in an alumina crucible, covered with alumina fiberboard then sintered in air according to the following schedule in a crucible furnace (Model 56724; "LINDBERG/BLUE M 1700° C."): i—heat from 20° C. to 1090° C. at 600° C./hr. rate; ii—heat from 1090° C. to 1250° C. at 120° C./hr. rate; iii—hold at 1250° C. for 2 hours; and iv—cool down from 1250° C. to 20° C. at 600° C./hr. rate.

A wafer was polished on both faces using Buehler polishing equipment comprised of an electrically driven head ("VECTOR POWER HEAD") and a grinder-polisher ("BETA GRINDER-POLISHER"). The sample was ground flat on both sides using 30 micrometer diamond lapping film ("3M DIAMOND LAPPING FILM 668X"). Then 9 micrometer diamond lapping film ("3M DIAMOND LAPPING FILM 668X") was used on both sides until the majority of the 30 micrometer scratches were removed. Next the sample was polished on both sides using 6 micrometer diamond suspension ("METADI DIAMOND SUSPENSION") on a polishing cloth ("TEXMET POLISHING CLOTH") until the majority of the 9 micrometer scratches were removed. Finally the sample was polished on both sides using 3 micrometer diamond suspension ("METADI DIAMOND SUSPENSION") on a polishing cloth ("TEXMET POLISHING CLOTH") until the majority of the 6 micrometer scratches were removed. The sample was translucent and lines were distinct when the sample was placed directly on top of them and at a distance. The sample appeared reddish in color in transmitted light and appeared bluish in color in reflected light. The Archimedes density and $T/T_L$ were measured as described above. The sample was set on a bed of zirconia beads in an alumina crucible and thermally etched in air in a rapid temperature furnace (CM Furnaces Inc.) as follows: i—heat from 20° C. to 1200° C. at 450° C./hr. rate; ii—hold at 1200° C. for 0.5 hour; and iii—cool from 1200° C. to 20° C. at 600° C./hr. rate.

FESEM was done on the thermally etched sample as described in the test method described above. The grain size was determined using the line intercept method described in the test method above.

The sintered Example 11A sample had an Archimedes density of 6.02 g/cm³, a polished $T/T_L$ of 2 at a polished thickness of 1.1 mm, and an average grain size of 202 nm.

EXAMPLE 12 and 13

For Examples 12A and 12B, a 69.40 gram sample of Sol C3 (prepared and diafiltered and concentrated as described above, 29.5 wt. % oxide and 3.1 wt. % acetic acid) and 12.4 grams of Sol T2 (prepared and diafiltered and concentrated as described above, 54.7 wt. % oxide and about 5.5 wt. % acetic acid) was charged in to a 500 ml RB flask. Water (32.7 grams) was removed via rotary evaporation resulting in a viscous somewhat dry material. Ethanol (16.1 grams), acrylic acid (2.9 grams), HEMA (1.47 gram) were added to the flask. The contents were stirred overnight resulting in a fluid translucent sol. 2,2'-azobis(2-methylbutyronitrile) ("VAZO 67") (0.15 gram) was added and stirred until dissolved. The contents of the flask were then purged with $N_2$ gas for 3 minutes. The sample (translucent and low viscosity) was charged to cylindrical containers (29 mm diameter). Each container was about 18 ml in volume and each was sealed on both ends (very little air gap was left between the top and liquid). The samples were allowed to stand for about 1 hour then placed in an oven to cure (50° C., 4 hours). This results in clear translucent blue gels. The gels were removed from the container and placed in a 473 ml wide mouth jar. The jar was filled with ethanol (denatured). The samples were soaked for 24 hr then the ethanol was replaced with fresh ethanol. The samples were soaked for 24 hr then the ethanol was replaced with a third batch of fresh ethanol. The samples were allowed to soak until the supercritical extraction was done. The above manipulations were done minimizing the amount of time the gels were exposed to the air.

For Example 13, a 73.1 gram sample of Sol C4 (prepared and diafiltered and concentrated as described above, 27.9 wt. % oxide and 3 wt. % acetic acid) and 25.5 grams of Sol T2 (prepared and diafiltered and concentrated as described above, 26.6 wt. % oxide and 2.9 wt. % acetic acid) was charged in to a 500 ml RB flask. Water (49.2 grams) was removed via rotary evaporation resulting in a viscous somewhat dry material. Ethanol (15.15 grams), acrylic acid (2.9 grams), HEMA (1.5 gram) and DI water (0.55 gram) were added to the flask. The contents were stirred overnight resulting is a fluid translucent sol. 2,2'-azobis(2-methylbutyronitrile) ("VAZO 67") (0.15 gram) was added and stirred until dissolved. The contents of the flask were then purged with $N_2$ gas for 3 minutes. The sample (translucent and low viscosity) was charged to cylindrical containers (29 mm diameter). Each container was about 18 ml in volume and each was sealed on both ends (very little air gap was left between the top and liquid). The samples were allowed to stand for about 1 hour then placed in an oven to cure (50° C., 4 hours). This resulted in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hour then the ethanol was replaced with a third batch of fresh ethanol. The sample was allowed to soak until the supercritical extraction was done. The above manipulations were done minimizing the amount of time the gel was exposed to the air.

Extraction Process

The wet $ZrO_2$-based gels of Examples 12A, 12B and 13 were removed separately from the ethanol bath, weighed, placed individually inside small canvas pouches, and then stored briefly in another ethanol bath before being loaded into the 10-L extractor vessel. The wet weight of sample of Example 12A was 21.7 grams. The wet weight of sample of Example 12B was 16.6 grams. The wet weight of sample of Example 13 was 20.9 grams. For extraction of both Examples 12A, 12B and 13, about 800 ml of 200-proof ethanol was added to the 10-L extractor of a laboratory-scale supercritical fluid extractor. The canvas bags containing the wet zirconia-based gels were transferred from the ethanol bath into the 10-L extractor so that the wet gels were completely immersed in the liquid ethanol inside the jacketed extractor vessel, which was heated and maintained at 60° C. The Example 12A, 12B and 13 samples were subjected to the same extraction process as described above for Examples 1 and 2 samples. Afterwards, the dry aerogels were removed from their canvas pouches, weighed, and transferred into individual 237 ml glass jars packed with tissue paper for storage. The dry Example 12A aerogel was semi-translucent with a bluish tint and weighed 11.9 grams, corresponding to an overall weight loss during the supercritical extraction process of 45.2%. The dry Example 12B aerogel was semi-translucent with a bluish tint and weighed 9.2 grams, corresponding to an overall weight loss during the supercritical extraction process of 44.6%. The dry Example 13 aerogel was semi-translucent with a bluish tint and weighed 11.5 grams, corresponding to an overall weight loss during the supercritical extraction process of 45%.

Organic Burnout and Pre-Sinter Process

The extracted Example 12A, 12B, and 13 aerogel samples from above were removed from their closed containers and dried for 1 hour in open air prior to being set on a bed of zirconia beads in an unglazed porcelain crucible, covered with alumina fiberboard then fired in air according to the following schedule in a high temperature furnace ("THERMOLYNE TYPE 46200"): i—heat from 20° C. to 225° C. at 18° C./hr. rate; ii—hold at 225° C. for 24 hours; iii—heat from 225° C. to 400° C. at 6° C./hr. rate; iv—heat from 400° C. to 600° C. at 18° C./hr. rate; v—heat from 600° C. to 1090° C. at 120° C./hr. rate; and vi—cool down from 1090° C. to 20° C. at 600° C./hr. rate.

After firing the samples of Examples 12B and 13 were crack free. The samples of Example 12A, 12B and 13 were diced into about 1 mm or 2.5 mm thick wafers. The wafers were ion exchanged by first placing them in a 118 ml glass jar containing distilled water at a depth of about 2.5 cm and then vacuum infiltrating. The water was replaced with about a 2.5 cm depth of 1.0N $NH_4OH$ and the wafers were soaked overnight for 16 hours or longer. The $NH_4OH$ was then poured off and the jar was filled with distilled water. The wafers were soaked in the distilled water for 1 hour. The water was then replaced with fresh distilled water. This step was repeated until the pH of the soak water was equal to that of fresh distilled water. The wafers were then dried at 90-125° C. for a minimum of 1 hour. The pre-sintered at 1090° C. aerogels of Example 12B and 13 had 48.1 and 46.4 volume % of oxides, respectively as determined by dividing the geometric density of the pre-sintered wafer by the Archimedes density of the sintered wafer and then multiplying by 100.

Sintering Process

Wafers were set on a bed of zirconia beads in an alumina crucible, covered with alumina fiberboard then sintered in air according to the following schedule in a crucible furnace (Model 56724; "LINDBERG/BLUE M 1700° C."): i—heat from 20° C. to 1090° C. at 600° C./hr. rate; ii—heat from 1090° C. to 1250° C. at 120° C./hr. rate; iii—hold at 1250° C. for 2 hours; and iv—cool down from 1250° C. to 20° C. at 600° C./hr. rate.

One of the sintered wafers of Example 12A was analyzed using XRD. The Example 12B and 13, 1 mm wafers were polished on both faces and the 2.5 mm wafers were polished on one face using a 12 open face lapping machine ("LAPMASTER") for all but the final polishing step. The biaxial flexural strength was measured on the 2.5 mm samples after polishing using the test method above. The samples were all adhered to a sample plate and were then ground flat using 20 micrometer diamond tile ("3M TRIZACT DIAMOND TILE") at a speed of 30 rpm. The abrasive was then switched to 9 micrometer diamond tile ("3M TRIZACT DIAMOND TILE") and grinding continued at 30 rpm until the majority of the 20 micrometer scratches were removed. The abrasive was then switched to 3 micrometer diamond tile ("3M TRIZACT DIAMOND TILE") and grinding continued at 30 rpm until the majority of the 9 micrometer scratches were removed. The final polish was done using Buehler polishing equipment comprised of an electrically driven head ("VECTOR POWER HEAD") and a grinder-polisher ("BETA GRINDER-POLISHER") and 3 micrometer diamond suspension ("METADI DIAMOND SUSPENSION") on a polishing cloth ("TEXMET POLISHING CLOTH") until the majority of the scratches were removed. The samples polished on both faces were translucent and lines were distinct when the samples were placed directly on top of them and at a distance. The samples appeared slightly reddish in color in transmitted light and appeared slightly bluish in color in reflected light. The Archimedes density and $T/T_L$ were measured as described above. After strength testing a piece of aerogel of Example 13 was set on a bed of zirconia beads in an alumina crucible and thermally etched in air in a rapid temperature furnace (CM Furnaces Inc.,) as follows: i—heat from 20° C. to 1200° C. at 450° C./hr. rate; ii—hold at 1200° C. for 0.5 hour; and iii—cool from 1200° C. to 20° C. at 600° C./hr. rate.

FESEM was done on the thermally etched sample of Example 13 as described in the test method described above. The grain size was determined using the line intercept method described in the test method above.

The properties of the sintered wafers are given in Table 6, below.

TABLE 6

| Example | Archimedes Density, g/cm³ | Polished Thickness mm | Polished T/T$_L$ | Grain Size, nm | Strength, MPa | Composition (XRD) |
|---|---|---|---|---|---|---|
| 12A | 6.00 | | | | | [ZrO2(C) major a = 5.146] |
| 12B | 6.00 | 0.4 | 1.89 | | | |
| 13 | 6.00 | 1.5 | | 236 | 877 | |

EXAMPLE 14

For Example 14A and 14B 63.85 gram sample of Sol C4 (prepared and diafiltered and concentrated as described above, 27.9 wt. % oxide and 3 wt. % acetic acid) and 26.25 grams of Sol B1 (prepared and diafiltered and concentrated as described above, 35.8 wt. % oxide and 3.2 wt. % acetic acid) was charged in to a 500 ml RB flask. Water (41.6 grams) was removed via rotary evaporation resulting in a viscous somewhat dry material. Ethanol (15.1 grams), acrylic acid (2.9 grams), HEMA (1.5 gram) and DI water (1.5 gram) were added to the flask. The contents were stirred overnight resulting is a fluid translucent sol. 2,2'-azobis(2-methylbutyronitrile), ("VAZO 67") (0.15 gram) was added and stirred until dissolved. The contents of the flask were then purged with $N_2$ gas for 3 minutes. The sample (translucent and low viscosity) was charged to cylindrical containers (29 mm diameter). Each container was about 18 ml in volume and each was sealed on both ends (very little air gap was left between the top and liquid). The samples were allowed to stand for about 1 hour then placed in an oven to cure (50° C., 4 hours). This resulted in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

Extraction Process

The wet $ZrO_2$-based gels of Example 14 were removed separately from the ethanol bath, weighed, placed individually inside small canvas pouches, and then stored briefly in another ethanol bath before being loaded into the 10-L extractor vessel. The wet weight of Example 14A sample was 20.7 grams. The wet weight of Example 14B sample was 16.9 grams. About 850 ml of 200-proof ethanol was added to the 10-L extractor of a laboratory-scale supercritical fluid extractor. The canvas bags containing the wet zirconia-based gels of Examples 14A and 14B were transferred from the ethanol bath into the 10-L extractor so that the wet gels were completely immersed in the liquid ethanol inside the jacketed extractor vessel, which was heated and maintained at 60° C. The Example 14A and 14B samples were subjected to the same extraction process as described above for Examples 1 and 2 samples. Afterwards, the dry aerogels were removed from their canvas pouches, weighed, and transferred into individual 237 ml glass jars packed with tissue paper for storage. The dry Example 14A aerogel was semi-translucent with a bluish tint and weighed 11.5 grams, corresponding to an overall weight loss during the supercritical extraction process of 44.4%. The dry Example 14B aerogel was semi-translucent with a bluish tint and weighed 9.5 grams, corresponding to an overall weight loss during the supercritical extraction process of 43.8%.

Organic Burnout and Pre-sinter Process

The extracted Example 14A and 14B aerogel samples from above were removed from their closed containers and immediately set on a bed of zirconia beads in an unglazed porcelain crucible, covered with alumina fiberboard then fired in air according to the following schedule in a THERMOLYNE Type 46200 high temperature furnace: i—heat from 20° C. to 225° C. at 18° C./hr. rate; ii-hold at 225° C. for 24 hours; iii—heat from 225° C. to 400° C. at 6° C./hr. rate; iv—heat from 400° C. to 600° C. at 18° C./hr. rate;

v—heat from 600° C. to 1090° C. at 120° C./hr. rate; and vi—cool down from 1090° C. to 20° C. at 600° C./hr. rate.

After firing the samples were crack free. The sample of Example 14A cylinder was diced into about 1 mm or 2 mm thick wafers. The sample wafers were ion exchanged by first placing them in a 118 ml glass jar containing distilled water at a depth of about 2.5 cm and then vacuum infiltrating. The water was replaced with about a 2.5 cm depth of 1.0N NH$_4$OH and the wafers were soaked overnight for 16 hours or longer. The NH$_4$OH was then poured off and the jar was filled with distilled water. The wafers were soaked in the distilled water for 1 hour. The water was then replaced with fresh distilled water. This step was repeated until the pH of the soak water was equal to that of fresh distilled water. The wafers were then dried at 90-125° C. for a minimum of 1 hour. The pre-sintered (at 1090° C.) aerogel of Example 14A had 44.3 volume % of oxides as determined by dividing the geometric density of the pre-sintered wafer by the Archimedes density of the sintered wafer and then multiplying by 100.

Sintering Process

A 2 mm wafer was set on a bed of zirconia beads in an alumina crucible, covered with alumina fiberboard then sintered in air according to the following schedule in a LINDBERG/BLUE M 1700° C. crucible furnace model 56724: i—heat from 20° C. to 1090° C. at 600° C./hr. rate; ii—heat from 1090° C. to 1250° C. at 120° C./hr. rate; iii—hold at 1250° C. for 2 hours; and iv—cool down from 1250° C. to 20° C. at 600° C./hr. rate.

The wafer was polished on both faces using Buehler polishing equipment comprised of an electrically driven head ("VECTOR POWER HEAD") and a grinder-polisher ("BETA GRINDER-POLISHER"). The sample was ground flat on both sides using 30 micrometer diamond lapping film ("3M DIAMOND LAPPING FILM 668X"). Then 9 micrometer diamond lapping film ("3M DIAMOND LAPPING FILM 668X") was used on both sides until the majority of the 30 micrometer scratches were removed. Next the sample was polished on both sides using 6 micrometer diamond suspension ("METADI DIAMOND SUSPENSION") on a polishing cloth ("TEXMET POLISHING CLOTH"), until the majority of the 9 micrometer scratches were removed. Finally the sample was polished on both sides using 3 micrometer diamond suspension ("METADI DIAMOND SUSPENSION") on a polishing cloth ("TEXMET POLISHING CLOTH"), until the majority of the 6 micrometer scratches were removed. The sample was translucent and lines were distinct when the sample was placed directly on top of them and at a distance. The sample appeared reddish in color in transmitted light and appeared bluish in color in reflected light. The Archimedes density and T/T$_L$ were measured as described above. The samples were set on a bed of zirconia beads in an alumina crucible and thermally etched in air in a rapid temperature furnace (CM Furnaces Inc.) as follows: i—heat from 20° C. to 1200° C. at 450° C./hr. rate; ii—hold at 1200° C. for 0.5 hour; and iii—cool from 1200° C. to 20° C. at 600° C./hr. rate.

FESEM was done on the thermally etched sample as described in the test method described above. The grain size was determined using the line intercept method described in the test method above.

The sintered Example 14A sample had an Archimedes density of 6.01 g/cm$^3$, a polished T/T$_L$ of 2.4 at a polished thickness of 1 mm, and an average grain size of 336 nm.

EXAMPLE 15-17

For Example 15, 38.2 grams of diafiltered and concentrated Sol C1 (35.6 wt. % oxide and about 3.7 wt. % acetic acid) and MEEAA (0.4 gram) were charged to a 500 ml RB flask and mixed. Methoxypropanol (25 grams), acrylic acid (1.4 gram) and HEMA (0.73 gram) were added to the flask. Water and methoxypropanol (32.6 grams) were removed via rotary evaporation. 2,2'-azobis(2-methylbutyronitrile), ("VAZO 67") (0.07 gram) was added and stirred until dissolved. The contents of the flask were then purged with N$_2$ gas for 3 minutes. The sample (translucent and low viscosity) was charged to cylindrical containers (29 mm diameter). Each container was about 18 ml in volume and each was sealed on both ends (very little air gap was left between the top and liquid). The samples were allowed to stand for about 1 hour then placed in an oven to cure (50° C., 4 hours). This resulted in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

For Example 16, 117.85 grams of diafiltered and concentrated Sol C2 (23.1 wt. % oxide and 2.4 wt. % acetic acid) was charged to a 500 ml RB flask. Water (67.85 grams) was removed via rotary evaporation resulting in a viscous somewhat dry material. Ethanol (15.15 grams), acrylic acid (2.9 grams), acrylamide (0.9 gram) and DI water (1.2 gram) were added to the flask. The contents were stirred overnight resulting is a fluid translucent sol. 2,2'-azobis(2-methylbutyronitrile), ("VAZO 67") (0.15 gram) was added and stirred until dissolved. The contents of the flask were then purged with N$_2$ gas for 3 minutes. The sample (translucent and low viscosity) was charged to cylindrical containers (29 mm diameter). Each container was about 18 ml in volume and each was sealed on both ends (very little air gap was left between the top and liquid). The samples were allowed to stand for about 1 hour then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

For Examples 17A and 17B, 92.38 grams of diafiltered and concentrated Sol C3 (29.5 wt. % oxide and 3.1 wt. % acetic acid) was charged to a 500 ml RB flask. Water (42.4 grams) was removed via rotary evaporation resulting in a viscous somewhat dry material. Ethanol (15.1 grams), acrylic acid (2.9 grams), 1-vinyl-2-pyrrolidione (1.5 gram) were added to the flask. The contents were stirred overnight resulting in a fluid translucent sol. 2,2'-azobis(2-methylbutyronitrile), ("VAZO 67") (0.15 gram) was added and stirred until dissolved. The contents of the flask were then purged with N$_2$ gas for 3 minutes). The sample (translucent and low viscosity) was charged to cylindrical containers (29 mm diameter). Each container was about 18 ml in volume and each was sealed on both ends (very little air gap was left between the top and liquid). The samples were allowed to stand for about 1 hour then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

Extraction Process

The wet $ZrO_2$-based gel of Example 15 was removed from the methoxypropanol bath, weighed, placed inside a small canvas pouch, and then stored briefly in another methoxypropanol bath. The wet weight of Example 15 sample was 25.1 grams. About 735 ml of methoxypropanol was added to the 10-L extractor of a laboratory-scale supercritical fluid extractor unit designed by and obtained from Thar Process, Inc., Pittsburgh, Pa. The canvas bag containing the wet zirconia-based gel was transferred from the methoxypropanol bath into the 10-L extractor so that the wet gels were completely immersed in the liquid methoxypropanol inside the jacketed extractor vessel, which was heated and maintained at 60° C. After the extractor vessel lid was sealed in place, liquid carbon dioxide was pumped by a chilled piston pump (setpoint: 12.5° C.) through a heat exchanger to heat the $CO_2$ to 60° C. and into the 10-L extractor vessel until an internal pressure of 13.3 MPa was reached. At these conditions, carbon dioxide is supercritical. Once the extractor operating conditions of 13.3 MPa and 60° C. were met, a PID-controlled needle valve regulated the pressure inside the extractor vessel by opening and closing to allow the extractor effluent to pass through a porous 316L stainless steel frit (obtained from Mott Corporation, New Britain, Conn., under model #1100S-5.480 DIA-.062-10-A), then through a heat exchanger to cool the effluent to 30° C., and finally into a 5-L cyclone separator vessel that was maintained at room temperature and pressure less than 5.5 MPa, where the extracted methoxypropanol and gas-phase $CO_2$ were separated and collected throughout the extraction cycle for recycling and reuse. Supercritical carbon dioxide (scCO$_2$) was pumped continuously through the 10-L extractor vessel for 7 hours from the time the operating conditions were achieved. After the 7-hour extraction cycle, the extractor vessel was slowly vented into the cyclone separator over 16 hours from 13.3 MPa to atmospheric pressure at 60° C. before the lid was opened and the dried canvas pouch containing the Example 15 aerogel was removed. The dry aerogel was removed from its canvas pouch, weighed, and transferred into a 237 ml glass jar packed with tissue paper for storage. The dry Example 15 aerogel was semi-translucent with a bluish tint and weighed 14.3 g, corresponding to an overall weight loss during the supercritical extraction process of 43%.

The wet $ZrO_2$-based gels of Examples 16 and 17 were removed separately from the ethanol bath, weighed, placed individually inside small canvas pouches, and then stored briefly in another ethanol bath before being loaded into the 10-L extractor vessel. The wet weight of Example 16 sample was 21.4 grams. The wet weight of Example 17A sample was 19 grams. The wet weight of Example 17B sample was 21.2 grams. For extraction of both Examples 16 and 17, about 800 ml of 200-proof ethanol was added to the 10-L extractor of a laboratory-scale supercritical fluid extractor. The canvas bags containing the wet zirconia-based gels were transferred from the ethanol bath into the 10-L extractor so that the wet gels were completely immersed in the liquid ethanol inside the jacketed extractor vessel, which was heated and maintained at 60° C. The Example 16 and 17 samples were subjected to the same extraction process as described above for Examples 1 and 2 samples. Afterwards, the dry aerogels were removed from their canvas pouches, weighed, and transferred into individual 237 ml glass jars packed with tissue paper for storage. The dry Example 16 aerogel was semi-translucent with a bluish tint and weighed 11.6 grams, corresponding to an overall weight loss during the supercritical extraction process of 45.8%. The dry Example 17A aerogel was semi-translucent with a bluish tint and weighed 10.4 grams, corresponding to an overall weight loss during the supercritical extraction process of 45.3%. The dry Example 17B aerogel was semi-translucent with a bluish tint.

Organic Burnout and Pre-sinter Process

The extracted Example 15 sample was set on alumina fiberboard supports in an unglazed porcelain crucible, covered with an alumina fiberboard then fired in air according to the following schedule in a THERMOLYNE Type 46200 high temperature furnace: i—heat from 20° C. to 225° C. at 18° C./hr. rate; ii—hold at 225° C. for 24 hours; iii—heat from 225° C. to 400° C. at 6° C./hr. rate; iv—heat from 400° C. to 600° C. at 18° C./hr. rate; and v—cool down from 600° C. to 20° C. at 600° C./hr. rate.

After organic burnout a piece of the sample was set on an alumina fiberboard support in an alumina crucible, covered with an alumina fiberboard then fired in air according to the following schedule in a crucible furnace (Model 56724; "LINDBERG/BLUE M 1700° C."): i—heat from 20° C. to 665° C. at 600° C./hr. rate; ii—heat from 665° C. to 1090° C. at 120° C./hr. rate; and iii—cool down from 1090° C. to 20° C. at 600° C./hr. rate.

The fired sample was diced into about 1 mm thick wafers. The wafers were ion exchanged by first placing them in a 118 ml glass jar containing distilled water at a depth of about 2.5 cm and then vacuum infiltrating. The water was replaced with about a 2.5 cm depth of 1.0N NH$_4$OH and the wafers were soaked overnight for 16 hours or longer. The NH$_4$OH was then poured off and the jar was filled with distilled water. The wafers were soaked in the distilled water for 1 hour. The water was then replaced with fresh distilled water. This step was repeated until the pH of the soak water was equal to that of fresh distilled water. The wafers were then dried at 90-125° C. for a minimum of 1 hour.

The Example 16 sample from above was placed in a 118 ml glass jar with a lid. The lid had a 6.35 mm diameter hole in the top in order to achieve slow drying of the sample. The sample was dried in this way for 402 hours and had a weight loss of 2%. The sample was set on a bed of zirconia beads in an unglazed porcelain crucible, covered with an alumina fiberboard then fired in air according to following schedule in a high temperature furnace ("THERMOLYNE TYPE 46200): i—heat from 20° C. to 225° C. at 18° C./hr. rate; ii—hold at 225° C. for 24 hours; iii—heat from 225° C. to 400° C. at 6° C./hr. rate; iv—heat from 400° C. to 600° C. at 18° C./hr. rate; v—heat from 600° C. to 1090° C. at 120° C./hr·rate; and vi—cool down from 1090° C. to 20° C. at 600° C./hr. rate.

After firing the sample was crack free. The cylinder was diced into about 1 mm thick wafers. The wafers were ion exchanged by first placing them in a 118 ml glass jar containing distilled water at a depth of about 2.5 cm and then vacuum infiltrating. The water was replaced with about 2.5 cm depth of 1.0N NH$_4$OH and the wafers were soaked overnight for about 17 hours. The NH$_4$OH was then poured off and the jar was filled with distilled water. The wafers were soaked in the distilled water for 1 hour. The water was then replaced with fresh distilled water. This step was repeated until the pH of the soak water was equal to that of fresh distilled water. The wafers were then dried at 90-125° C. for a minimum of 1 hour.

The extracted Example 17A aerogel sample from above was analyzed to determine the BET surface area, pore size and porosity. The aerogel of Example 17A had 274 $M^2/g$ of surface area MBET, 0.820 $cm^3/g$ of total pore volume and 120 A of average pore diameter.

The extracted Example 17B aerogel sample from above was removed from its closed container and placed in a 118 ml glass jar with a lid. The lid had a 6.35 mm diameter hole in the top in order to achieve slow drying of the sample. The sample was dried in this way for 1 hours prior to being set on a bed of zirconia beads in an unglazed porcelain crucible, covered with alumina fiberboard then fired in air according to the following schedule in a high temperature furnace ("THERMOLYNE Type 46200"): i—heat from 20° C. to 225° C. at 18° C./hr. rate; ii—hold at 225° C. for 24 hours; iii—heat from 225° C. to 400° C. at 6° C./hr. rate; iv—heat from 400° C. to 600° C. at 18° C./hr. rate; v—heat from 600° C. to 1090° C. at 120° C./hr. rate; and vi—cool down from 1090° C. to 20° C. at 600° C./hr. rate.

After firing the sample was crack free. The cylinder was diced into about 2.5 mm thick wafers. The Example 17B sample wafers were ion exchanged by first placing them in a 118 ml glass jar containing distilled water at a depth of about 2.5 cm and then vacuum infiltrating. The water was replaced with about a 2.5 cm depth of 1.0N $NH_4OH$ and the wafers were soaked overnight for 16 hours or longer. The $NH_4OH$ was then poured off and the jar was filled with distilled water. The wafers were soaked in the distilled water for 1 hour. The water was then replaced with fresh distilled water. This step was repeated until the pH of the soak water was equal to that of fresh distilled water. The wafers were then dried at 90° C. for a minimum of 1 hour. The aerogel of Example 16 had 11.65 volume % of oxides while the pre-sintered at 1090° C. aerogel of Example 16 had 53.1 volume % of oxides. The volume percent oxide values were calculated using the method described above. The pre-sintered at 1090° C. aerogel of Example 17B had 47.9 volume % of oxides, as determined by dividing the geometric density of the pre-sintered wafer by the Archimedes density of the sintered wafer and then multiplying by 100.

Sintering Process

An Example 15 sample wafer was set on a bed of zirconia beads in an alumina crucible, covered with alumina fiberboard then sintered in air according to the following schedule in a crucible furnace (Model 56724; "LINDBERG/BLUE M 1700° C."): i—heat from 20° C. to 1090° C. at 600° C./hr. rate; ii—heat from 1090° C. to 1210° C. at 120° C./hr. rate; iii—hold at 1210° C. for 2 hours; and iv—cool down from 1210° C. to 20° C. at 600° C./hr. rate.

The sample had a yellowish brown color. The as fired wafer was analyzed by XRD. One face of the wafer was polished using polishing equipment comprised of an electrically driven head ("VECTOR POWER HEAD") and a grinder-polisher ("BETA GRINDER-POLISHER"). The sample was ground flat using 30 micrometer diamond lapping film ("3M DIAMOND LAPPING FILM 668X"). Then 9 micrometer diamond lapping film ("3M DIAMOND LAPPING FILM 668X") was used until the majority of the 30 micrometer scratches were removed. Next the sample was polished using 6 micrometer diamond suspension ("METADI DIAMOND SUSPENSION") on a polishing cloth ("TEXMET POLISHING CLOTH") until the majority of the 9 micrometer scratches were removed. Finally the sample was polished using 3 micrometer diamond suspension ("METADI DIAMOND SUSPENSION") on a polishing cloth ("TEXMET POLISHING CLOTH") until the majority of the 6 micrometer scratches were removed. The polished wafer was set on a bed of zirconia beads in an alumina crucible and thermally etched in air in a rapid temperature furnace (CM Furnaces Inc.) as follows: i—heat from 20° C. to 1160° C. at 450° C./hr. rate; ii—hold at 1160° C. for 0.5 hour; and iii—cool from 1160° C. to 20° C. at 600° C./hr. rate.

FESEM was done on the thermally etched sample as described in the test method described above. The grain size was determined using the line intercept method described in the test methods above.

One of the dried Example 16 wafers was set on a bed of zirconia beads in an alumina crucible, covered with an alumina fiberboard then sintered in air according to following schedule in a LINDBERG/BLUE M 1700° C. Crucible Furnace model 56724 obtained from Thermo Fischer Scientific, Waltham, Mass.: i—heat from 20° C. to 1090° C. at 600° C./hr. rate, ii—heat from 1090° C. to 1250° C. at 120° C./hr. rate, iii—hold at 1250° C. for 2 hours. iv—cool down from 1250° C. to 20° C. at 600° C./hr. rate.

The fired sample was transparent and colorless. The sample was polished using Buehler polishing equipment comprised of an electrically driven head ("VECTOR POWER HEAD" and a grinder-polisher ("BETA GRINDER-POLISHER"). The sample was ground flat on both sides using 30 micrometer diamond lapping film ("3M DIAMOND LAPPING FILM 668X"). Then 9 micrometer diamond lapping film ("3M DIAMOND LAPPING FILM 668X") was used on both sides until the majority of the 30 micrometer scratches were removed. Next the sample was polished on both sides using 6 micrometer diamond suspension ("METADI DIAMOND SUSPENSION") on a polishing cloth ("TEXMET POLISHING CLOTH") until the majority of the 9 micrometer scratches were removed. Finally the sample was polished on both sides using 3 micrometer diamond suspension ("METADI DIAMOND SUSPENSION") on a polishing cloth ("TEXMET POLISHING CLOTH") until the majority of the 6 micrometer scratches were removed. The fired and polished wafer is translucent and lines were distinct when the sample was placed directly on top of them. The Archimedes density and $T/T_L$ were measured as described above.

Wafers of the Example 17B sample were set on a bed of zirconia beads in an alumina crucible, covered with alumina fiberboard then sintered in air according to the following schedule in a crucible furnace (Model 56724; "LINDBERG/BLUE M 1700° C."): i—heat from 20° C. to 1090° C. at 600° C./hr. rate; ii—heat from 1090° C. to 1250° C. at 120° C./hr. rate; iii—hold at 1250° C. for 2 hours; and iv—cool down from 1250° C. to 20° C. at 600° C./hr. rate.

The 2.5 mm wafers were polished on one face using a 12 open face lapping machine ("LAPMASTER") for all but the final polishing step. The biaxial flexural strength was measured on the 2.5 mm samples after polishing using the test method above. The samples were all adhered to a sample plate and were then ground flat using a 20 micrometer diamond tile ("3M TRIZACT DIAMOND TILE") at a speed of 30 rpm. The abrasive was then switched to a 9 micrometer diamond tile ("3M TRIZACT DIAMOND TILE") and grinding continued at 30 rpm until the majority of the 20 micrometer scratches were removed. The abrasive was then switched to a 3 micrometer diamond tile ("3M TRIZACT DIAMOND TILE") and grinding continued at 30 rpm until the majority of the 9 micrometer scratches were removed. The final polish was done using Buehler polishing equipment comprised of an electrically driven head ("VECTOR POWER HEAD") and a grinder-polisher ("BETA GRINDER-POLISHER") and 3 micrometer diamond suspension ("METADI DIAMOND SUSPENSION") on a polishing cloth ("TEXMET POLISHING CLOTH") until the majority of the scratches were removed. After strength testing a piece of aerogel Example 17B was set on a bed of zirconia beads in an alumina crucible and thermally etched in air in a rapid temperature furnace (CM Furnaces Inc.) as follows: i—heat from 20° C. to 1200° C. at 450° C./hr. rate; ii—hold at 1200° C. for 0.5 hour; and iii—cool from 1200° C. to 20° C. at 600° C./hr. rate.

FESEM was done on the thermally etched sample as described in the test method described above. The grain size was determined using the line intercept method described in the test methods above.

One of the Example 17B biaxial flexural strength sample fragments was submitted for XRD analysis.

The properties of the sintered wafers are given in Table 7, below.

TABLE 7

| Example | Archimedes Density, g/cm$^3$ | Polished Thickness, mm | Polished T/T$_L$ | Grain Size, nm | Strength, MPa | Composition (XRD) |
|---|---|---|---|---|---|---|
| 15 | | | | 262 | | [ZrO2(C) major a = 5.138] |
| 16 | 5.98 | 0.47 | 1.97 | | | |
| 17B | 5.96 | 1.71 | | 497 | 340 | [ZrO2(C) a = 5.15] |

EXAMPLE 18

For Example 18, 83.1 grams of diafiltered and concentrated Sol C3 (29.5 wt. % oxide and 3.15 wt. % Acetic acid) was charged to 500 ml RB flask. Water (42.45 grams) was removed via rotary evaporation resulting in a viscous somewhat dry material. Ethanol (15.2 grams), acrylic acid (2.9 grams), HEMA (1.5 gram) were added to the flask. The contents were stirred overnight resulting in a fluid translucent sol. 2,2'-azobis(2-methylbutyronitrile), ("VAZO 67") (0.15 gram) was added and stirred until dissolved. The contents of the flask were then purged with N$_2$ gas for 3 minutes. The sample (translucent and low viscosity) was charged to cylindrical containers (29 mm diameter). Each container was about 18 ml in volume and each was sealed on both ends (very little air gap was left between the top and liquid). The samples were allowed to stand for about 1 hour then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

Extraction Process

The wet ZrO$_2$-based gel of Example 18 was removed from the ethanol bath, weighed, placed inside a small canvas pouch, and then stored briefly in another ethanol bath before being loaded into the 10-L extractor vessel. The wet weight of Example 18 was 11.6 grams. About 765 ml of 200-proof ethanol was added to the 10-L extractor of a laboratory-scale supercritical fluid extractor unit. The canvas bag containing the wet zirconia-based gel was transferred from the ethanol bath into the 10-L extractor so that the wet gel was completely immersed in the liquid ethanol inside the jacketed extractor vessel, which was heated and maintained at 60° C. The Example 18 sample was subjected to the same extraction process as described above for Examples 1 and 2 samples. Afterwards, the dry aerogel was removed from its canvas pouch, weighed, and transferred into a 237 ml glass jar packed with tissue paper for storage. The dry Example 18 aerogel was semi-translucent with a bluish tint and weighed 6.6 g, corresponding to an overall weight loss during the supercritical extraction process of 43.1%.

Organic Burnout and Pre-sinter Process

The extracted Example 18 aerogel sample from above was removed from its closed container and dried for 1 hour in open air prior to being set on a bed of zirconia beads in an unglazed porcelain crucible, covered with alumina fiberboard then fired in air according to the following schedule in a high temperature furnace ("THERMOLYNE TYPE 46200"): i—heat from 20° C. to 225° C. at 18° C./hr. rate; ii—hold at 225° C. for 24 hours; iii—heat from 225° C. to 400° C. at 6° C./hr. rate; iv—heat from 400° C. to 600° C. at 18° C./hr. rate; v—heat from 600° C. to 1090° C. at 120° C./hr. rate; and vi—cool down from 1090° C. to 20° C. at 600° C./hr. rate.

After firing the sample was crack free. The cylinder was diced into about 2 mm thick wafers. The wafers were ion exchanged by first placing them in a 118 ml glass jar containing distilled water at a depth of about 2.5 cm and then vacuum infiltrating. The water was replaced with about a 2.5 cm depth of 1.0N NH$_4$OH and the wafers were soaked overnight for 16 hours or longer. The NH$_4$OH was then poured off and the jar was filled with distilled water. The wafers were soaked in the distilled water for 1 hour. The water was then replaced with fresh distilled water. This step was repeated until the pH of the soak water was equal to that of fresh distilled water. The wafers were then dried at 90-125° C. for a minimum of 1 hour. The pre-sintered (at 1090° C.) aerogel of Example 18 had 47.9 volume % of oxides, as determined by dividing the geometric density of the pre-sintered wafer by the Archimedes density of the sintered wafer and then multiplying by 100.

Sintering Process

The wafer was set on a bed of zirconia beads in an alumina crucible, covered with alumina fiberboard then sintered in air according to the following schedule in a crucible furnace (Model 56724; "LINDBERG/BLUE M 1700° C."): i—heat from 20° C. to 1090° C. at 600° C./hr. rate; ii—heat from 1090° C. to 1250° C. at 120° C./hr. rate; iii—hold at 1250° C. for 2 hours; and iv—cool down from 1250° C. to 20° C. at 600° C./hr. rate. The Archimedes density was measured to be 6 g/cm$^3$ as described in the above procedure.

The sintered wafer of Example 18 was polished on both faces using Buehler polishing equipment comprised of an electrically driven head ("VECTOR POWER HEAD") and a grinder-polisher ("BETA GRINDER-POLISHER"). First the sample was ground flat using a 45 micrometer metal bonded diamond disc (Part No: 156145 from Buehler). Then 30 micrometer diamond lapping film ("3M DIAMOND LAPPING FILM 668X") was used until the majority of the 45 micrometer scratches were removed. Then 9 micrometer diamond lapping film 3M DIAMOND LAPPING FILM 668X") was used until the majority of the 30 micrometer scratches were removed. Next the sample was polished using 3 micrometer diamond suspension ("METADI DIAMOND SUSPENSION") on a polishing cloth ("TEXMET POLISHING CLOTH") until the majority of the 9 micrometer scratches were removed. Finally the sample was polished using 0.25 micrometer diamond suspension ("METADI DIAMOND SUSPENSION") on a polishing cloth ("TEXMET POLISHING CLOTH") (both obtained from Buehler, Lake Bluff, Ill.) until the majority of the 3 micrometer scratches were removed. The wafer was mounted in a lapping fixture (Model 150 from South Bay Technology, Inc.) during grinding and polishing to maintain flat and parallel faces. The wafer was bonded to the lapping fixture using hot-melt adhesive ("QUICKSTICK 135"). One side of the wafer was ground and polished, then the wafer was remounted and the other side was ground and polished.

The total transmittance was 61.5%, the diffuse transmittance was 11.8%, and the haze was 19.1%, measured using the spectrophotometer procedure described earlier. The TLT and DLT spectra are designated in FIGS. 2 and 3 as 1018 and 1118, respectively. The sample thickness was 1.01 mm.

EXAMPLE 19

For Example 19A, 19B, and 19C a 24.4 gram sample of Sol C4 (prepared and diafiltered and concentrated as described above, 27.9 wt. % oxide and 3 wt. % acetic acid) and 76.6 grams of Sol T2 (prepared and diafiltered and concentrated as described above, 26.6 wt. % oxide and 2.9 wt. % acetic acid) was charged in to a 500 mL RB flask. Water (52.5 gram) was removed via rotary evaporation resulting in a viscous somewhat dry material. Ethanol (15.1 gram), acrylic acid (2.9 gram), HEMA (1.5 gram) and DI water (1.5 gram) were added to the flask. The contents were stirred overnight resulting is a fluid translucent sol. 2,2'-azobis(2-methylbutyronitrile), ("VAZO 67") (0.15 gram) was added and stirred until dissolved. The contents of the flask were then purged with $N_2$ gas for 3 minutes). The sample (translucent and low viscosity) was charged to cylindrical containers (29 mm diameter). Each container was about 18 mL in volume and each was sealed on both ends (very little air gap was left between the top and liquid). The samples were allowed to stand for about 1 hour then placed in an oven to cure (50° C., 4 hours). This resulted in a clear translucent blue gel. The gels were removed from their containers and placed in a 473 mL wide mouth jar. The jar was filled with ethanol (denatured). The samples were soaked for 24 hours then the ethanol was replaced with fresh ethanol. The samples were soaked for 24 hours then the ethanol was replaced with a third batch of fresh ethanol. The samples were allowed to soak until the supercritical extraction was done. The above manipulations were done minimizing the amount of time the gels were exposed to the air.

Extraction Process

The wet $ZrO_2$-based gels of Example 19A, 19B, and 19C were removed from the ethanol bath, weighed, placed inside small canvas pouches, and then stored briefly in another ethanol bath before being loaded into the 10-L extractor vessel. The wet weight of Example 19A was 20.8 grams. The wet weight of Example 19B was 19.5 grams. The wet weight of Example 19C was 20.3 grams. About 735 mL of 200-proof ethanol was added to the 10-L extractor of a laboratory-scale supercritical fluid extractor unit. The canvas bags containing the wet zirconia-based gels were transferred from the ethanol bath into the 10-L extractor so that the wet gels were completely immersed in the liquid ethanol inside the jacketed extractor vessel, which was heated and maintained at 60° C. The Example 19 samples were subjected to the same extraction process as described above for Examples 1 and 2 samples. Afterwards, the dry aerogels were removed from their canvas pouches, weighed, and transferred into a 237 mL glass jar packed with tissue paper for storage. The dry Example 19A aerogel was semi-translucent with a bluish tint and weighed 11.2 grams, corresponding to an overall weight loss during the supercritical extraction process of 46.2%. The dry Example 19B aerogel was semi-translucent with a bluish tint and weighed 10.3 grams, corresponding to an overall weight loss during the supercritical extraction process of 47.2%. The dry Example 19C aerogel was semi-translucent with a bluish tint and weighed 10.9 grams, corresponding to an overall weight loss during the supercritical extraction process of 46.3%.

Organic Burnout and Pre-sinter Process

The extracted Example 19A, 19B, and 19C aerogel samples from above were removed from their closed containers and dried for 1 hour in open air prior to being set on a bed of zirconia beads in an unglazed porcelain crucible, covered with alumina fiberboard then fired in air according to the following schedule in a high temperature furnace ("THERMOLYNE TYPE 46200"): i—heat from 20° C. to 225° C. at 18° C./hr rate; ii—hold at 225° C. for 24 hours; iii—heat from 225° C. to 400° C. at 6° C./hr. rate; iv—heat from 400° C. to 600° C. at 18° C./hr. rate; v—heat from 600° C. to 1090° C. at 120° C./hr. rate; and vi—cool down from 1090° C. to 20° C. at 600° C./hr. rate.

After firing the sample was crack free. The cylinder was diced into about 2 mm thick wafers. The wafers were ion exchanged by first placing them in a 118 mL glass jar containing distilled water at a depth of about 2.5 cm and then vacuum infiltrating. The water was replaced with about a 2.5 cm depth of 1.0N $NH_4OH$ and the wafers were soaked overnight for 16 hours or longer. The $NH_4OH$ was then poured off and the jar was filled with distilled water. The wafers were soaked in the distilled water for 1 hour. The water was then replaced with fresh distilled water. This step was repeated until the pH of the soak water was equal to that of fresh distilled water. The wafers were then dried at 90-125° C. for a minimum of 1 hour. The pre-sintered at 1090° C. aerogels of Example 19A, 19B and 19C had 46.4 volume % of oxides, as determined by dividing the geometric density of the pre-sintered wafer by the Archimedes density of the sintered wafer and then multiplying by 100.

Sintering Process

The wafers were set on a bed of zirconia beads in an alumina crucible, covered with alumina fiberboard then sintered in air according to the following schedule in a crucible furnace (Model 56724; "LINDBERG/BLUE M 1700° C."): i—heat from 20° C. to 1090° C. at 600° C./hr. rate; ii—heat from 1090° C. to 1250° C. at 120° C./hr. rate; iii—hold at 1250° C. for 2 hours; and iv—cool down from 1250° C. to 20° C. at 600° C./hr. rate. The Archimedes density was measured to be 6.1 $g/cm^3$ as described in the above procedure.

A sintered wafer of Example 19C was polished on both faces using Buehler polishing equipment comprised of an electrically driven head ("VECTOR POWER HEAD") and a grinder-polisher ("BETA GRINDER-POLISHER"). First the sample was ground flat using a 45 micrometer metal bonded diamond disc (identified as Part No: 156145, Buehler). Then 30 micrometer diamond lapping film ("3M DIAMOND LAPPING FILM 668X") was used until the majority of the 45 micrometer scratches were removed. Then 9 micrometer diamond lapping film ("3M DIAMOND LAPPING FILM 668X") was used until the majority of the 30 micrometer scratches were removed. Next the sample was polished using 3 micrometer diamond suspension ("METADI DIAMOND SUSPENSION") on a polishing cloth ("TEXMET POLISHING CLOTH") until the majority of the 9 micrometer scratches were removed. Finally the sample was polished using 0.25 micrometer diamond suspension ("METADI DIAMOND SUSPENSION") on a polishing cloth ("TEXMET POLISHING CLOTH") until the majority of the 3 micrometer scratches were removed. The wafer was mounted in a lapping fixture (Model 150, South Bay Technology, Inc.) during grinding and polishing to maintain flat and parallel faces. The wafer was bonded to the lapping fixture using a hot-melt adhesive ("QUICKSTICK 135"). One side of the wafer was ground and polished, then the wafer was remounted and the other side was ground and polished.

The total transmittance was 44.2%, the diffuse transmittance was 29.3%, and the haze was 66.2%, measured using the spectrophotometer procedure described earlier. The TLT and DLT spectra are designated in FIGS. 2 and 3 as 1019 and 1119, respectively. The sample thickness was 0.97 mm.

Wafers of Examples 19A and 19B were subject to the Hydrolytic Stability Test and passed. The wafers of Examples 19A and 19B were subjected to the 5 hour exposure to saturated steam at 135° C. under a pressure of 0.2 MPa for up to five additional times. No phase transformation was observed during these hydrolytic stability tests at each of 5, 10, 15, and 30 hours of exposure.

EXAMPLE 20

For Examples 20A, 20B, 20C, 20D, 20E, and 20F, a 96.9 gram sample of Sol C4 (prepared and diafiltered and concentrated as described above, 27.9 wt. % oxide and 3 wt. % acetic acid) and 102.2 grams of Sol T2 (prepared and diafiltered and concentrated as described above, 26.6 wt. % oxide and 2.9 wt. % acetic acid) was charged in to a 500 mL RB flask. Water (102.2 grams) was removed via rotary evaporation resulting in a viscous somewhat dry material. Ethanol (30.3 grams), acrylic acid (5.8 grams), HEMA (2.9 grams) and DI water (3 grams) were added to the flask. The contents were stirred overnight resulting is a fluid translucent sol. 2,2'-azobis(2-methylbutyronitrile) ("VAZO 67") (0.3 gram) was added and stirred until dissolved. The contents of the flask were then purged with $N_2$ gas for 6 minutes. The sample (translucent and low viscosity) was charged to cylindrical containers (29 mm diameter). Each container was about 18 mL in volume and each was sealed on both ends (very little air gap was left between the top and liquid). The samples were allowed to stand for about 1 hr then placed in an oven to cure (50° C., 4 hours). This results in a clear translucent blue gel. The gels were removed from the containers and placed in a 473 mL wide mouth jar. The jar was filled with ethanol (denatured). The samples were soaked for 24 hours then the ethanol was replaced with fresh ethanol. The samples were soaked for 24 hours then the ethanol was replaced with a third batch of fresh ethanol. The samples were allowed to soak until the supercritical extraction was done. The above manipulations were done minimizing the amount of time the gels were exposed to the air.

Extraction Process

The wet $ZrO_2$-based gel of Example 20A, 20B, 20C, 20D, 20E, and 20F were removed from the ethanol bath, weighed, placed inside small canvas pouches, and then stored briefly in another ethanol bath before being loaded into the 10-L extractor vessel. The wet weight of Example 20A was 21 grams. The wet weight of Example 20B was 19.8 grams. The wet weight of Example 20C was 20.2 grams. The wet weight of Example 20D was 19 grams. The wet weight of Example 20E was 18.1 grams. The wet weight of Example 20F was 21 grams. About 855 mL of 200-proof ethanol was added to the 10-L extractor of a laboratory-scale supercritical fluid extractor unit. The canvas bags containing the wet zirconia-based gels were transferred from the ethanol bath into the 10-L extractor so that the wet gels were completely immersed in the liquid ethanol inside the jacketed extractor vessel, which was heated and maintained at 60° C. The Example 20A, 20B, 20C, 20D, 20E, and 20F samples were subjected to the same extraction process as described above for Examples 1 and 2 samples. Afterwards, the dry aerogels were removed from their canvas pouches, weighed, and transferred into a 237 mL glass jar packed with tissue paper for storage. The dry Example 20A aerogel was semi-translucent with a bluish tint and weighed 11.4 grams, corresponding to an overall weight loss during the supercritical extraction process of 45.7%. The dry Example 20B aerogel was semi-translucent with a bluish tint and weighed 11 grams, corresponding to an overall weight loss during the supercritical extraction process of 44.4%. The dry Example 20C aerogel was semi-translucent with a bluish tint and weighed 11.1 grams, corresponding to an overall weight loss during the supercritical extraction process of 45.1%. The dry Example 20D aerogel was semi-translucent with a bluish tint and weighed 10.6 grams, corresponding to an overall weight loss during the supercritical extraction process of 44.2%. The dry Example 20E aerogel was semi-translucent with a bluish tint and weighed 10 grams, corresponding to an overall weight loss during the supercritical extraction process of 44.8%. The dry Example 20F aerogel was semi-translucent with a bluish tint and weighed 11.6 grams, corresponding to an overall weight loss during the supercritical extraction process of 44.8%.

Organic Burnout and Pre-sinter Process

The extracted Example 20A, 20B, 20C, 20D, 20E, and 20F aerogel samples from above were removed from their closed containers. The Example 20C, 20E, and 20F samples were cracked. The Example 20A, 20B & 20C aerogel samples were crack free and were set on a bed of zirconia beads in an unglazed porcelain crucible, covered with alumina fiberboard then fired in air according to the following schedule in a high temperature furnace ("THERMOLYNE TYPE 46200"): i—heat from 20° C. to 225° C. at 18° C./hr. rate; ii—hold at 225° C. for 24 hours; iii—heat from 225° C. to 400° C. at 6° C./hr. rate; iv—heat from 400° C. to 600° C. at 18° C./hr. rate; v—heat from 600° C. to 1090° C. at 120° C./hr. rate; and vi—cool down from 1090° C. to 20° C. at 600° C./hr. rate.

After firing the Example 20B and 20D samples were crack free. The Example 20A sample was cracked. The Example 20B and 20D samples were diced into about 2 mm thick wafers. The wafers were ion exchanged by first placing them in a 118 mL glass jar containing distilled water at a depth of about 2.5 cm and then vacuum infiltrating. The water was replaced with about a 2.5 cm depth of 1.0N $NH_4OH$ and the wafers were soaked overnight for 16 hours or longer. The $NH_4OH$ was then poured off and the jar was filled with distilled water. The wafers were soaked in the distilled water for 1 hour. The water was then replaced with fresh distilled water. This step was repeated until the pH of the soak water was equal to that of fresh distilled water. The wafers were then dried at 90-125° C. for a minimum of 1 hour. The pre-sintered at 1090° C. aerogels of Example 20B and 20D had 44.4 volume % of oxides, as determined by dividing the geometric density of the pre-sintered wafer by the Archimedes density of the sintered wafer and then multiplying by 100.

Sintering Process

The wafers were set on a bed of zirconia beads in an alumina crucible, covered with alumina fiberboard then sintered in air according to the following schedule in a crucible furnace (Model 56724; "LINDBERG/BLUE M 1700° C."): i—heat from 20° C. to 1090° C. at 600° C./hr. rate; ii—heat from 1090° C. to 1250° C. at 120° C./hr. rate; iii—hold at 1250° C. for 2 hours; and iv—cool down from 1250° C. to 20° C. at 600° C./hr. rate. The Archimedes density was measured to be 6.04 g/cm$^3$ as described in the above procedure.

A sintered wafer of Example 20D was polished on both faces using Buehler polishing equipment comprised of an electrically driven head ("VECTOR POWER HEAD") and a grinder-polisher ("BETA GRINDER-POLISHER"). First the sample was ground flat using a 45 micrometer metal bonded diamond disc (identified as Part No: 156145 from Buehler). Then 30 micrometer diamond lapping film ("3M DIAMOND LAPPING FILM 668X") was used until the majority of the 45 micrometer scratches were removed. Then 9 micrometer diamond lapping film ("3M DIAMOND LAPPING FILM 668X") was used until the majority of the 30 micrometer scratches were removed. Next the sample was polished using 3 micrometer diamond suspension ("METADI DIAMOND SUSPENSION") on a polishing cloth ("TEXMET POLISHING CLOTH") until the majority of the 9 micrometer scratches were removed. Finally the sample was polished using 0.25 micrometer diamond suspension ("METADI DIAMOND SUSPENSION") on a polishing cloth ("TEXMET POLISHING CLOTH") until the majority of the 3 micrometer scratches were removed. The wafer was mounted in a lapping fixture during grinding and polishing to maintain flat and parallel faces. The wafer was bonded to the lapping fixture using hot-melt adhesive ("QUICKSTICK 135"). One side of the wafer was ground and polished, then the wafer was remounted and the other side was ground and polished.

The total transmittance was 58.3%, the diffuse transmittance was 14.2%, and the haze was 24.3%, measured using the spectrophotometer procedure described earlier. The TLT and DLT spectra are designated in FIGS. 2 and 3 as 1020 and 1120, respectively. The sample thickness was 1.01 mm.

A wafer of Examples 20B was subject to the Hydrolytic Stability Test and passed. The wafer of Example 20B was subjected to the 5 hour exposure to saturated steam at 135° C. under a pressure of 0.2 MPa for up to five additional times. No phase transformation was observed during these hydrolytic stability tests at each of 5, 10, 15, and 30 hours of exposure.

EXAMPLE 21

For Example 21A, 21B, 21C, 21D, 21E, and 21F a 146.1 gram sample of Sol C4 (prepared and diafiltered and concentrated as described above, 27.9 wt. % oxide and 3 wt. % acetic acid) and 51.1 grams of Sol T2 (prepared and diafiltered and concentrated as described above, 26.6 wt. % oxide and 2.9 wt. % acetic acid) was charged in to a 500 mL RB flask. Water (100.2 grams) was removed via rotary evaporation resulting in a viscous somewhat dry material. Ethanol (30.3 grams), acrylic acid (5.8 grams), HEMA (2.95 grams) and DI water (3 grams) were added to the flask. The contents were stirred overnight resulting in a fluid translucent sol. 2,2'-azobis(2-methylbutyronitrile), ("VAZO 67") (0.3 gram) was added and stirred until dissolved. The contents of the flask were then purged with $N_2$ gas for 6 minutes. The sample (translucent and low viscosity) was charged to cylindrical containers (29 mm diameter). Each container was about 18 mL in volume and each was sealed on both ends (very little air gap was left between the top and liquid). The samples were allowed to stand for about 1 hr then placed in an oven to cure (50° C., 4 hours). This results in a clear translucent blue gel. The gels were removed from the containers and placed in a 473 mL wide mouth jar. The jar was filled with ethanol (denatured). The samples were soaked for 24 hours then the ethanol was replaced with fresh ethanol. The samples were soaked for 24 hours then the ethanol was replaced with a third batch of fresh ethanol. The samples were allowed to soak until the supercritical extraction was done. The above manipulations were done minimizing the amount of time the gels were exposed to the air.

Extraction Process

The wet $ZrO_2$-based gels of Example 21A, 21B, 21C, 21D, 21E, and 21F were removed from the ethanol bath, weighed, placed inside small canvas pouches, and then stored briefly in another ethanol bath before being loaded into the 10-L extractor vessel. The wet weight of Example 21A was 21.8 grams. The wet weight of Example 21B was 20.4 grams. The wet weight of Example 21C was 20.9 grams. The wet weight of Example 21D was 20.9 grams. The wet weight of Example 21E was 21.2 grams. The wet weight of Example 21F was 14 grams. About 735 mL of 200-proof ethanol was added to the 10-L extractor of a laboratory-scale supercritical fluid extractor unit. The canvas bags containing the wet zirconia-based gels were transferred from the ethanol bath into the 10-L extractor so that the wet gels were completely immersed in the liquid ethanol inside the jacketed extractor vessel, which was heated and maintained at 60° C. The Example 21A, 21B, 21C, 21D, 21E, and 21F samples were subjected to the same extraction process as described above for Examples 1 and 2 samples. Afterwards, the dry aerogels were removed from their canvas pouches, weighed, and transferred into a 237 mL glass jar packed with tissue paper for storage. The dry Example 21A aerogel was semi-translucent with a bluish tint and weighed 11.9 grams, corresponding to an overall weight loss during the supercritical extraction process of 45.4%. The dry Example 21B aerogel was semi-translucent with a bluish tint and weighed 11.1 grams, corresponding to an overall weight loss during the supercritical extraction process of 45.6%. The dry Example 21C aerogel was semi-translucent with a bluish tint and weighed 11.3 grams, corresponding to an overall weight loss during the supercritical extraction process of 45.9%. The dry Example 21D aerogel was opaque and cracked and weighed 12.7 grams, corresponding to an overall weight loss during the supercritical extraction process of 39.2%. The dry Example 21E aerogel was opaque and cracked and weighed 12.7 grams, corresponding to an overall weight loss during the supercritical extraction process of 40.1%. The dry Example 21F aerogel was opaque and cracked and weighed 8.5 grams, corresponding to an overall weight loss during the supercritical extraction process of 39.3%.

Organic Burnout and Pre-sinter Process

The extracted Example 21A, 21B, and 21C aerogel samples from above were removed from their closed container and set on a bed of zirconia beads in an unglazed porcelain crucible, covered with alumina fiberboard then fired in air according to the following schedule in a high temperature furnace ("THERMOLYNE TYPE 46200"): i—heat from 20° C. to 225° C. at 18° C./hr. rate; ii—hold at 225° C. for 24 hours; iii—heat from 225° C. to 400° C. at 6° C./hr. rate; iv—heat from 400° C. to 600° C. at 18° C./hr. rate; v—heat from 600° C. to 1090° C. at 120° C./hr. rate; and vi—cool down from 1090° C. to 20° C. at 600° C./hr. rate.

After firing the samples were crack free. The cylinders were diced into about 2 mm thick wafers. The wafers were ion exchanged by first placing them in a 118 mL glass jar containing distilled water at a depth of about 2.5 cm and then vacuum infiltrating. The water was replaced with about a 2.5 cm depth of 1.0N NH$_4$OH and the wafers were soaked overnight for 16 hours or longer. The NH$_4$OH was then poured off and the jar was filled with distilled water. The wafers were soaked in the distilled water for 1 hour. The water was then replaced with fresh distilled water. This step was repeated until the pH of the soak water was equal to that of fresh distilled water. The wafers were then dried at 90-125° C. for a minimum of 1 hour. The pre-sintered at 1090° C. aerogels of Example 21A, 21B, and 21C had 46.6 volume % of oxides, as determined by dividing the geometric density of the pre-sintered wafer by the Archimedes density of the sintered wafer and then multiplying by 100.

Sintering Process

The Example 21A, 21B, and 21C wafers were set on a bed of zirconia beads in an alumina crucible, covered with alumina fiberboard then sintered in air according to the following schedule in a crucible furnace (Model 56724; "LINDBERG/BLUE M 1700° C."): i—heat from 20° C. to 1090° C. at 600° C./hr. rate; ii—heat from 1090° C. to 1250° C. at 120° C./hr. rate; iii—hold at 1250° C. for 2 hours; and iv—cool down from 1250° C. to 20° C. at 600° C./hr. rate. The Archimedes density was measured to be 6 g/cm$^3$ as described in the above procedure.

A sintered wafer of Example 21C was polished on both faces using Buehler polishing equipment comprised of an electrically driven head ("VECTOR POWER HEAD") and a grinder-polisher ("BETA GRINDER-POLISHER"). First the sample was ground flat using a 45 micrometer metal bonded diamond disc (identified as Part No: 156145 from Buehler). Then 30 micrometer diamond lapping film ("3M DIAMOND LAPPING FILM 668X") was used until the majority of the 45 micrometer scratches were removed. Then 9 micrometer diamond lapping film ("3M DIAMOND LAPPING FILM 668X") was used until the majority of the 30 micrometer scratches were removed. Next the sample was polished using 3 micrometer diamond suspension ("METADI DIAMOND SUSPENSION") on a polishing cloth ("TEXMET POLISHING CLOTH") until the majority of the 9 micrometer scratches were removed. Finally the sample was polished using 0.25 micrometer diamond suspension ("METADI DIAMOND SUSPENSION") on a polishing cloth ("TEXMET POLISHING CLOTH") until the majority of the 3 micrometer scratches were removed. The wafer was mounted in a lapping fixture during grinding and polishing to maintain flat and parallel faces. The wafer was bonded to the lapping fixture using hot-melt adhesive ("QUICKSTICK 135"). One side of the wafer was ground and polished, then the wafer was remounted and the other side was ground and polished.

The total transmittance was 65.2%, the diffuse transmittance was 8.9%, and the haze was 13.7%, measured using the spectrophotometer procedure described earlier. The TLT and DLT spectra are designated in FIGS. 2 and 3 as 1021 and 1121, respectively. The sample thickness was 1.00 mm.

Wafers of Examples 21A and 21C were subject to the Hydrolytic Stability Test and passed. The wafers of Examples 21A and 21C were subjected to the 5 hour exposure to saturated steam at 135° C. under a pressure of 0.2 MPa for up to five additional times. No phase transformation was observed during these hydrolytic stability tests at each of 5, 10, 15, and 30 hours of exposure.

EXAMPLE 22

For Example 22, 108.2 grams of diafiltered and concentrated Sol A1 (25.6 wt. % oxide and 2.3 wt. % acetic acid) was charged to 500 ml RB flask. Water (58.2 grams) was removed via rotary evaporation resulting in a viscous somewhat dry material. Ethanol (15.2 grams), acrylic acid (2.9 grams), and HEMA (1.5 gram) were added to the flask. The contents were stirred overnight resulting in a fluid translucent sol. 2,2'-azobis(2-methylbutyronitrile) ("VAZO 67") (0.15 gram) was added and stirred until dissolved. The contents of the flask were then purged with N$_2$ gas for 3 minutes. The sample (translucent and low viscosity) was charged to cylindrical containers (29 mm diameter). Each container was about 18 ml in volume and each was sealed on both ends (very little air gap was left between the top and liquid). The samples were allowed to stand for about 1 hour then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

Extraction Process

The wet ZrO$_2$-based gel of Example 22 was removed from the ethanol bath, weighed, placed inside a small canvas pouch, and then stored briefly in another ethanol bath before being loaded into the 10-L extractor vessel. The wet weight of Example 22 was 22.1 grams. About 785 ml of 200-proof ethanol was added to the 10-L extractor of a laboratory-scale supercritical fluid extractor unit. The canvas bag containing the wet zirconia-based gel was transferred from the ethanol bath into the 10-L extractor so that the wet gel was completely immersed in the liquid ethanol inside the jacketed extractor vessel, which was heated and maintained at 60° C. The Example 22 sample was subjected to the same extraction process as described above for Examples 1 and 2 samples. Afterwards, the dry aerogel was removed from its canvas pouch, weighed, and transferred into a 237 ml glass jar packed with tissue paper for storage. The dry Example 22 aerogel was semi-translucent with a bluish tint and weighed 12.1 grams, corresponding to an overall weight loss during the supercritical extraction process of 45.7%.

Organic Burnout and Pre-sinter Process

The extracted Example 22 aerogel sample from above was removed from its closed container and set on a bed of zirconia beads in an alumina crucible, covered with alumina then fired in air according to the following schedule in a crucible furnace (Model 56724; "LINDBERG/BLUE M 1700° C."): i—heat from 20° C. to 600° C. at 10° C./hr. rate; ii—heat from 600° C. to 1090° C. at 120° C./hr. rate; iii-hold at 1090° C. for 1 hour; and iv—cool down from 1090° C. to 20° C. at 600° C./hr. rate.

After firing the sample was crack free. The cylinder was diced into about 1.8 mm thick wafers. The wafers were ion exchanged by first placing them in a 118 ml glass jar containing distilled water at a depth of about 2.5 cm and then vacuum infiltrating. The water was replaced with about a 2.5 cm depth of 1.0N NH₄OH and the wafers were soaked overnight for 16 hours or longer. The NH₄OH was then poured off and the jar was filled with distilled water. The wafers were soaked in the distilled water for 1 hour. The water was then replaced with fresh distilled water. This step was repeated until the pH of the soak water was equal to that of fresh distilled water. The wafers were then dried at 40° C.

Sintering Process

The wafer was set on a bed of zirconia beads in an alumina crucible, covered with alumina fiberboard then sintered in air according to the following schedule in a crucible furnace (Model 56724; "LINDBERG/BLUE M 1700° C."): i—heat from 20° C. to 1090° C. at 600° C./hr. rate; ii—heat from 1090° C. to 1250° C. at 120° C./hr. rate; iii—hold at 1250° C. for 2 hours; and iv—cool down from 1250° C. to 20° C. at 600° C./hr. rate.

The sintered wafer of Example 22 was polished on both faces using Buehler polishing equipment comprised of an electrically driven head ("VECTOR POWER HEAD") and a grinder-polisher ("BETA GRINDER-POLISHER"). First the sample was ground flat using a 45 micrometer metal bonded diamond disc (identified as Part No: 156145 from Buehler). Then 30 micrometer diamond lapping film ("3M DIAMOND LAPPING FILM 668X") was used until the majority of the 45 micrometer scratches were removed. Then 9 micrometer diamond lapping film ("3M DIAMOND LAPPING FILM 668X") was used until the majority of the 30 micrometer scratches were removed. Next the sample was polished using 3 micrometer diamond suspension ("METADI DIAMOND SUSPENSION") on a polishing cloth ("TEXMET POLISHING CLOTH") until the majority of the 9 micrometer scratches were removed. Finally the sample was polished using 0.25 micrometer diamond suspension ("METADI DIAMOND SUSPENSION") on a polishing cloth ("TEXMET POLISHING CLOTH") until the majority of the 3 micrometer scratches were removed. The wafer was mounted in a lapping fixture during grinding and polishing to maintain flat and parallel faces. The wafer was bonded to the lapping fixture using hot-melt adhesive ("QUICKSTICK 135"). One side of the wafer was ground and polished, then the wafer was remounted and the other side was ground and polished.

The total transmittance was 34.7%, the diffuse transmittance was 31.8%, and the haze was 95.3%, measured using the spectrophotometer procedure described earlier. The TLT and DLT spectra are designated in FIGS. 2 and 3 as 1022 and 1122, respectively. The sample thickness was 1.01 mm.

EXAMPLE 23

To prepare Example 23, Sol S4 was diafiltered and concentrated as described above for Sol T1. The resulting sol was 54.9 wt. % $ZrO_2/Y_2O_3$ and about 5.5 wt. % acetic acid. The sol (100.24 grams) was charged to a 500 ml round bottom (RB) flask. Ethanol (30 grams), acrylic acid (5.75 grams), and HEMA (4.5 grams) were added to the flask. 2,2'-azobis(2-methylbutyronitrile), ("VAZO 67") (0.4 gram) was added and the contents stirred for 4 hours. The contents of the flask were then purged with $N_2$ gas for 6 minutes). The sample (translucent and low viscosity) was charged to cylindrical containers (29 mm diameter). Each container was about 18 ml in volume and each was sealed on both ends (very little air gap was left between the top and liquid). The samples were allowed to stand about 1 hour then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hour then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

Extraction Process

The wet $ZrO_2$-based gel of Example 23 was removed from the ethanol bath, weighed, placed inside a small canvas pouch, and then stored briefly in another ethanol bath before being loaded into the 10-L extractor vessel. The wet weight of Example 23 was 19.6 grams. About 700 ml of 200-proof ethanol was added to the 10-L extractor of a laboratory-scale supercritical fluid extractor unit. The canvas bag containing the wet zirconia-based gel was transferred from the ethanol bath into the 10-L extractor so that the wet gel was completely immersed in the liquid ethanol inside the jacketed extractor vessel, which was heated and maintained at 60° C. The Example 23 sample was subjected to the same extraction process as described above for Examples 1 and 2 samples. Afterwards, the dry aerogel was removed from its canvas pouch, weighed, and transferred into a 237 ml glass jar packed with tissue paper for storage. The dry Example 23 aerogel was semi-translucent with a bluish tint and weighed 9.9 grams, corresponding to an overall weight loss during the supercritical extraction process of about 50%.

Organic Burnout and Pre-sinter Process

The extracted Example 23 aerogel sample from above was removed from its closed container and set on a bed of zirconia beads in an alumina crucible, covered with alumina then fired in air according to the following schedule in a crucible furnace (Model 56724; "LINDBERG/BLUE M 1700° C."): i—heat from 20° C. to 600° C. at 10° C./hr. rate ii—heat from 600° C. to 1000° C. at 120° C./hr. rate; iii-hold at 1000° C. for 1 hour; and iv—cool down from 1000° C. to 20° C. at 600° C./hr. rate.

After firing the sample was crack free. The cylinder was ion exchanged by first placing it in a 118 ml glass jar containing distilled water at a depth of about 2.5 cm and then vacuum infiltrating. The water was replaced with about a 2.5 cm depth of 1.0N NH₄OH and the cylinder was soaked overnight for 16 hours or longer. The NH₄OH was then poured off and the jar was filled with distilled water. The cylinder was soaked in the distilled water for 1 hour. The water was then replaced with fresh distilled water. This step was repeated until the pH of the soak water was equal to that of fresh distilled water. The cylinder was then dried at 60° C. overnight.

The cylinder was diced into about 1.8 mm thick wafers. The wafers were dried at 90-125° C.

Sintering Process

The wafer was set on a bed of zirconia beads in an alumina crucible, covered with alumina fiberboard then sintered in air according to the following schedule in a crucible furnace (Model 56724; "LINDBERG/BLUE M 1700° C."): i—heat from 20° C. to 1000° C. at 600° C./hr. rate; ii—heat from 1000° C. to 1225° C. at 120° C./hr. rate; iii—hold at 1225° C. for 2 hours; iv—cool down from 1225° C. to 20° C. at 600° C./hr. rate.

The sintered wafer of Example 23 was polished on both faces using Buehler polishing equipment comprised of an electrically driven head ("VECTOR POWER HEAD") and a grinder-polisher ("BETA GRINDER-POLISHER"). First the sample was ground flat using a 45 micrometer metal bonded diamond disc (identified as Part No: 156145 from Buehler). Then 30 micrometer diamond lapping film ("3M DIAMOND LAPPING FILM 668X") was used until the majority of the 45 micrometer scratches were removed. Then 9 micrometer diamond lapping film ("3M DIAMOND LAPPING FILM 668X") was used until the majority of the 30 micrometer scratches were removed. Finally the sample was polished using 3 micrometer diamond suspension ("METADI DIAMOND SUSPENSION") on a polishing cloth ("TEXMET POLISHING CLOTH") until the majority of the 9 micrometer scratches were removed. The final wafers were about 13 mm in diameter and 0.9 mm thick. The $T/T_L$ was measured to be 0.96 as described above. The average biaxial flexural strength was measured to be 1163 MPa using the test method described above. The grain size was measured to be 192 nm by FESEM examination of the fracture surface and using the line intercept method according to the methods described above.

EXAMPLE 24

For Example 24, a 48.8 gram sample of Sol C4 (prepared and diafiltered and concentrated as described above, 27.9 wt. % oxide and 3 wt. % acetic acid) and 153.2 grams of Sol T2 (prepared and diafiltered and concentrated as described above, 26.6 wt. % oxide and 2.55 wt. % acetic acid) was charged in to a 500 ml RB flask. Water (102.7 grams) was removed via rotary evaporation resulting in a viscous somewhat dry material. Ethanol (30.3 grams), acrylic acid (5.8 grams), HEMA (2.9 grams), and DI water (0.7 gram) were added to the flask. The contents were stirred overnight resulting in a fluid translucent sol. 2,2'-azobis(2-methylbutyronitrile) ("VAZO 67") (0.3 gram) was added and stirred until dissolved. The contents of the flask were then purged with $N_2$ gas for 6 minutes. The sample (translucent and low viscosity) was charged to cylindrical containers (29 mm diameter). Each container was about 18 ml in volume and each was sealed on both ends (very little air gap was left between the top and liquid). The samples were allowed to stand for about 1 hour then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

Extraction Process

The wet $ZrO_2$-based gel of Example 24 was removed from the ethanol bath, weighed, placed inside a small canvas pouch, and then stored briefly in another ethanol bath before being loaded into the 10-L extractor vessel. The wet weight of Example 24 was 20.2 grams. About 835 ml of 200-proof ethanol was added to the 10-L extractor of a laboratory-scale supercritical fluid extractor unit. The canvas bag containing the wet zirconia-based gel was transferred from the ethanol bath into the 10-L extractor so that the wet gel was completely immersed in the liquid ethanol inside the jacketed extractor vessel, which was heated and maintained at 60° C. The Example 24 sample was subjected to the same extraction process as described above for Examples 1 and 2 samples. Afterwards, the dry aerogel was removed from its canvas pouch, weighed, and transferred into a 237 ml glass jar packed with tissue paper for storage. The dry Example 24 aerogel was semi-translucent with a bluish tint and weighed 11.1 grams, corresponding to an overall weight loss during the supercritical extraction process of 45%.

Organic Burnout and Pre-sinter Process

The extracted Example 24 aerogel sample prepared above was removed from its closed container and set on a bed of zirconia beads in an unglazed porcelain crucible, covered with alumina fiberboard then fired in air according to the following schedule in a high temperature furnace ("THERMOLYNE Type 46200"): i—heat from 20° C. to 225° C. at 18° C./hr. rate; ii—hold at 225° C. for 24 hours; iii—heat from 225° C. to 400° C. at 6° C./hr. rate; iv—heat from 400° C. to 600° C. at 18° C./hr. rate v—heat from 600° C. to 1090° C. at 120° C./hr rate; and vi—cool down from 1090° C. to 20° C. at 600° C./hr. rate.

After firing the sample was crack free. The cylinder was diced into about 1 mm thick wafers. The Example 24 wafers were ion exchanged by first placing them in a 118 ml glass jar containing distilled water at a depth of about 2.5 cm and then vacuum infiltrating. The water was replaced with about a 2.5 cm depth of 1.0N $NH_4OH$ and the wafers were soaked overnight for 16 hours or longer. The $NH_4OH$ was then poured off and the jar was filled with distilled water. The wafers were soaked in the distilled water for 1 hour. The water was then replaced with fresh distilled water. This step was repeated until the pH of the soak water was equal to that of fresh distilled water. The wafers were then dried at 90-125° C. for a minimum of 1 hour.

The pre-sintered at 1090° C. aerogel of Example 24 had 46.5 volume % of oxides, as determined by dividing the geometric density of the pre-sintered wafer by the Archimedes density of the sintered wafer and then multiplying by 100.

Sintering Process

A wafer was set on a bed of zirconia beads in an alumina crucible, covered with alumina fiberboard then sintered in air according to the following schedule in a crucible furnace (Model 56724; "LINDBERG/BLUE M 1700° C."): i—heat from 20° C. to 1090° C. at 600° C./hr. rate; ii—heat from 1090° C. to 1250° C. at 120° C./hr. rate; iii—hold at 1250° C. for 2 hours; and iv—Cool down from 1250° C. to 20° C. at 600° C./hr. rate. This same wafer was sintered again as above but with a hold at 1250° C. for 20 hours.

The sintered wafer was polished on both faces using Buehler polishing equipment comprised of an electrically driven head ("VECTOR POWER HEAD") and a grinder-polisher ("BETA GRINDER-POLISHER"). The sample was ground flat on both sides using 30 micrometer diamond lapping film ("3M DIAMOND LAPPING FILM 668X"). Then 9 micrometer diamond lapping film ("3M DIAMOND LAPPING FILM 668X") was used on both sides until the majority of the 30 micrometer scratches were removed. Next the sample was polished on both sides using 6 micrometer diamond suspension ("METADI DIAMOND SUSPENSION") on a polishing cloth ("TEXMET POLISHING CLOTH"), until the majority of the 9 micrometer scratches were removed. Finally the sample was polished on both sides using 3 micrometer diamond suspension ("METADI DIAMOND SUSPENSION") on a polishing cloth ("TEXMET POLISHING CLOTH"), until the majority of the 6 micrometer scratches were removed. The Archimedes density and $T/T_L$ were measured as described above. The disc was submitted for x-ray diffraction to determine the phases present.

After XRD was done the sample was set on a bed of zirconia beads in an alumina crucible and thermally etched in air in a rapid temperature furnace (CM Furnaces Inc.) as follows: i—heat from 20° C. to 1200° C. at 450° C./hr. rate;

ii—hold at 1200° C. for 0.5 hour; and iii—cool from 1200° C. to 20° C. at 600° C./hr. rate.

FESEM was done on the thermally etched sample as described in the test method described above. The grain size was determined using the line intercept method described in the test method above.

The properties of the sintered wafer of Example 24 are given in Table 8, below.

TABLE 8

| Example | Archimedes Density, g/cm$^3$ | Polished Thickness, mm | Polished T/T$_L$ | Grain Size, nm | Strength, MPa | Phase Composition (XRD) |
|---|---|---|---|---|---|---|
| 24 | 6.04 | 0.54 | 1.08 | 168 | | [ZrO$_2$(Cl) 2% a = 5.39; ZrO$_2$(C2) 15% a = 5.15; ZrO$_2$(T) 83% a = 3.61 c = 5.18] |

EXAMPLE 25

For Example 25, a 48.8 gram sample of Sol C4 (prepared and diafiltered and concentrated as described above, 27.9 wt. % oxide and 3 wt. % acetic acid) and 153.2 grams of Sol T2 (prepared and diafiltered and concentrated as described above, 26.6 wt. % oxide and 2.55 wt. % acetic acid) was charged in to a 500 ml RB flask. Water (102.7 grams) was removed via rotary evaporation resulting in a viscous somewhat dry material. Ethanol (30.3 grams), acrylic acid (5.8 grams), HEMA (2.9 grams) and DI water (0.7 gram) were added to the flask. The contents were stirred overnight resulting in a fluid translucent sol. 2,2'-azobis(2-methylbutyronitrile) ("VAZO 67") (0.3 gram) was added and stirred until dissolved. The contents of the flask were then purged with N$_2$ gas (6 minutes). The sample (translucent and low viscosity) was charged to cylindrical containers (29 mm diameter). Each container was about 18 ml in volume and each was sealed on both ends (very little air gap was left between the top and liquid). The samples were allowed to stand for about 1 hr then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

Extraction Process

The wet ZrO$_2$-based gel of Example 25 was removed from the ethanol bath, weighed, placed inside a small canvas pouch, and then stored briefly in another ethanol bath before being loaded into the 10-L extractor vessel. The wet weight of Example 25 was 20.2 grams. About 835 ml of 200-proof ethanol was added to the 10-L extractor of a laboratory-scale supercritical fluid extractor unit. The canvas bag containing the wet zirconia-based gel was transferred from the ethanol bath into the 10-L extractor so that the wet gel was completely immersed in the liquid ethanol inside the jacketed extractor vessel, which was heated and maintained at 60° C.

The Example 25 sample was subjected to the same extraction process as described above for Examples 1 and 2 samples. Afterwards, the dry aerogel was removed from its canvas pouch, weighed, and transferred into a 237 ml glass jar packed with tissue paper for storage. The dry Example 25 aerogel was semi-translucent with a bluish tint and weighed 11.1 grams, corresponding to an overall weight loss during the supercritical extraction process of 45%.

Organic Burnout and Pre-sinter Process

The extracted Example 25 aerogel sample prepared above was removed from its closed container and set on a bed of zirconia beads in an unglazed porcelain crucible, covered with alumina fiberboard then fired in air according to the following schedule in a high temperature furnace ("THERMOLYNE Type 46200"): i—heat from 20° C. to 225° C. at 18° C./hr. rate; ii—hold at 225° C. for 24 hours; iii—heat from 225° C. to 400° C. at 6° C./hr. rate; iv—heat from 400° C. to 600° C. at 18° C./hr. rate; v—heat from 600° C. to 1090° C. at 120° C./hr. rate; and vi—cool down from 1090° C. to 20° C. at 600° C./hr. rate.

After firing the sample was crack free. The cylinder was diced into about 1 mm thick wafers. The Example 25 wafers were ion exchanged by first placing them in a 118 ml glass jar containing distilled water at a depth of about 2.5 cm and then vacuum infiltrating. The water was replaced with about a 2.5 cm depth of 1.0N NH$_4$OH and the wafers were soaked overnight for 16 hours or longer. The NH$_4$OH was then poured off and the jar was filled with distilled water. The wafers were soaked in the distilled water for 1 hour. The water was then replaced with fresh distilled water. This step was repeated until the pH of the soak water was equal to that of fresh distilled water. The wafers were then dried at 90-125° C. for a minimum of 1 hour.

The pre-sintered at 1090° C. aerogel of Example 25 had 46.6 volume % of oxides, as determined by dividing the geometric density of the pre-sintered wafer by the Archimedes density of the sintered wafer and then multiplying by 100.

Sintering Process

A wafer was set on a bed of zirconia beads in an alumina crucible, covered with alumina fiberboard then sintered in air according to the following schedule in a crucible furnace (Model 56724; "LINDBERG/BLUE M 1700° C."): i—heat from 20° C. to 1090° C. at 600° C./hr. rate; ii—heat from 1090° C. to 1500° C. at 120° C./hr. rate; iii—hold at 1500° C. for 2 hours; and iv—Cool down from 1500° C. to 20° C. at 600° C./hr. rate.

The sintered wafer was polished on both faces using Buehler polishing equipment comprised of an electrically driven head ("VECTOR POWER HEAD") and a grinder-polisher ("BETA GRINDER-POLISHER"). The sample was ground flat on both sides using 30 micrometer diamond lapping film ("3M DIAMOND LAPPING FILM 668X"). Then 9 micrometer diamond lapping film ("3M DIAMOND LAPPING FILM 668X") was used on both sides until the majority of the 30 micrometer scratches were removed. Next the sample was polished on both sides using 6 micrometer diamond suspension ("METADI DIAMOND SUSPENSION") on a polishing cloth ("TEXMET POLISHING CLOTH"), until the majority of the 9 micrometer scratches were removed. Finally the sample was polished on both sides using 3 micrometer diamond suspension ("METADI DIAMOND SUSPENSION") on a polishing cloth ("TEXMET POLISHING CLOTH"), until the majority of the 6 micrometer scratches were removed. The Archimedes density and T/T$_L$ were measured as described above. The disc was submitted for x-ray diffraction to determine the phases present.

After XRD was done the sample was set on a bed of zirconia beads in an alumina crucible and thermally etched in air in a rapid temperature furnace (CM Furnaces Inc.) as follows: i—heat from 20° C. to 1200° C. at 450° C./hr. rate; ii—hold at 1200° C. for 0.5 hour; and iii—cool from 1200° C. to 20° C. at 600° C./hr. rate.

FESEM was done on the thermally etched sample as described in the test method described above. The grain size was determined using the line intercept method described in the test method above.

The properties of the sintered wafer of Example 25 are given in Table 9, below.

TABLE 9

| Example | Archimedes Density, g/cm$^3$ | Polished Thickness, mm | Polished T/T$_L$ | Grain Size, nm | Strength, MPa | Phase Composition (XRD) |
|---|---|---|---|---|---|---|
| 25 | 6.05 | 0.57 | 1.00 | 444 | | [ZrO$_2$(C2) 50% a = 5.14; ZrO$_2$(T) 50% a = 3.60 c = 5.18] |

EXAMPLE 26

To prepare Example 26, Sol S3 was diafiltered and concentrated as described above for Sol T1. The resulting sol was 54.3 wt. % ZrO$_2$/Y$_2$O$_3$ and 5.6 wt. % acetic acid. The sol (50 grams) was charged to a 500 ml RB flask. Ethanol (15.15 grams), acrylic acid (2.9 gram) and ethoxylated pentaerythritol tetraacrylate ("SR454") (1.5 gram) were added to the flask. 2,2'-azobis(2-methylbutyronitrile) ("VAZO 67") (0.15 gram) was added and the contents stirred to dissolve the 2,2'-azobis(2-methylbutyronitrile) ("VAZO 67"). The contents of the flask were then purged with N$_2$ gas for 3 minutes. The sample (translucent and low viscosity) was charged to cylindrical containers (29 mm diameter). Each container was about 18 ml in volume and each was sealed on both ends (very little air gap was left between the top and liquid). The samples were allowed to stand about 12 hours then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.
Extraction Process The wet ZrO$_2$-based gel of Example 26 was removed from the ethanol bath, weighed, placed inside a small canvas pouch, and then stored briefly in another ethanol bath before being loaded into the 10-L extractor vessel. The wet weight of Example 26 was 21.4 grams. About 805 ml of 200-proof ethanol was added to the 10-L extractor of a laboratory-scale supercritical fluid extractor unit. The canvas bag containing the wet zirconia-based gel was transferred from the ethanol bath into the 10-L extractor so that the wet gel was completely immersed in the liquid ethanol inside the jacketed extractor vessel, which was heated and maintained at 60° C. The Example 26 sample was subjected to the same extraction process as described above for Examples 1 and 2 samples. Afterwards, the dry aerogel was removed from its canvas pouch, weighed, and transferred into a 237 ml glass jar packed with tissue paper for storage. The dry Example 26 aerogel was semi-translucent with a bluish tint and weighed 11.2 grams, corresponding to an overall weight loss during the supercritical extraction process of 47.7%.

EXAMPLE 27

To prepare Example 27, Sol S3 was diafiltered and concentrated as described above for Sol T1. The resulting sol was 54.2 wt. % ZrO$_2$/Y$_2$O$_3$ and 5.6 wt. % acetic acid. The sol (50 grams) was charged to a 500 ml RB flask. Ethanol (15.1 grams), acrylic acid (2.9 gram) and polyethylene glycol (400) dimethacrylate ("SR603") (1.5 gram) were added to the flask. 2,2'-azobis(2-methylbutyronitrile) ("VAZO 67") (0.15 gram) was added and the contents stirred to dissolve the 2,2'-azobis(2-methylbutyronitrile) ("VAZO 67"). The contents of the flask were then purged with N$_2$ gas for 3 minutes. The sample (translucent and low viscosity) was charged to cylindrical containers (29 mm diameter). Each container was about 18 ml in volume and each was sealed on both ends (very little air gap was left between the top and liquid). The samples were allowed to stand about 12 hours then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.
Extraction Process The wet ZrO$_2$-based gel of Example 27 was removed from the ethanol bath, weighed, placed inside a small canvas pouch, and then stored briefly in another ethanol bath before being loaded into the 10-L extractor vessel. The wet weight of Example 27 was 19.9 grams. About 765 ml of 200-proof ethanol was added to the 10-L extractor of a laboratory-scale supercritical fluid extractor unit. The canvas bag containing the wet zirconia-based gel was transferred from the ethanol bath into the 10-L extractor so that the wet gel was completely immersed in the liquid ethanol inside the jacketed extractor vessel, which was heated and maintained at 60° C. The Example 27 sample was subjected to the same extraction process as described above for Examples 1 and 2 samples. Afterwards, the dry aerogel was removed from its canvas pouch, weighed, and transferred into a 237 ml glass jar packed with tissue paper for storage. The dry Example 27 aerogel was semi-translucent with a bluish tint and weighed 11.1 grams, corresponding to an overall weight loss during the supercritical extraction process of 44.2%.

EXAMPLE 28

To prepare Example 28, Sol S3 was diafiltered and concentrated as described above for Sol T1. The resulting sol was 54.2 wt. % ZrO$_2$/Y$_2$O$_3$ and 5.6 wt. % acetic acid. The sol (50 grams) was charged to 500 ml RB flask. Ethanol (15.1 grams), acrylic acid (2.9 grams) and ethoxylated pentaerythritol tetraacrylate ("SR494") (1.5 gram) were added to the flask. 2,2'-azobis(2-methylbutyronitrile) ("VAZO 67") (0.15 gram) was added and the contents stirred to dissolve the 2,2'-azobis(2-methylbutyronitrile) ("VAZO 67"). The contents of the flask were then purged with N$_2$ gas for 3 minutes. The sample (translucent and low viscosity) was charged to cylindrical containers (29 mm diameter).

Each container was about 18 ml in volume and each was sealed on both ends (very little air gap was left between the top and liquid). The samples were allowed to stand about 12 hours then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

Extraction Process

The wet $ZrO_2$-based gel of Example 28 was removed from the ethanol bath, weighed, placed inside a small canvas pouch, and then stored briefly in another ethanol bath before being loaded into the 10-L extractor vessel. The wet weight of Example 28 was 22.2 grams. About 765 ml of 200-proof ethanol was added to the 10-L extractor of a laboratory-scale supercritical fluid extractor unit. The canvas bag containing the wet zirconia-based gel was transferred from the ethanol bath into the 10-L extractor so that the wet gel was completely immersed in the liquid ethanol inside the jacketed extractor vessel, which was heated and maintained at 60° C. The Example 28 sample was subjected to the same extraction process as described above for Examples 1 and 2 samples. Afterwards, the dry aerogel was removed from its canvas pouch, weighed, and transferred into a 237 ml glass jar packed with tissue paper for storage. The dry Example 28 aerogel was semi-translucent with a bluish tint and weighed 11.4 grams, corresponding to an overall weight loss during the supercritical extraction process of 48.6%.

EXAMPLE 29

To prepare Example 29, Sol S3 was diafiltered and concentrated as described above for Sol T1. The resulting sol was 54.2 wt. % $ZrO_2/Y_2O_3$ and 5.6 wt. % acetic acid. The sol (50 grams) was charged to 500 ml RB flask. Ethanol (15.3 grams), acrylic acid (2.9 grams) and ethoxylated (9) trimethylolpropane triacrylate ("SR502") (1.5 gram) were added to the flask. 2,2'-azobis(2-methylbutyronitrile), ("VAZO 67") (0.15 gram) was added and the contents stirred to dissolve the 2,2'-azobis(2-methylbutyronitrile), ("VAZO 67"). The contents of the flask were then purged with $N_2$ gas for 3 minutes. The sample (translucent and low viscosity) was charged to cylindrical containers (29 mm diameter). Each container was about 18 ml in volume and each was sealed on both ends (very little air gap was left between the top and liquid). The samples were allowed to stand about 12 hr then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

Extraction Process

The wet $ZrO_2$-based gel of Example 29 was removed from the ethanol bath, weighed, placed inside a small canvas pouch, and then stored briefly in another ethanol bath before being loaded into the 10-L extractor vessel. The wet weight of Example 29 was 22.5 grams. About 765 ml of 200-proof ethanol was added to the 10-L extractor of a laboratory-scale supercritical fluid extractor unit. The canvas bag containing the wet zirconia-based gel was transferred from the ethanol bath into the 10-L extractor so that the wet gel was completely immersed in the liquid ethanol inside the jacketed extractor vessel, which was heated and maintained at 60° C. The Example 29 sample was subjected to the same extraction process as described above for Examples 1 and 2 samples. Afterwards, the dry aerogel was removed from its canvas pouch, weighed, and transferred into a 237 ml glass jar packed with tissue paper for storage. The dry Example 29 aerogel was semi-translucent with a bluish tint and weighed 11.9 grams, corresponding to an overall weight loss during the supercritical extraction process of 47.1%.

EXAMPLE 30

To prepare Example 30, Sol S3 was diafiltered and concentrated as described above for Sol T1. The resulting sol was 54.2 wt. % $ZrO_2/Y_2O_3$ and 5.6 wt. % acetic acid. The sol (50 grams) was charged to 500 ml RB flask. Ethanol (15.15 grams), acrylic acid (2.9 grams) and ethoxylated (15) trimethylolpropane triacrylate ("SR9035") (1.5 gram) were added to the flask. 2,2'-azobis(2-methylbutyronitrile) ("VAZO 67") (0.15 gram) was added and the contents stirred to dissolve the 2,2'-azobis(2-methylbutyronitrile), ("VAZO 67"). The contents of the flask were then purged with $N_2$ gas for 3 minutes. The sample (translucent and low viscosity) was charged to cylindrical containers (29 mm diameter). Each container was about 18 ml in volume and each was sealed on both ends (very little air gap was left between the top and liquid). The samples were allowed to stand about 12 hours then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

Extraction Process

The wet $ZrO_2$-based gel of Example 30 was removed from the ethanol bath, weighed, placed inside a small canvas pouch, and then stored briefly in another ethanol bath before being loaded into the 10-L extractor vessel. The wet weight of Example 30 was 22.1 grams. About 765 ml of 200-proof ethanol was added to the 10-L extractor of a laboratory-scale supercritical fluid extractor unit. The canvas bag containing the wet zirconia-based gel was transferred from the ethanol bath into the 10-L extractor so that the wet gel was completely immersed in the liquid ethanol inside the jacketed extractor vessel, which was heated and maintained at 60° C. The Example 30 sample was subjected to the same extraction process as described above for Examples 1 and 2 samples. Afterwards, the dry aerogel was removed from its canvas pouch, weighed, and transferred into a 237 ml glass jar packed with tissue paper for storage. The dry Example 30 aerogel was semi-translucent with a bluish tint and weighed 11.9 grams, corresponding to an overall weight loss during the supercritical extraction process of 46.2%.

EXAMPLE 31

For Example 31, 92.36 grams of diafiltered and concentrated Sol C3 (29.5 wt. % oxide and 3.1 wt. % acetic acid)

was charged to 500 ml RB flask. Water (42.4 grams) was removed via rotary evaporation resulting in a viscous somewhat dry material. Ethanol (15.2 grams), acrylic acid (2.9 grams), ethoxylated pentaerythritol tetraacrylate ("SR454") (1.5 gram) were added to the flask. The contents were stirred about 2 days resulting in a fluid translucent sol. 2,2'-azobis (2-methylbutyronitrile), ("VAZO 67") (0.15 gram) was added and stirred until dissolved. The contents of the flask were then purged with $N_2$ gas for 3 minutes. The sample (translucent and low viscosity) was charged to cylindrical containers (29 mm diameter). Each container was about 18 ml in volume and each was sealed on both ends (very little air gap was left between the top and liquid). The samples were allowed to stand for about 1 hour then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

Extraction Process

The wet $ZrO_2$-based gel of Example 31 was removed from the ethanol bath, weighed, placed inside a small canvas pouch, and then stored briefly in another ethanol bath before being loaded into the 10-L extractor vessel. The wet weight of Example 31 was 21.7 grams. About 790 ml of 200-proof ethanol was added to the 10-L extractor of a laboratory-scale supercritical fluid extractor unit. The canvas bag containing the wet zirconia-based gel was transferred from the ethanol bath into the 10-L extractor so that the wet gel was completely immersed in the liquid ethanol inside the jacketed extractor vessel, which was heated and maintained at 60° C. The Example 31 sample was subjected to the same extraction process as described above for Examples 1 and 2 samples. Afterwards, the dry aerogel was removed from its canvas pouch, weighed, and transferred into a 237 ml glass jar packed with tissue paper for storage. The dry Example 31 aerogel was semi-translucent with a bluish tint.

EXAMPLE 32

For Example 32, 92.4 grams of diafiltered and concentrated Sol C3 (29.5 wt. % oxide and 3.1 wt. % acetic acid) was charged to a 500 ml RB flask. Water (42.3 grams) was removed via rotary evaporation resulting in a viscous somewhat dry material. Ethanol (15.2 grams), acrylic acid (2.9 grams), ethoxylated (15) trimethylolpropane triacrylate ("SR9035") (1.5 gram) were added to the flask. The contents were stirred about 2 days resulting in a fluid translucent sol. 2,2'-azobis(2-methylbutyronitrile), (VAZO 67") (0.15 gram) was added and stirred until dissolved. The contents of the flask were then purged with $N_2$ gas for 3 minutes. The sample (translucent and low viscosity) was charged to cylindrical containers (29 mm diameter). Each container was about 18 ml in volume and each was sealed on both ends (very little air gap was left between the top and liquid). The samples were allowed to stand for about 1 hour then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

Extraction Process

The wet $ZrO_2$-based gel of Example 32 was removed from the ethanol bath, weighed, placed inside a small canvas pouch, and then stored briefly in another ethanol bath before being loaded into the 10-L extractor vessel. The wet weight of Example 32 was 20.4 grams. About 790 ml of 200-proof ethanol was added to the 10-L extractor of a laboratory-scale supercritical fluid extractor unit. The canvas bag containing the wet zirconia-based gel was transferred from the ethanol bath into the 10-L extractor so that the wet gel was completely immersed in the liquid ethanol inside the jacketed extractor vessel, which was heated and maintained at 60° C. The Example 32 sample was subjected to the same extraction process as described above for Examples 1 and 2 samples. Afterwards, the dry aerogel was removed from its canvas pouch, weighed, and transferred into a 237 ml glass jar packed with tissue paper for storage. The dry Example 32 aerogel was semi-translucent with a bluish tint.

EXAMPLE 33

For Example 33, 83.1 grams of diafiltered and concentrated Sol C3 (29.5 wt. % oxide and 3.1 wt. % acetic acid) was charged to a 500 ml RB flask. Water (42.5 grams) was removed via rotary evaporation resulting in a viscous somewhat dry material. Ethanol (15.15 grams), acrylic acid (2.9 grams), butylacrylate (1.5 gram) were added to the flask. The contents were stirred overnight resulting in a fluid translucent sol. 2,2'-azobis(2-methylbutyronitrile), ("VAZO 67") (0.15 gram) was added and stirred until dissolved. The contents of the flask were then purged with $N_2$ gas for 3 minutes. The sample (translucent and low viscosity) was charged to cylindrical containers (29 mm diameter). Each container was about 18 ml in volume and each was sealed on both ends (very little air gap was left between the top and liquid). The samples were allowed to stand for about 1 hour then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

Extraction Process

The wet $ZrO_2$-based gel of Example 33 was removed from the ethanol bath, weighed, placed inside a small canvas pouch, and then stored briefly in another ethanol bath before being loaded into the 10-L extractor vessel. The wet weight of Example 33 was 21.2 grams. About 765 ml of 200-proof ethanol was added to the 10-L extractor of a laboratory-scale supercritical fluid extractor unit. The canvas bag containing the wet zirconia-based gel was transferred from the ethanol bath into the 10-L extractor so that the wet gel was completely immersed in the liquid ethanol inside the jacketed extractor vessel, which was heated and maintained at 60° C. The Example 33 sample was subjected to the same extraction process as described above for Examples 1 and 2 samples. Afterwards, the dry aerogel was removed from its canvas pouch, weighed, and transferred into a 237 ml glass jar packed with tissue paper for storage. The dry Example 33 aerogel was semi-translucent with a bluish tint and weighed 11.9 grams, corresponding to an overall weight loss during the supercritical extraction process of 43.9%.

EXAMPLE 34

For Example 34, 117.9 grams of diafiltered and concentrated Sol C2 (23.1 wt. % oxide and 2.4 wt. % acetic acid)

was charged to a 500 ml RB flask. Water (67.9 grams) was removed via rotary evaporation resulting in a viscous somewhat dry material. Ethanol (15.2 grams), acrylic acid (4.6 grams), HEMA (2.4 grams) and DI water (1.8 gram) were added to the flask. The contents were stirred overnight resulting in a fluid translucent sol. 2,2'-azobis(2-methylbutyronitrile), ("VAZO 67") (0.15 gram) was added and stirred until dissolved. The contents of the flask were then purged with $N_2$ gas for 3 minutes. The sample (translucent and low viscosity) was charged to cylindrical containers (29 mm diameter). Each container was about 18 ml in volume and each was sealed on both ends (very little air gap was left between the top and liquid). The samples were allowed to stand for about 1 hour then placed in an oven to cure (50° C., 4 hours). This results in a clear translucent blue gel. The gel was removed from the container and placed in a 473 ml wide mouth jar. The jar was filled with ethanol (denatured). The sample was soaked for 24 hours then the ethanol was replaced with fresh ethanol. The sample was soaked for 24 hours then the ethanol was replaced with a third batch of fresh ethanol. The sample was allowed to soak until the supercritical extraction was done. The above manipulations were done minimizing the amount of time the gel was exposed to the air.

Extraction Process

The wet $ZrO_2$-based gel of Example 34 was removed from the ethanol bath, weighed, placed inside a small canvas pouch, and then stored briefly in another ethanol bath before being loaded into the 10-L extractor vessel. The wet weight of Example 34 was 20.6 grams. About 820 ml of 200-proof ethanol was added to the 10-L extractor of a laboratory-scale supercritical fluid extractor unit. The canvas bag containing the wet zirconia-based gel was transferred from the ethanol bath into the 10-L extractor so that the wet gel was completely immersed in the liquid ethanol inside the jacketed extractor vessel, which was heated and maintained at 60° C. The Example 34 sample was subjected to the same extraction process as described above for Examples 1 and 2 samples. Afterwards, the dry aerogel was removed from its canvas pouch, weighed, and transferred into a 237 ml glass jar packed with tissue paper for storage. The dry Example 34 aerogel was semi-translucent with a bluish tint and weighed 11.5 grams, corresponding to an overall weight loss during the supercritical extraction process of 44.2%.

Foreseeable modifications and alterations of this disclosure will be apparent to those skilled in the art without departing from the scope and spirit of this invention. This invention should not be restricted to the embodiments that are set forth in this application for illustrative purposes.

What is claimed is:

1. A monolithic aerogel comprising organic material and crystalline metal oxide particles, wherein the crystalline metal oxide particles are in a range from 3 to 20 volume percent, based on the total volume of the monolithic aerogel, wherein at least 70 mole percent of the crystalline metal oxide is $ZrO_2$.

2. The monolithic aerogel of claim 1, wherein the crystalline metal oxide particles comprise 1 to 15 mole percent $Y_2O_3$.

3. The monolithic aerogel of claim 1, wherein the crystalline metal oxide particles have an average primary particle size in a range of 2 nanometers to 50 nanometers.

4. The monolithic aerogel of claim 1, wherein the crystalline material further comprises at least one of $Y_2O_3$ or $La_2O_3$.

5. The monolithic aerogel of claim 1, wherein the $ZrO_2$ is all tetragonal or cubic.

6. The monolithic aerogel of claim 1, wherein the organic content in a range of 3 to 30 percent by weight, based on the total weight of the aerogel.

7. The monolithic aerogel of claim 1, wherein the aerogel has a surface area in a range of 100 $m^2$/gram to 300 $m^2$/gram.

8. The monolithic aerogel of claim 1, wherein an average connected pore size is in a range of 10 nanometers to 20 nanometers.

9. The monolithic aerogel of claim 1, wherein the aerogel is crack-free.

10. The monolithic aerogel of claim 1, wherein the organic material content is in a range of 3 to 30 weight percent, based on a total weight of the aerogel.

11. The monolithic aerogel of claim 1, wherein the crystalline metal oxide particles further comprise at least one of $Fe_2O_3$, $MnO_2$, $Co_2O_3$, $Cr_2O_3$, NiO, CuO, $Bi_2O_3$, $Ga_2O_3$, $Er_2O_3$, $Pr_2O_3$, $Eu_2O_3$, $Dy_2O_3$, $Sm_2O_3$, or $CeO_2$.

12. The monolithic aerogel of claim 1, wherein the crystalline metal oxide particles further comprise at least one of $CeO_2$, $Pr_2O_3$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Tm_2O_3$, $Yb_2O_3$, $Fe_2O_3$, $MnO_2$, $Co_2O_3$, $Cr_2O_3$, NiO, CuO, $Bi_2O_3$, $Ga_2O_3$, or $Lu_2O_3$.

13. The monolithic aerogel of claim 1, wherein the organic material comprises a polymer prepared from one or more radically polymerizable monomers.

14. The monolithic aerogel of claim 13, wherein the one or more radically polymerizable monomers comprise a radically polymerizable surface modifier for $ZrO_2$.

15. The monolithic aerogel of claim 1, wherein the crystalline metal oxide particles are surface modified.

16. A method of making an aerogel comprising organic material and crystalline metal oxide particles, wherein the crystalline metal oxide particles are in a range from 3 to 20 volume percent, based on the total volume of the aerogel, wherein at least 70 mole percent of the crystalline metal oxide is $ZrO_2$, the method comprising:
   providing a first zirconia sol comprising crystalline metal oxide particles having an average primary particle size of not greater than 50 nanometers, wherein at least 70 mole percent of the crystalline metal oxide is $ZrO_2$;
   optionally concentrating the first zirconia sol to provide as concentrated zirconia sol;
   adding a radically reactive surface modifier to the zirconia sol to provide a radically polymerizable surface-modified zirconia sol;
   adding a radical initiator to the radically polymerizable surface-modified zirconia sol;
   heating at least one temperature for a time sufficient to polymerize the radically surface-modified zirconia sol comprising the radical initiator to form a gel;
   optionally removing water, if present, from the gel via alcohol exchange to provide an at least partially de-watered gel; and
   extracting alcohol, if present, from the gel via super critical extraction to provide the aerogel.

17. The method of claim 16, further comprising adding a radically reactive co-monomer to the concentrated zirconia sol.

* * * * *

UNITED STATES PATENT AND TRADEMARK OFFICE
CERTIFICATE OF CORRECTION

PATENT NO. : 9,925,126 B2
APPLICATION NO. : 15/486579
DATED : March 27, 2018
INVENTOR(S) : Brant Kolb et al.

It is certified that error appears in the above-identified patent and that said Letters Patent is hereby corrected as shown below:

Column 11
Line 22, delete "$ZrO_{((4-n/2)}$" and insert -- $ZrO_{((4-n)/2)}$ --, therefor.

Column 12
Lines 31-32 (approx.), delete "autogeneous" and insert -- autogenous --, therefor.

Column 18
Line 34, delete "nonreactive" and insert -- non-reactive --, therefor.

Column 21
Line 33, delete "pthalic" and insert -- phthalic --, therefor.
Line 35, delete "hyroxyethyl" and insert -- hydroxyethyl --, therefor.
Lines 35-36, delete "hydoxypropyl" and insert -- hydroxypropyl --, therefor.
Line 36, delete "hydoxyproyl" and insert -- hydroxypropyl --, therefor.
Lines 47-48, delete "acyrloxyalkyldialkylalkoxysilanes" and insert
-- acryloxyalkyldialkylalkoxysilanes --, therefor.
Line 49, delete "mercaptoalkyltrialkoxylsilanes" and insert -- mercaptoalkyltrialkoxysilanes --, therefor.

Column 22
Line 37, delete "pyrrolidione" and insert -- pyrrolidone --, therefor.
Lines 64-65, delete "azobisisobututyronitrile" and insert -- azobisisobutyronitrile --, therefor.

Column 23
Line 3, delete "(cyclohexanecabonitrile)" and insert -- (cyclohexanecarbonitrile) --, therefor.
Line 20, delete ""DAROCURE" and insert -- "DAROCUR --, therefor.
Line 21, delete "phenylposphineoxide" and insert -- phenylphosphineoxide --, therefor.

Column 24
Line 20, delete "methaacrylate," and insert -- methacrylate, --, therefor.

Signed and Sealed this
Twenty-fifth Day of September, 2018

Andrei Iancu
*Director of the United States Patent and Trademark Office*

Line 25, delete "teteraacrylate" and insert -- tetraacrylate --, therefor.
Line 30, delete "carboxlic" and insert -- carboxylic --, therefor.

Column 26
Line 25, delete "cid," and insert -- acid, --, therefor.

Column 30
Line 53, delete "hysterese" and insert -- hysteresis --, therefor.

Column 35
Line 23, delete "1° F." and insert -- 10F --, therefor.

Column 43
Line 7, delete "nm" and insert -- run --, therefor.
Line 40, delete "weigh$_{wet}$" and insert -- weight$_{wet}$ --, therefor.

Column 44
Line 53, delete "$\rho_t$" and insert -- $\rho_{rel}$ --, therefor.

Column 45
Line 54, delete "AMBERLYTE" and insert -- AMBERLITE --, therefor.
Line 64 (approx.), delete "Lathanum" and insert -- Lanthanum --, therefor.

Column 46
Line 6 (approx.), delete "pyrrolidione" and insert -- pyrrolidone --, therefor.
Line 7 (approx.), delete "pyrrolidione" and insert -- pyrrolidone --, therefor.

Column 50
Line 1, delete "wt %" and insert -- wt. % --, therefor.
Line 15, delete "mlwide" and insert -- ml wide --, therefor.
Line 25, delete "wt %" and insert -- wt. % --, therefor. (First Occurrence)
Line 25, delete "wt %" and insert -- wt. % --, therefor. (Second Occurrence)

Column 65
Line 5 (approx.), delete "ZrO$_2$based" and insert -- ZrO$_2$-based --, therefor.

Column 73
Line 1, delete "respectively" and insert -- respectively, --, therefor.

Column 75
Line 16 (approx.), delete "oxides" and insert -- oxides, --, therefor.

Column 76
Line 55, delete "pyrrolidione" and insert -- pyrrolidone --, therefor.

CERTIFICATE OF CORRECTION (continued)
U.S. Pat. No. 9,925,126 B2

Column 78
Line 56, delete "C./hr.rate;" and insert -- C./hr. rate; --, therefor.

Column 104
Line 45, in Claim 16, delete "$ZrO_2$," and insert -- $ZrO_2$; --, therefor.